(12) United States Patent
Glazebrook et al.

(10) Patent No.: US 6,620,985 B1
(45) Date of Patent: Sep. 16, 2003

(54) PAD4 NUCLEIC ACID COMPOSITIONS FROM ARABIDOPSIS AND METHODS THEREFOR

(75) Inventors: Jane Glazebrook, San Diego, CA (US); Dayadevi Jirage, Hyattsville, MD (US); Tina L. Tootle, Boston, MA (US); Nan Zhou, Durham, NC (US); Bart Julienne Frans Feys, Norwich (GB)

(73) Assignees: University of Maryland Biotechnology Institute, Baltimore, MD (US); Plant Bioscience Limited, Norfolk (GB)

( * ) Notice: Subject to any disclaimer, the term of this patent is extended or adjusted under 35 U.S.C. 154(b) by 0 days.

(21) Appl. No.: 09/434,840

(22) Filed: Nov. 4, 1999

Related U.S. Application Data
(60) Provisional application No. 60/183,020, filed on Nov. 12, 1998.

(51) Int. Cl.$^7$ .......................... C12N 5/14; C12N 15/29; C12N 15/82

(52) U.S. Cl. .................... 800/278; 435/320.1; 435/419; 536/23.6

(58) Field of Search .............................. 435/69.1, 320.1, 435/419, 468; 536/23.6; 800/278, 279, 298, 301

(56) References Cited

U.S. PATENT DOCUMENTS 5,629,470 A    5/1997    Lam et al. .................... 800/205

FOREIGN PATENT DOCUMENTS

| WO | WO 98/06748 | 2/1998 |
| WO | WO 98/18939 | 5/1998 |
| WO | WO 98/53073 | 11/1998 |

OTHER PUBLICATIONS

Marra, et al., Mus musculus cDNA clone, Sep. 1997 GenBank Accession No. AA549289.

Purnelle, et al., Sep. 9, 1999, "Hypothetical 61 kd protein" GenBank Accession No. CAB43438.

Purnelle, et al., "*Arabidopsis thaliana* DNA chromosome 3, BAC clone F2206", Direct Submission, GenBank Accession No. AL050300: Submitted Jun. 9, 1999.

Bent, A.F., "Plant Disease Resistance Genes: Function Meets Structure," *The Plant Cell*, 8:1757–1771, Oct. 1996.

Camilleri, et al., "A YAC Contig Map of *Arabidopsis Thaliana* Chromosome 3," *The Plant Journal*, 14(5):633–642, 1998.

Cao, et al., "Generation of Broad–Spectrum Disease Resistance by Overexpression of an Essential Regulatory Gene in Systemic Acquired Resistance," *Proc Natl Acad Sci USA*, 95:6531–6536, May, 1998.

Century, et al., "NDR1, A Pathogen–Induced Component Required for Arabidopsis Disease Resistance," *Science*, 278:1963–1965, Dec. 1997.

Glazebrook, J. and Ausubel, F.M., "Isolation of Phytoalexin–Deficient Mutants of *Arabidopsis Thaliana* and Characterization of Their Interactions With Bacterial Pathogens," *Proc Natl Acad Sci, USA*, 91:8955–8959, Sep. 1994.

Glazebrook, et al., "Isolation of Arabidopsis Mutants With Enhanced Disease Susceptibility by Direct Screening," *Genetics*, 143:973–982, Jun. 1996.

Glazebrook, et al., "Phytoalexin–Deficient Mutants of Arabidopsis Reveal That PAD4 Encodes a Regulatory Factor and That Four PAD Genes Contribute to Downy Mildew Resistance," *Genetics*, 146:381–392, May 1997.

Oldroyd, G.E.D. and Staskawicz, B.J., "Genetically Engineered Broad–Spectrum Disease Resistance in Tomato," *Proc Natl Acad Sci, USA*, 95:10300–10305, Aug. 1998.

Rogers, E.E. and Ausubel, F.M., "Arabidopsis Enhanced Disease Susceptibility Mutants Exhibit Enhanced Susceptibility to Several Bacterial Pathogens and Alterations in PR–1 Gene Expression," *The Plant Cell*, 9:305–316, Mar. 1997.

Sato, et al., "A Physical Map of *Arabidopsis Thaliana* Chromosome 3 Represented by Two Contigs of CIC YAC, P1, TAC and BAC Clones," *DNA Research*, 5:163–168, 1998.

Slusarenko, et al., "A Convenient, Sensitive and Rapid Assay for Antibacterial Activity of Phytoalexins," *Botanica Helvetica*, 99(2): 203–207, 1989.

Tsuji, et al., "Phytoalexin Accumulation in *Arabidopsis Thaliana* During the Hypersensitive Reaction to *Pseudomonas syringae* pv syringae," *Plant Physiol*, 98:1304–1309, 1992.

Zhou, et al., "PAD4 Functions Upstream From Salicylic Acid to Control Defense Responses in Arabidopsis," *The Plant Cell*, 10:1021–1030, Jun. 1998.

Parker, J., "Unraveling Disease Resistance Pathways in Arabidopsis," The Discovery Meetings, Canberra Australia, (4 pages), Jul. 2, 1999.

(List continued on next page.)

*Primary Examiner*—Amy J. Nelson
(74) *Attorney, Agent, or Firm*—Akin Gump Strauss Hauer & Feld, L.L.P.

(57) ABSTRACT

PAD4 compositions from Arabidopsis, including genomic and cDNA nucleic acid sequences, and methods for using said compositions in plants are provided. PAD4 from Arabidopsis is demonstrated to be regulatory and is required upstream from salicylic acid in the signal transduction pathway leading from infection to activation of defense responses.

10 Claims, 36 Drawing Sheets

OTHER PUBLICATIONS

Parker, et al., "Molecular Genetic Dissection of R–Gene–Mediated Disease Resistance Pathways," $10^{th}$ International Conference on Arabidopsis Research, Melbourne, Australia, Abstract #72, Jul. 4–8, 1999.

Feys, et al., "Two–Hybrid Analysis Reveals Interactions Between EDS1 and PAD4, Two Essential Components of R–Gene–Mediated Signaling in Arabidopsis," $10^{th}$ International Conference on Arabidopsis, Melbourne, Australia, Abstract #7–10 and 5 attached figures, Jul. 4–8, 1999.

Parker, et al., "Dissection of R–Gene–Mediated Signalling Pathways in Arabidopsis," The Thirteenth John Innes Symposium: Attack & Defence in Plant Disease, Norfolk, United Kingdom, Abstract and 3 attached figures, Jul. 20–23, 1999.

Glazebrook, et al., "The Roles of Arabidopsis thaliana PAD and EDS Genes in Disease Resistance," Molecular Plant Microbe Interactions Ninth International Congress, Amsterdam, The Netherlands, Abstract #15.24 and copies of 7 slides, p. 167, Jul. 25–30, 1999.

Aarts, et al., Different Requirements of EDS1 and NDR1 by Disease Resistance Genes Define At Least Two R Gene–Mediated Signaling Pathways in Arabidopsis, Proc. Natl. Acad. Sci. USA, 95:10306–10311, Aug. 1998.

Falk, et al., "EDS1, An Essential Component of R Gene–Mediated Disease Resistance in Arabidopsis Has Homology to Eukaryotic Lipases," Proc. Natl. Acad. Sci., USA, 96:3292–3297, Mar. 1999.

Parker, et al., "Characterization of eds1, A Mutation in Arabidopsis Suppressing Resistance to Peronospora Parasitica Specified by Several Different RPP Genes," The Plant Cell, 8:2033–2046, Nov. 1996.

Reuber, et al., "Correlation of Defense Gene Induction Defects With Powdery Mildew Susceptibility in Arabidopsis Enhanced Disease Susceptibility Mutants," The Plant Journal, 16(4):473–485, 1998.

Reuber, et al., "Isolation of Arabidopsis Genes That Differentiate Between Resistance Responses Mediated By the RPS2 and RPM1 Disease Resistance Genes," The Plant Cell, 8:241–249, Feb. 1996.

Glazebrook, et al., "Genetic Dissection of Plant Defense Response Using Arabidopsis Thaliana," Summary of part of presentation at Center for Agricultural Biotechnology, (27 pages), College Park, MD, Nov. 12, 1998.

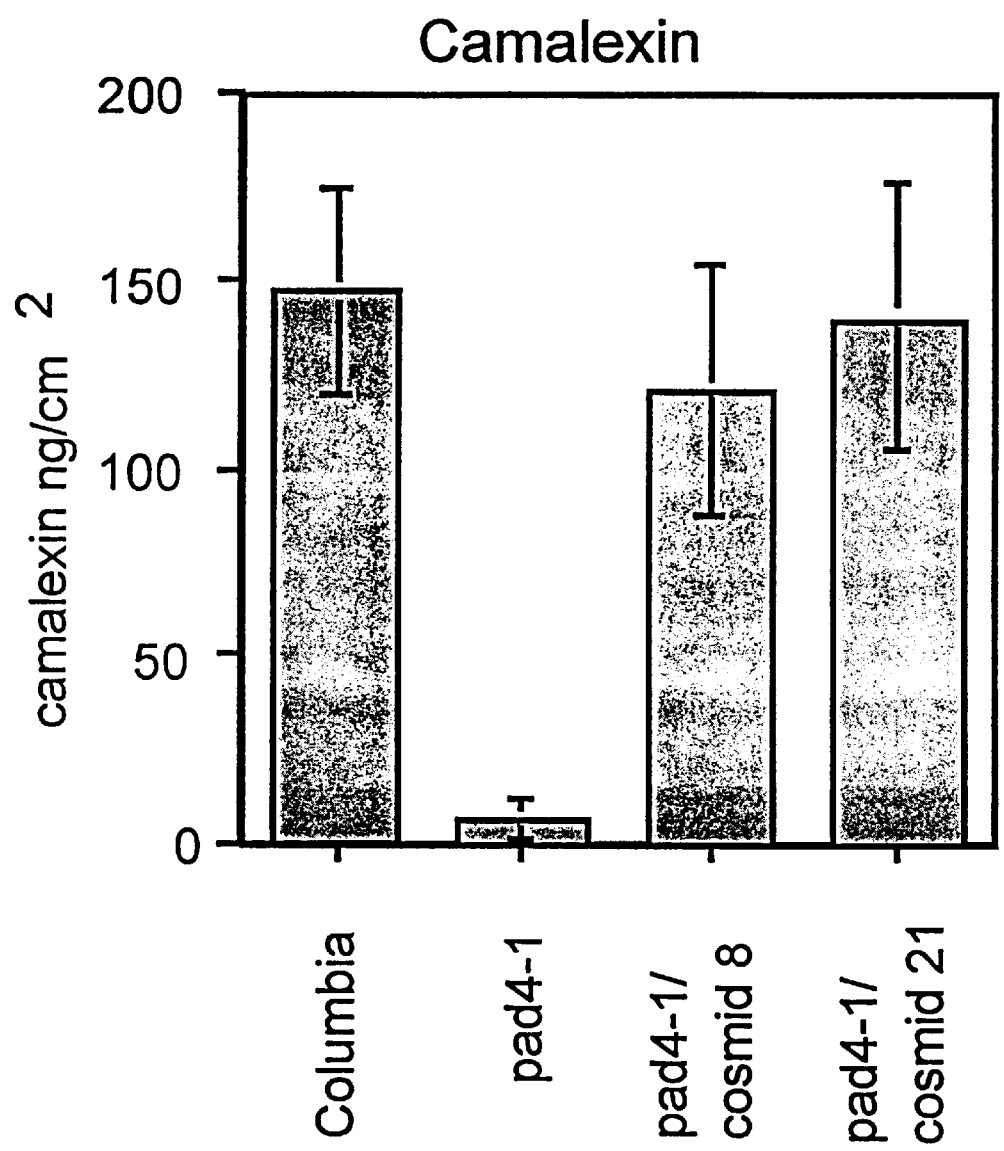

FIG. 11B

```
       STGIPX------YRVVHXNDIVPRLPPAXFGYLHTGVEY
                  90        100       110       120
217    QQTGAE-------        YRV  T GD DPVPRLPP IV  FGY RHT SP EY
284    STGIP Y------R        RT VNER DIVP    A FG F LH AG EE EY
314    STGIP F------Q        RT VH KR DIVP    QS FG F LH P GVE S
209    VQTGGT------L         YR IT HT TNDIVPRLPP RE FGY S SSP EY
144    -T S I SRSRLAHNFCH     VV SIH DLVPR     SSNEQ F WPFG T YLFC
195    DAFQVSSPETTQYF        RV TH SND GI PN LPPA DE GY A G GVEY

WIK-GGT-LVQVYTVD-ETKVCSGSA---T--LDHLS---
                  130       140       150       160
250    WLN- GG P-   LDKD YIV  T-  EI KVC EGI A------NVMC
317    WI TDNSPET   VQV CTS SD LET CS N S IVPF  T SV LDHLS YFG
347    WIK -S GT SN VQ IC  T SEI DCS N S IVPF  T SI LDHLS YFD
243    WIK -S GT -  LV PVTRN D-IV KIEGID-----ATGG
183    SD R- GG VC L DNAGS V RLMFNILNTT A TQN T EEHQRY  GHYV
235    W S---------  VDP YSAQ-N  T FVC TG------- D EVQ
```

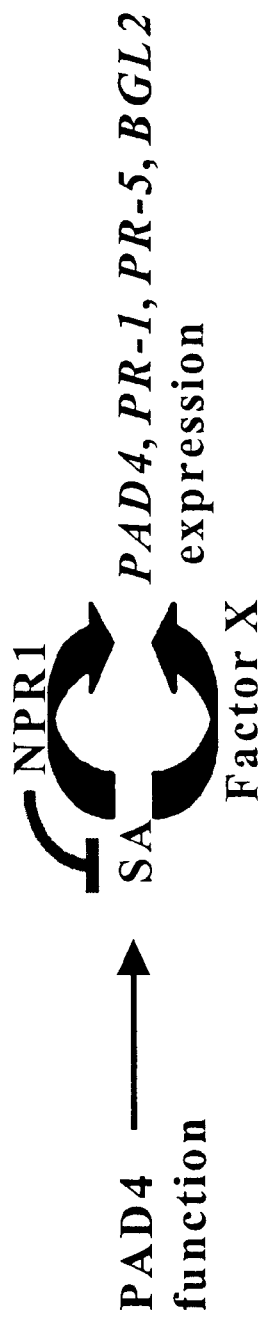

FIG. 19A

```
RhizoTGL  199  TKVHKGFLDSYGEVQN-ELVATVLDQFKQYPSYKVAVTGHSLGGATALLCALGLYQR  254
FusaTGL   139          VHTGFLDAWEEVAA-NVKAAVSAAKTANPTFKFVVTGHSLGGAVATIAAA-YLR  190
Rhizolip  228  AKVHAGFLSSYEQVVN-DYFPVVQEQLTAHPTYKVIVTGHSLGAQALLAGMDLYQR  283
Thermolip 129  CRGHDGFTSSWRSVAD-TLRQKVEDAVREHPDYRVVFTGHSLGGALATVAGAD--LR  182
AspFAE    115  CEVHGGYYIGWISVQD-QVESLVKQQASQYPDYALTVTGHSLGASMAALTAA--QLS  168
AtEDS1     83  ATVNEAFLKNLEAVIDPRTSFQASVEMAVRSRKQIVFTGHSSGGATAILATVWYLEKYFI  142
AtPAD4     79  DEPLPMVDAAILKLFL-QLKIKEGLELELLGKKLVVITGHSTGGALAAFTALWLLSQ  134
                                                    →
```

FIG. 19B

```
RhizoTGL   250  GLYQREEGLSSSNLFLYTQGQPRVGDPAFANYV-VSTGIP------YRRTVNERDIVPHL  302
FusaTGL    189  LRKDG--FP--FDLYTYGSPRVGNDFFANFVTQQTGAE------Y-RVTHGDDPVPRL   235
Rhizolip   282  YQREPRLSPKNLSIFTVGGPRVGNPTFAYYV-ESTGIP------FQRTVHKRDIVPHV   332
Thermolip  181  LRGNG--YD--IDVFSYGAPRVGNRAFAEFLTVQTGGT------LYRITHTNDIVPRL   228
AspFAE     168  SATYDN------VRLYTFGEPRSGNQAFASYMNDAFQVSSPETTQYFRVTHSNDGIPNL  220
AtEDS1     145  PNVYLEP------RCVTFGAPLVGDSIFSHALGREKWSR------FFVNFVTRFDIVPRI  192
AtPAD4     133  SQSSPPSFR--VFCITFGSPLLGNQSLSTSISRSRLAHN------FCHVVSIHDLVPRS  183
                                                                              →
```

PAD4 NUCLEIC ACID COMPOSITIONS FROM ARABIDOPSIS AND METHODS THEREFOR

The present application claims priority to Provisional Application No. 60/183,020, filed Nov. 12, 1998.

The government owns certain rights in the present invention pursuant to grant number MCB 9723493 from the National Science Foundation.

FIELD OF THE INVENTION

The present invention relates to compositions obtainable from plants, and methods for enhancing disease resistance of plants using the compositions. More particularly, the invention relates to nucleic acid compositions and encoded polypeptides, as well as microorganisms and plants transformed with the nucleic acid for production of encoded polypeptides.

BACKGROUND OF THE INVENTION

When a plant pathogen interacts with a potential host, it may successfully colonize the host and cause disease, in which case the pathogen is said to be virulent, the host is susceptible, and the interaction is compatible. Alternatively, the plant may respond to the pathogen by rapidly activating a battery of defense responses, interfering with pathogen multiplication and preventing disease. In this case, the pathogen is said to be avirulent, the host is resistant, and the interaction is incompatible. The outcomes of plant-pathogen interactions often fit a "gene-for-gene" model. In this model, resistance results when the pathogen carries a particular avirulence gene that corresponds to a particular resistance gene (R gene) in the host. In general, each R gene confers resistance only to pathogens carrying the corresponding avirulence gene. Gene-for-gene resistance responses have been observed in interactions of plants with a wide variety of pathogens, including fungi, bacteria and viruses. A simple molecular explanation for gene-for-gene resistance is that avirulence genes encode ligands that bind to receptors encoded by the plant R genes or that avirulence gene products synthesize such ligands. Ligand binding triggers activation of a signal transduction cascade culminating in expression of defense responses that inhibit the pathogen and confer resistance. The hallmark of gene-for-gene resistance is a rapid programmed cell death of the cells in contact with the pathogen, called the hypersensitive response, or HR.

In many cases, gene-for-gene resistance reactions trigger another form of strong disease resistance called systemic acquired resistance, or SAR. Infection by a necrotizing pathogen (a pathogen that causes host cell death) causes a signal to be transmitted throughout the plant. In response, defense genes are activated in uninfected tissue, and the plant shows resistance to subsequent infection by a wide range of normally compatible pathogens. It is clear that salicylic acid (SA) plays a key role in establishment of SAR; resistant tissue contains elevated levels of SA, treatment of plants with SA induces defense gene expression and resistance, and SA is required in the responding tissue for defense gene expression and resistance. The question of whether or not SA is also the systemic signal has not yet been settled.

Genetic analyses using Arabidopsis-pathogen systems are being used to dissect the signaling pathways governing gene-for-gene resistance and SAR. Common pathogens used include the virulent *Pseudomonas syringae* strains *Pseudomonas syringae* pv. *maculicola* (Psm ES4326) and *Pseudomonas syringae* pv. *tomato* (Pst DC3000), Gram-negative bacteria that cause "bacterial speck" diseases in many crop plants, as well as isogenic strains carrying any of several cloned avirulence genes that elicit gene-for-gene resistance responses. In addition, a large number of isolates of *Peronospora parasitica* have been characterized and used to define many R genes in various Arabidopsis accessions. Several R genes have been isolated from Arabidopsis and other species. Comparison of the amino acid sequences of the R proteins has resulted in their division into several major classes.

Less progress has been made in identifying factors acting immediately downstream of R genes in gene-for-gene resistance. The Arabidopsis mutants ndr1 and eds1 have properties suggesting that NDR1 and EDS1 may be such factors. Mutations in either ndr1 or eds1 interfere with gene-for-gene resistance conferred by subsets of R genes.

Infection of Arabidopsis by *P. syringae* induces many defense responses, including synthesis of the phytoalexin camalexin, and expression of the pathogenesis-related genes PR-1 and PR-5, β-glucanase (BGL2), and anthranilate synthase (ASA1). Phytoalexins are small molecule broad-spectrum antimicrobial compounds synthesized by plants in response to pathogen attack. Camalexin is the only phytoalexin produced in significant quantities by Arabidopsis. Infection by a *P. syringae* strain carrying an avirulence gene such as avrRpt2 or treatment with SA induces SAR. SAR correlates with systemic expression of PR-1, PR-5, and BGL2.

SA-dependent signaling has been studied using genetic analysis in Arabidopsis. The central role of SA in defense response signaling was revealed by characterization of transgenic plants expressing nahG. The nahG transgene encodes salicylate hydroxylase, an enzyme that converts SA to catechol. Thus, nahG plants are unable to accumulate SA, and are conceptually similar to mutants deficient in SA. Arabidopsis nahG plants fail to develop SAR in response to SA or necrotizing pathogens. They are also compromised in local resistance, displaying reduced PR-1 expression in response to infection, susceptibility to pathogens that are normally avirulent as a consequence of gene-for-gene resistance, and heightened susceptibility to normally virulent pathogens. Although camalexin synthesis is not inducible by SA, nahG plants fail to synthesize camalexin in response to local Psm ES4326 infection, suggesting that SA is necessary, but not sufficient, for activation of camalexin synthesis. Taken together, these results show that SA is important in gene-for-gene resistance and in limiting growth of virulent pathogens, as well as in SAR.

Several Arabidopsis mutants that constitutively express SAR have been isolated. Many of these mutants are "lesion-mimics", that is, they spontaneously develop necrotic lesions in the absence of any pathogen. After developing lesions, these plants accumulate high levels of SA, express PR-1 and are more resistant to pathogens. It is thought that lesion formation mimics the HR, thereby activating the SAR pathway in the rest of the plant. The lesion-mimic mutations appear to be acting upstream from SA in that they exhibit elevated SA levels and introduction of nahG reduces SA levels and abolishes PR-1 expression and resistance. In some, but not all lesion-mimics, introduction of nahG also abolishes lesion formation, strongly suggesting the existence of a positive feedback loop between cell death and SA accumulation. The cpr1 and cpr6 mutants constitutively express PR-1 and exhibit elevated SA levels, but do not spontaneously develop lesions. These mutations may define genes acting between lesion formation and SA accumulation. Importantly, lesion mimic mutants generally have greatly reduced vigor, and cpr1, cpr5, and cpr6 plants are dwarf, indicating that constitutive expression of defense responses may not be the best strategy for improving disease resistance in crops.

An Arabidopsis gene that has been variously named NPR1, NIM1, and SAI1, is required for SA-mediated disease resistance. SA treatment of npr1/nim1 /sai1 mutants does not activate expression of PR-1, PR-5, or BGL2. When infected with a pathogen that induces SAR in wild-type plants, npr1/nim1/sai1 mutants accumulate high levels of SA, but do not develop SAR, indicating that NPR1/NIM1/SAI1 acts downstream from SA. However, NPR1/NIM1/SAI1 is not required for camalexin synthesis, so the effect of SA on camalexin synthesis must be mediated by some other, as yet unknown, factor. Plants with npr1/nim1/sai1 mutations display enhanced susceptibility to virulent pathogens, demonstrating that signal transduction downstream from NPR1/NIM1/SAI1 is important for restricting virulent pathogens as well as for SAR. NPR1/NIM1/SAI1 was recently cloned and shown to encode a protein containing ankyrin repeats.

Improving plant germplasm for increased resistance to disease is an agronomic goal of a high priority. Plants better able to respond to disease challenge in general, and via timely SA-induced phytoalexin synthesis in particular, are desirable.

A problem with the prior art is that genes available for use in genetic transformation to improve regulation of SA-mediated defense responses in plants are not numerous. As a result, efforts to improve plant germplasm for increased resistance to disease have been hampered. A challenge for genetic engineering has been to develop plants that can express disease defense responses without deleterious side effects. The present invention seeks to overcome this and other drawbacks inherent in the prior art.

ABBREVIATIONS

ABRC: Arabidopsis Biological Resource Center
ASA1: protein encoded by anthranilate synthase gene ASA1
ATCC: American Type Culture Collection
BAC: bacterial artificial chromosome
BGL2: protein encoded by β-glucanase gene BGL2
CAPS: cleaved amplified polymorphic sequence
CSPD Disodium 3-(4-methoxyspiro{1,2-dioxetane-3,2'-(5'-chloro)tricyclo[3.3.1.1$^{3.7}$]decan}-4-yl)phenyl phosphate
Col: Columbia ecotype
HR: hypersensitive response
JA: jasmonic acid
Ksk: Keswick ecotype
Ler: Landsberg erecta ecotype
NMD: nonsense mediated mRNA decay
PAD4: gene encoding wild-type PAD4 protein
PAD4: wild-type protein
pad4-1: gene encoding mutant pad4-1 protein
pad4-2: gene encoding mutant pad4-2 protein
pad4-3: gene encoding mutant pad4-3 protein
pad4-4: gene encoding mutant pad4-4 protein
PCR: polymerase chain reaction
PR-1: protein encoded by pathogenesis-related gene PR-1
PR-5: protein encoded by pathogenesis-related gene PR-5
Psm: *Pseudomonas syringae* pv *maculicola*
Pst: *Pseudomonas syringae* pv *tomato*
RACE: Random Amplified cDNA End
RFLP: Restriction Fragment Length Polymorphism
SA: salicylic acid
SAG: salicylic acid glucoside
SAR: systemic acquired resistance
YAC: yeast artificial chromosome

SUMMARY OF THE INVENTION

The present invention provides PAD4 compositions, and methods for using PAD4 compositions for enhancing disease resistance of a plant. PAD4 plays an important role in disease resistance since pad4 mutants show enhanced susceptibility to pathogen attack. Pathogens that show more extensive growth on pad4 plants than on wild-type plants include virulent strains of the bacterial pathogen *Pseudomonas syringae,* and avirulent and virulent isolates of the oomycete pathogen *Peronospora parasitica,* for example. Characterization of pad4 mutants, as provided herein, demonstrated that PAD4 acts by activating expression of defense mechanisms in response to pathogen attack. Additional analysis of SA and pathogen-induced PAD4 expression in pad4 mutants, also as provided herein, evidenced that PAD4 and SA act in a positive signal amplification loop required for activation of defense responses. The present inventors determined the nucleotide sequence of over 11,000 bp of DNA adjacent to and including the gene encoding PAD4, and provide herein nucleic acid and protein sequences for compositions for improving disease resistance in plants.

Table 1 of the Detailed Description infra provides identification of sequences having sequence identifiers for the present invention.

In particular, the invention provides a purified nucleic acid molecule comprising a sequence of nucleotides encoding a PAD4 polypeptide, the PAD4 polypeptide having an amino acid sequence essentially as set forth in SEQ ID NO. 2, or SEQ ID NO. 55.

In a further embodiment, the invention provides a purified nucleic acid molecule having a nucleotide sequence selected from the group consisting of:

a) the nucleotide sequence essentially set forth as SEQ ID NO.:1 or SEQ ID NO.:54;

b) the nucleotide sequence essentially set forth as SEQ ID NO.:3, SEQ ID NO.: 56, SEQ ID NO.: 58, SEQ ID NO.:60, or SEQ ID NO.:62;

c) the nucleotide sequence essentially set forth as SEQ ID NO.:5;

d) a nucleotide sequence encoding part or all of a polypeptide having an amino acid sequence essentially set forth as SEQ ID NO.: 2 or SEQ ID NO.: 55;

e) a nucleotide sequence that, through degeneracy of the genetic code, encodes part or all of essentially the same polypeptide as that encoded by the nucleotide sequence of any of a)–d);

f) a nucleotide sequence that is the complement of any of a)–e); and g) a nucleotide sequence that hybridizes to any of a)–f) under conditions of predetermined stringency.

Another embodiment of the invention is an oligonucleotide molecule comprising a nucleotide sequence between 20 and 100 nucleotides in length, the molecule hybridizing under conditions of predetermined stringency with a portion of an above-named nucleic acid molecule.

Nucleic acid molecules of the invention are derived from any plant species, including, without limitation, angiosperms (for example, dicots and monocots) and gymnosperms. Exemplary plants from which the nucleic acid may be derived, and into which the nucleic acid may be introduced as a transgene, include, for example, plants such as sugar cane, wheat, rice, maize, sugar beet, potato, barley, manioc, sweet potato, soybean, sorghum, cassava, grape, oats, millet, rye, watermelon, canola, garlic, strawberry, bean, mango, alfalfa, apple, banana, coffee, oil seed Brassica, coconut, cotton, sunflower, olive, papaya, peanut, safflower, sesame, flax, palm, arugula, asparagus, artichoke, edible beans, beet, broccoli, brussel sprouts, cabbage, carrot, cauliflower, celery, cilantro, cucumber, eggplant, endive, horseradish, lettuce, okra, onion, parsnip, pea, hot pepper, sweet pepper, pumpkin, radish, spinach, squash, sweet corn, sweet potato, swiss chard, tomato, turnip, yam, or zucchini. Preferred nucleic acid molecules are derived from cruciferous plants, for example, Arabidopsis thaliana. An example of such a cruciferous nucleic acid molecule is provided as SEQ ID NO.:1, SEQ ID NO.:3, SEQ ID NO.:54, SEQ ID NO.: 56, SEQ ID NO.: 58, SEQ ID NO.:60, or SEQ ID NO.:62, or SEQ ID NO.:5. In a preferred embodiment, the purified nucleic acid molecule as described herein is from Arabidopsis.

The invention also provides a purified protein comprising a sequence of amino acids, the protein having positive regulatory effect on phytoalexin levels and on PR-1 expression levels while having substantially no regulatory effect on PR-5, BGL2, or ASA1 expression levels in a disease defense response by a host plant. The invention further provides a purified protein comprising a sequence of amino acids, the protein having positive regulatory effect on its own expression levels, on phytoalexin levels, and on PR-1 expression levels while having substantially no regulatory effect on PR-5, BGL2, or ASA1 expression levels in a disease defense response by a host plant. Such protein may be obtained from any plant species, for example, those plants listed herein. In preferred embodiments, the protein is derived from a cruciferous species, for example, Arabidopsis thaliana, or from a solanaceous species, for example, Nicotiana glutinosa. In a further preferred embodiment, the protein comprises an amino acid sequence essentially as set forth in SEQ ID NO.: 2 or SEQ ID NO.: 55. A purified protein produced by expression of an above-described nucleic acid molecule in an expression vector is a further aspect of the invention.

In a related embodiment, the invention further provides a recombinant vector comprising a purified nucleic acid molecule as described herein. The recombinant vector may be an expression vector comprising a regulatory element for expression of PAD4 in plant cells. In a preferred embodiment, the purified nucleic acid molecule of the invention is operably linked to an expression control region that mediates expression of a polypeptide encoded by the nucleic acid molecule. For example, the expression control region is capable of mediating constitutive, inducible (for example, pathogen- or wound-inducible), or cell- or tissue-specific gene expression.

A recombinant host cell comprising a nucleic acid molecule as described herein and a recombinant host cell comprising a recombinant vector as described herein are also aspects of the present invention. In preferred embodiments, the recombinant host cell is a bacterium (for example, E. Coli or Agrobacterium tumefaciens) or is a plant cell (for example, a cell from any of the plants listed herein). Such a plant cell transformed with and expressing a gene encoding PAD4 has an increased level of resistance against disease, in particular, a disease caused by a plant pathogen (for example, Phytophthora, Peronospora, or Pseudonomas). In one embodiment, the gene encoding PAD4 is heterologous to the plant cell. Preferably, the heterologous gene is integrated into the plant genome.

In another embodiment, the invention provides a plant comprising a transgene expressing PAD4, thereby providing enhanced disease resistance to the plant. Preferably, the transgene is integrated into the genome of the plant, wherein the nucleic acid molecule is expressed in the transgenic plant. The transgene may be heterologous or homologous. In addition, the invention provides progeny, seeds, or clones of such transgenic plants. Such transgenic plants may be produced according to conventional methods using any of the plants listed supra.

A purified antibody having binding specificity for an antigenic region of PAD4 or PAD4 is a further aspect of the invention.

In another aspect, the invention provides a method of using a nucleic acid molecule as provided herein, the method comprising: preparing a recombinant vector in which the nucleic acid molecule is positioned under the control of a promoter; introducing the recombinant vector into a host cell; culturing the host cell under conditions effective to allow expression of the encoded polypeptide; and collecting the expressed polypeptide. A recombinant protein produced by such a method is a further aspect of the present invention.

A method for enhancing resistance of a plant to disease comprising providing to the plant an amount of PAD4 effective to enhance resistance to disease is provided herein. The method may comprise producing a transgenic plant cell including a nucleic acid molecule encoding PAD4, wherein the nucleic acid molecule is positioned for expression in the plant cell; and growing a transgenic plant from the plant cell; wherein the nucleic acid molecule is expressed in the transgenic plant to produce PAD4, thereby providing an increased level of resistance to disease. The disease may be due to a pathogen selected from the group consisting of a bacterium, virus, viroid, fungus, oomycete, nematode, or insect. In particular, the disease may be due to infection by Phytophthora, Peronospora, or Pseudomonas.

The present invention provides a method of determining presence of target nucleic acid in a test plant cell, comprising: contacting a nucleic acid molecule as provided herein, or a portion thereof, with a preparation of nucleic acid from the test plant cell under hybridization conditions of predetermined stringency; and assessing hybridization of the nucleic acid molecule in the preparation, wherein when hybridization occurs under conditions of predetermined stringency, target nucleic acid is present in the test plant cell. The method may further comprise the step of isolating the target nucleic acid.

The present invention provides a further method of determining presence of target nucleic acid in a test plant cell comprising: providing a sample of test plant cell nucleic acid; contacting at least one oligonucleotide having sequence identity to a region of the nucleic acid of SEQ ID NO.:1 or SEQ ID NO.:54 with the test plant cell nucleic acid under conditions suitable for nucleic acid amplification; amplifying the nucleic acid; and determining presence of target nucleic acid by presence of amplified nucleic acid. The method may further comprise the step of isolating the amplified target nucleic acid.

A method of producing a transgenic plant, comprising incorporating a nucleic acid molecule as described herein into a plant cell and generating a transgenic plant from the plant cell is a further embodiment of the invention.

A further aspect of the present invention is a method for enhancing resistance of a plant to disease comprising providing to the plant an amount of a nucleic acid molecule effective to enhance resistance to disease, the nucleic acid molecule comprising a sequence of nucleotides encoding a factor, the factor having a positive regulatory effect on phytoalexin levels and on PR-1 expression levels while having substantially no regulatory effect on PR-5, BGL2, or ASA1 expression levels in a disease defense response by a host plant. An additional aspect of the present invention is a method for enhancing resistance of a plant to disease comprising providing to the plant an amount of a nucleic acid molecule effective to enhance resistance to disease, the nucleic acid molecule comprising a sequence of nucleotides encoding a factor, the factor having a positive regulatory effect on its own expression levels, on phytoalexin levels, and on PR-1 expression levels while having substantially no regulatory effect on PR-5, BGL2, or ASA1 expression levels in a disease defense response by a host plant. In a preferred embodiment, the factor is PAD4. In a further preferred embodiment, the nucleic acid molecule has a nucleotide sequence essentially as set forth as SEQ ID NO.:5. In another further preferred embodiment, the purified protein comprising a sequence of amino acids having a positive regulatory effect on phytoalexin levels and on PR-1 expression levels while having substantially no regulatory effect on PR-5, BGL2, or ASA1 expression levels in a disease defense response by a host plant is an esterase or a lipase.

The major features of the plant defense response that have been observed in crop plants have also been observed in Arabidopsis-pathogen interactions. For example, several resistance gene-avirulence gene interactions have been identified for both bacterial and fungal pathogens of Arabidopsis. Further, the important features of systemic acquired resistance have been observed in Arabidopsis. Arabidopsis genetic analysis has been used to help identify a variety of components of the Arabidopsis defense response to pathogen attack. Thus, the invention as provided herein provides the basis for identifying PAD4 genes that are involved in disease resistance throughout the plant kingdom and are not limited to Arabidopsis.

PAD4 compositions of the present invention provide a number of important advances and advantages for the protection of plants against their pathogens and against environmental stress. For example, by providing PAD4 genes as described herein that are readily incorporated and expressed in all species of plants, the invention facilitates an effective and economical means for in-plant protection against plant disease. Such protection against disease reduces or minimizes the need for traditional chemical practices (for example, application of fungicides, bactericides, nematicides, insecticides, or viricides) that are typically used by farmers for controlling the spread of plant pathogens and providing protection against disease. In addition, because plants expressing a PAD4 gene described herein are less vulnerable to pathogens and their diseases, the invention further provides for increased production efficiency, as well as for improvements in quality and yield of crop plants and ornamentals. Thus, the invention contributes to the production of high quality and high yield agricultural products: for example, fruits, ornamentals, vegetables, cereals and field crops having reduced spots, blemishes, and blotches that are caused by pathogens; agricultural products with increased shelf-life and reduced handling costs; and high quality and yield crops for agricultural (for example, cereal and field crops), industrial (for example, oilseeds), and commercial (for example, fiber crops) purposes. Furthermore, because the invention reduces the necessity for chemical protection against plant pathogens, the invention benefits the environment where the crops are grown. Genetically-improved seeds and other plant products that are produced using plants expressing the genes described herein also render farming possible in areas previously unsuitable for agricultural production.

The invention is also useful for providing nucleic acid and amino acid sequences of a PAD4 gene that facilitates the isolation and identification of PAD4 genes, as well as the isolation and identification of genes related to PAD4 genes (such as mutant alleles or PAD4-like pseudogenes), from any plant species. In particular, all or a portion of nucleic acid molecules having the nucleotide sequence essentially set forth as SEQ ID NO.:1, SEQ ID NO.:3, SEQ ID NO.: 54, SEQ ID NO.:56, SEQ ID NO.:58, SEQ ID NO.:60, or SEQ ID NO.:62, or having a nucleotide sequence complementary to such a nucleotide sequence, may be used as probes for the isolation and identification of PAD4 genes, as well as the isolation and identification of genes related to PAD4 genes (such as mutant alleles or PAD4-like pseudogenes), from any plant species. The nucleic acid and protein molecules of the present invention have further utility as molecular weight markers for separation procedures using gels and chromatography columns, for example; and fragments of nucleic acids are useful as probes and primers, for example, especially those having greater than 50% G+C content.

Other features and advantages of the invention will be apparent from the following description of the preferred embodiments thereof, and from the claims.

Following long-standing patent law convention, the terms "a" and "an" mean "one or more" when used in this application, including the claims. Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Infection with *P. s. maculicola* ES4326 or *P. s. maculicola* ES4326 Carrying avrRpt2.

▨ wt-Psm, wild-type plants infected with *P. s. maculicola* ES4326;

■ pad4-Psm, pad4-1 plants infected with *P. s. maculicola* ES4326;

☒ wt-avr, wild-type plants infected with *P. s. maculicola* ES4326 carrying avrRpt2;

◨ pad4-avr, pad4-1 plants infected with *P. s. maculicola* ES4326 carrying avrRpt2.

Figure 1A:
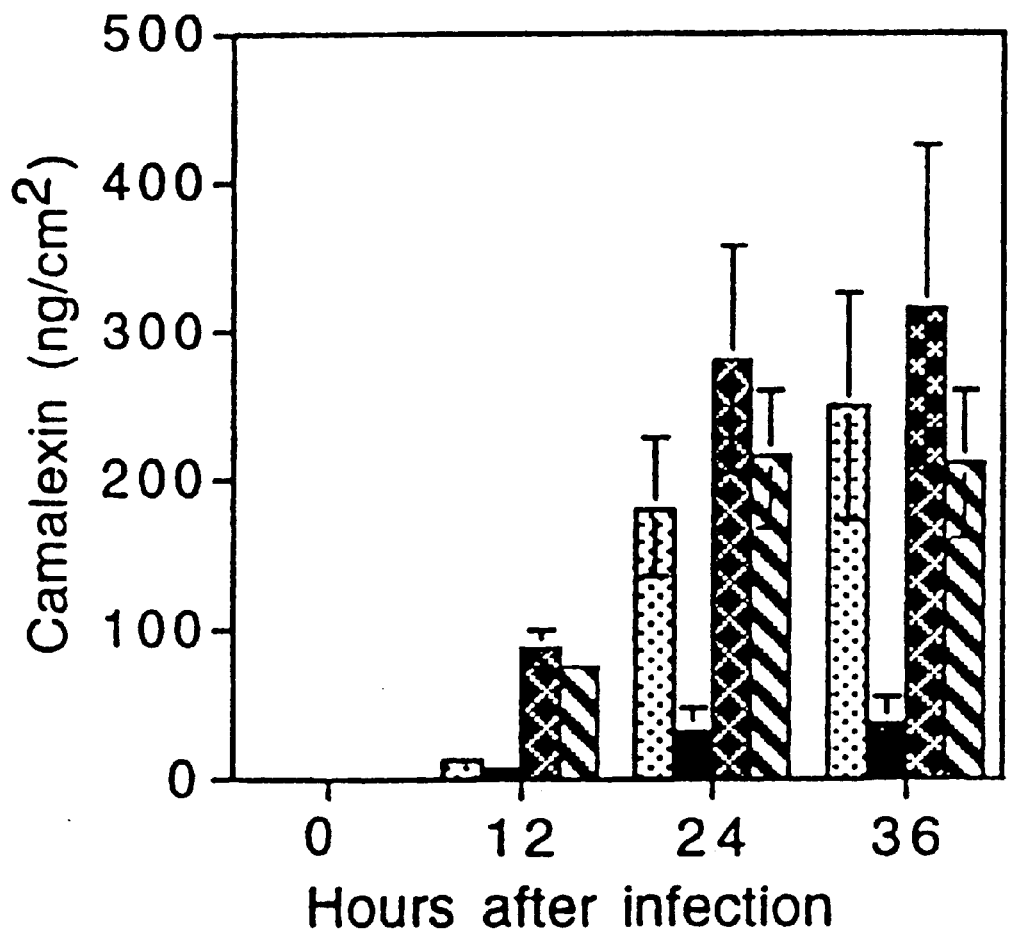
FIGS. 1A–1C. Camalexin Levels in Wild-Type and pad4-1 Plants after Various Treatments.
Figure 1B:
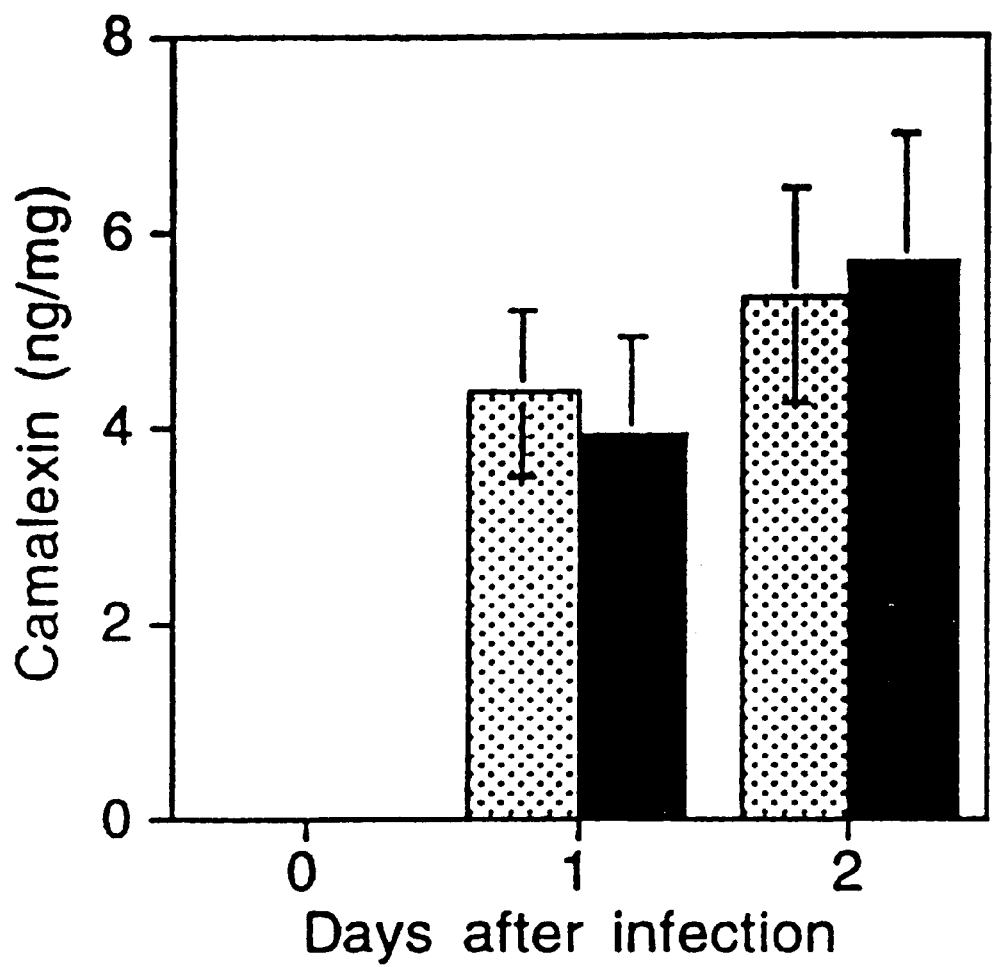

FIG. 1B. Infection with *X. c. campestris* BP109.

▨ wt;

■ pad4-1.

Figure 1C:
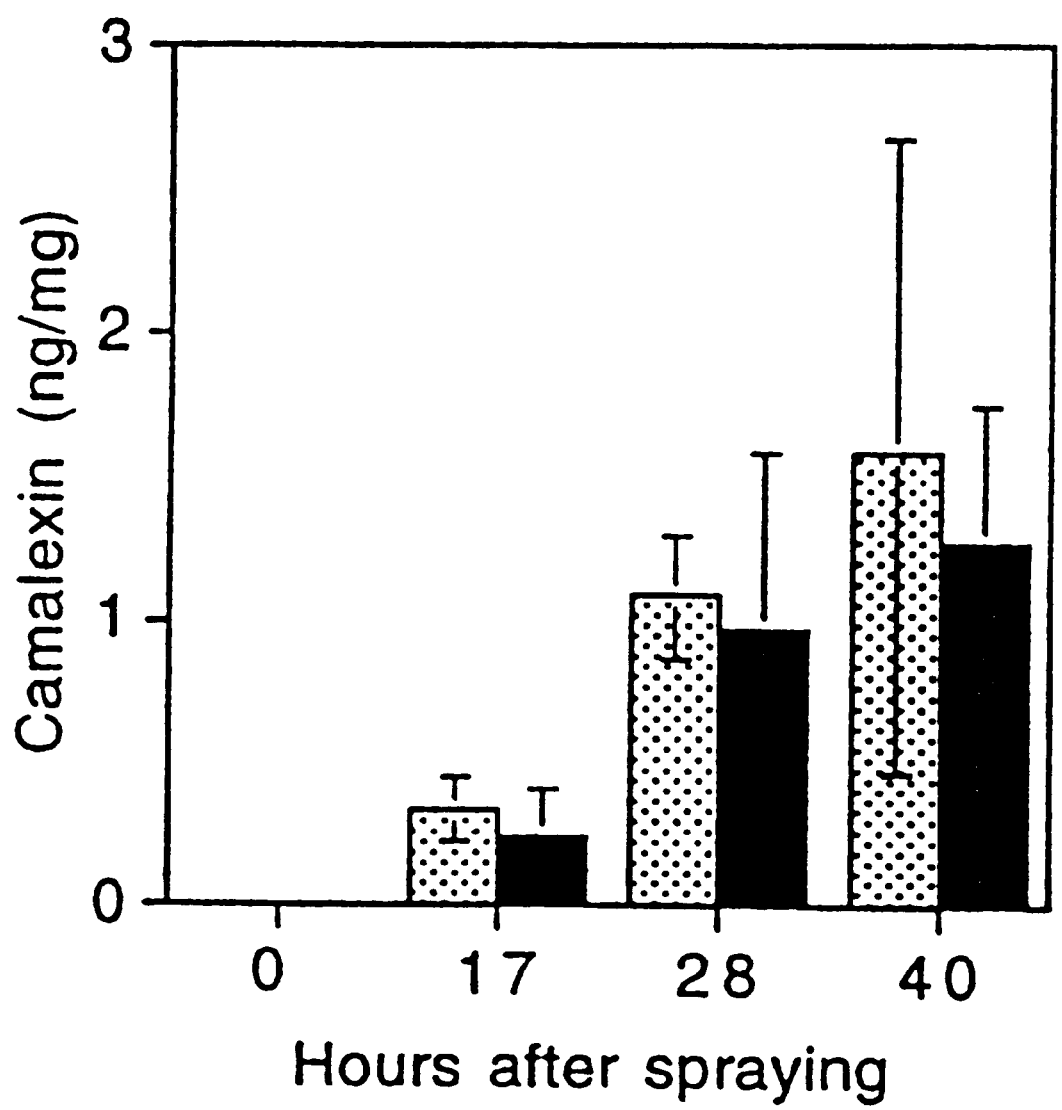

FIG. 1C. Spraying with 5 mM Silver Nitrate.

▨ wt;

■ pad4-1.

Figure 2A:
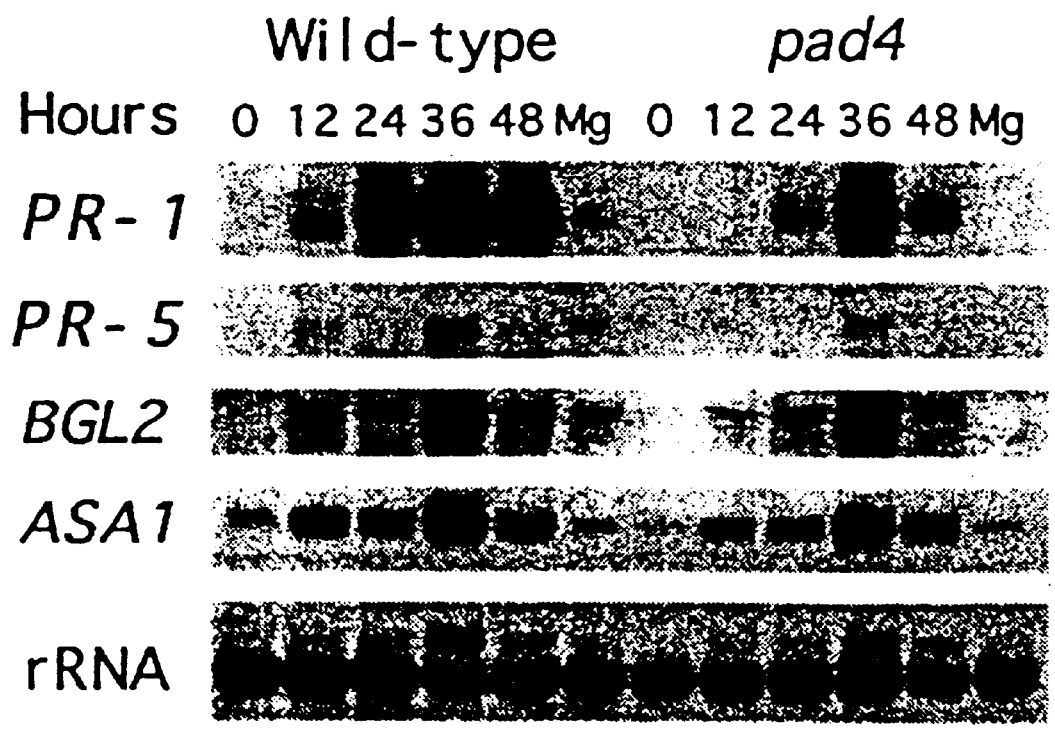
Figure 2B:
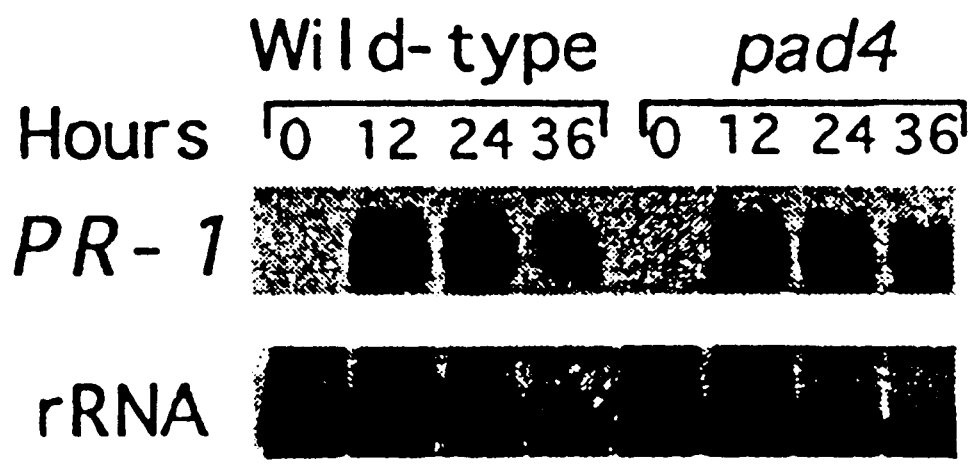

FIGS. 2A–2B. Defense Gene Expression in Leaves Infected with *P. s. maculicola* ES4326 or *P. s. maculicola* ES4326 Carrying avrRpt2. Leaves were excised at 0, 12, 24, 36, or 48 hours after infection. Mg indicates leaves mock-inoculated with 10 mM MgSO$_4$ sampled at 36 hours. rRNA indicates hybridization with an 18S rRNA probe, used to evaluate equal loading.

FIG. 2A. Infection with *P. s. maculicola* ES4326.

FIG. 2B. Infection with *P. s. maculicola* ES4326 Carrying avrRpt2.

Figure 3A:
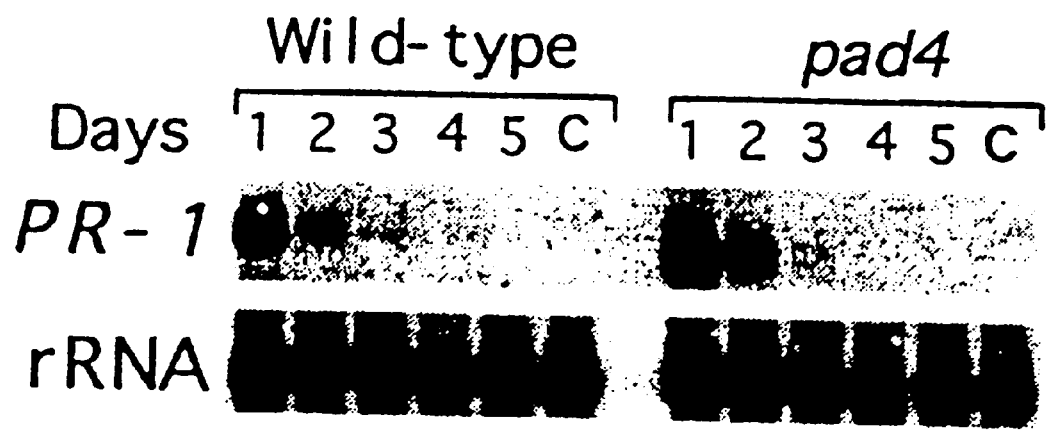
Figure 3B:
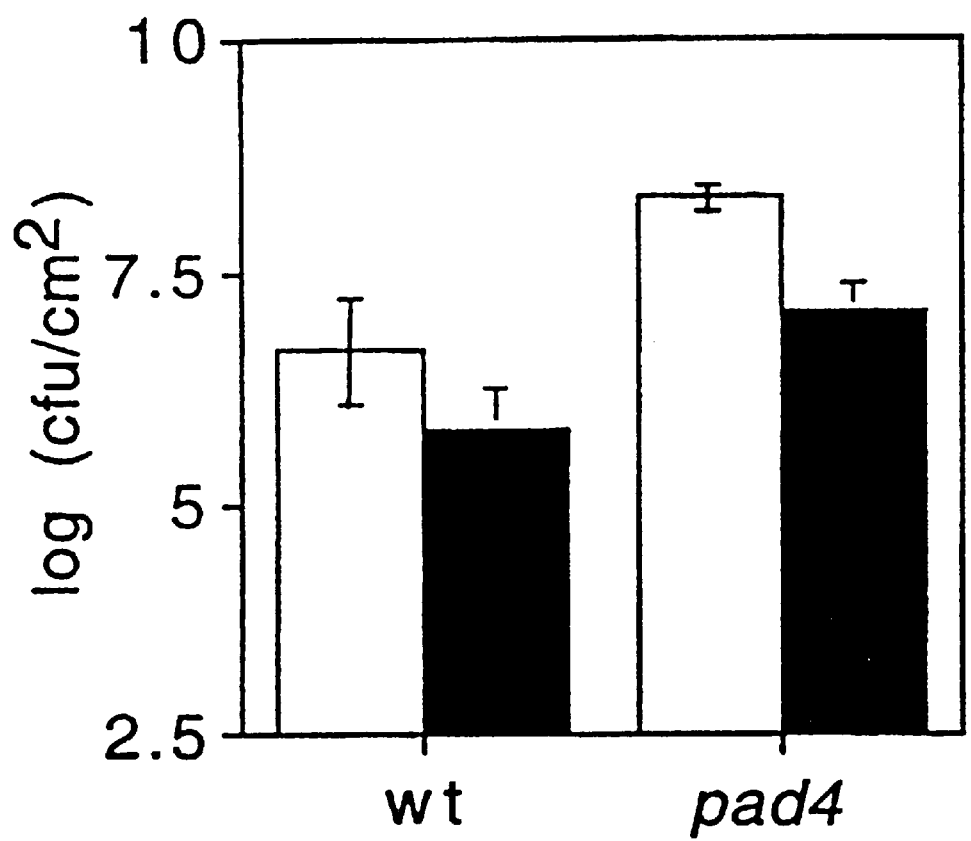

FIGS. 3A–3B. Exogenous SA Induces PR-1 Expression and Enhanced Resistance to *P. s. maculicola* ES4326 in Wild-Type and pad4-1 Plants. Plants were sprayed with 5 mM SA in 0.02% (v/v) Silwet L-77 or with 0.02% Silwet alone until uniformly wet.

FIG. 3A. PR-1 Expression in Response to SA. Samples were taken daily after spraying. The "c" indicates control; plants were sprayed with 0.02% Silwet alone and sampled at 3 days after spraying.

FIG. 3B. Effect of Spraying Plants with SA on *P. s. maculicola* ES4326 Growth. One day after treatment, plants were infected with *P. s. maculicola* ES4326 at a dose of $10^3$ cfu/cm$^2$. Bacterial titer was determined 3 days after infection. Each bar represents the mean and standard deviation of eight replicates. Similar results were obtained in three other independent experiments.

☐ −SA, plants were not treated with SA prior to infection;

■ +SA, plants were treated with SA prior to infection.

Figure 4:
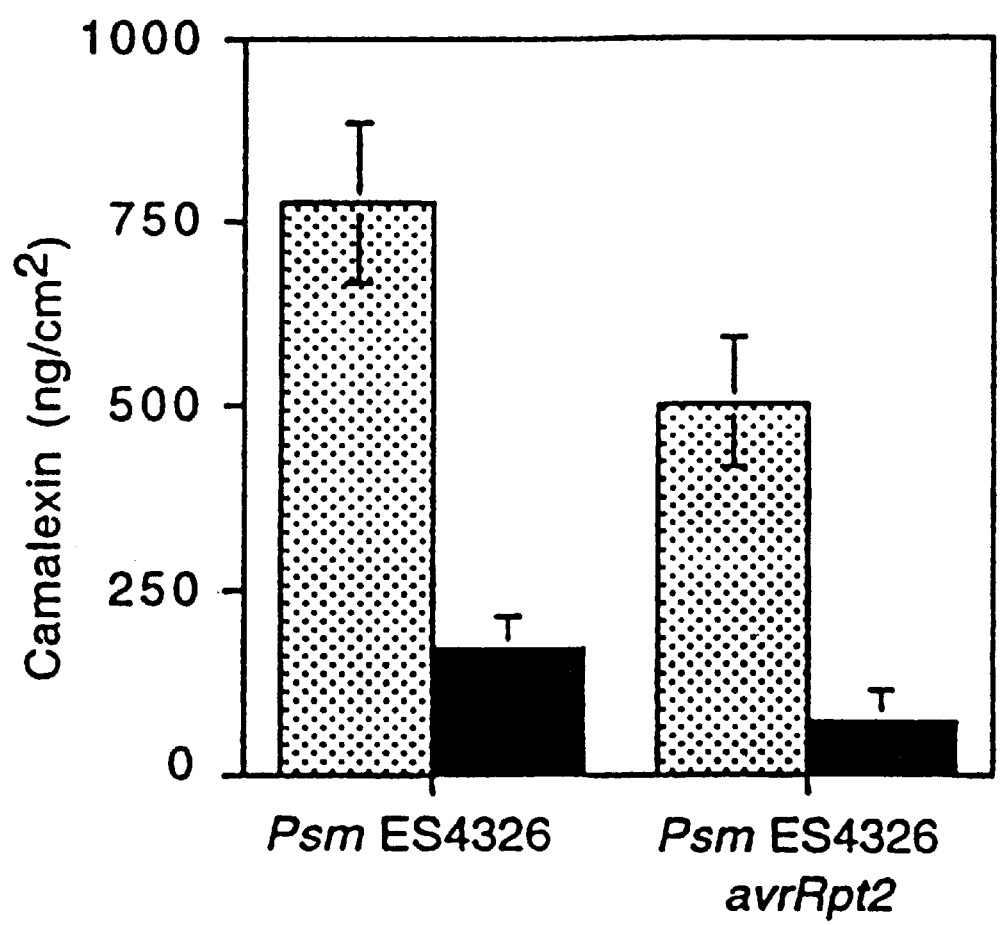

FIG. 4. Camalexin Accumulation in Wild-Type and nahG Plants Infected with Pathogens. Wild-type Ler and Ler nahG transgenic plants were infected with either *P. s. maculicola* (Psm) ES4326 or *P. s. maculicola* ES4326 carrying avrRpt2 at a dose of $10^5$ cfu/cm$^2$. Camalexin in the infected leaves was determined at the times that camalexin levels arc high in wild-type plants: 24 hr after infection for *P. s. maculicola* ES4326 carrying avrRpt2 and 32 hr after infection for *P. s. maculicola* ES4326. Each bar represents the mean and standard deviation of eight replicate samples.

▨ wt;

☐ nahG.

FIGS. 5A–5D. SA and SAG Levels in infected Wild-type and pad4-1 Plants. Wild-type (wt) and pad4-1 plants were infected with *P. s. maculicola* ES4326 (Psm), *P. s. maculicola* ES4326 carrying avrRpt2 (Psm avr), or mock-infected with 10 mM MgSO$_4$ (mock). Each column represents the mean of three replicate samples. Error bars representing the standard deviation are shown where they are large enough to be visible. SA and SAG were assayed on the same samples. The experiment with *P. s. maculicola* ES4326 and experiment with *P. s. maculicola* ES4326 carrying avrRpt2 were carried out at different times.

Figure 5A:
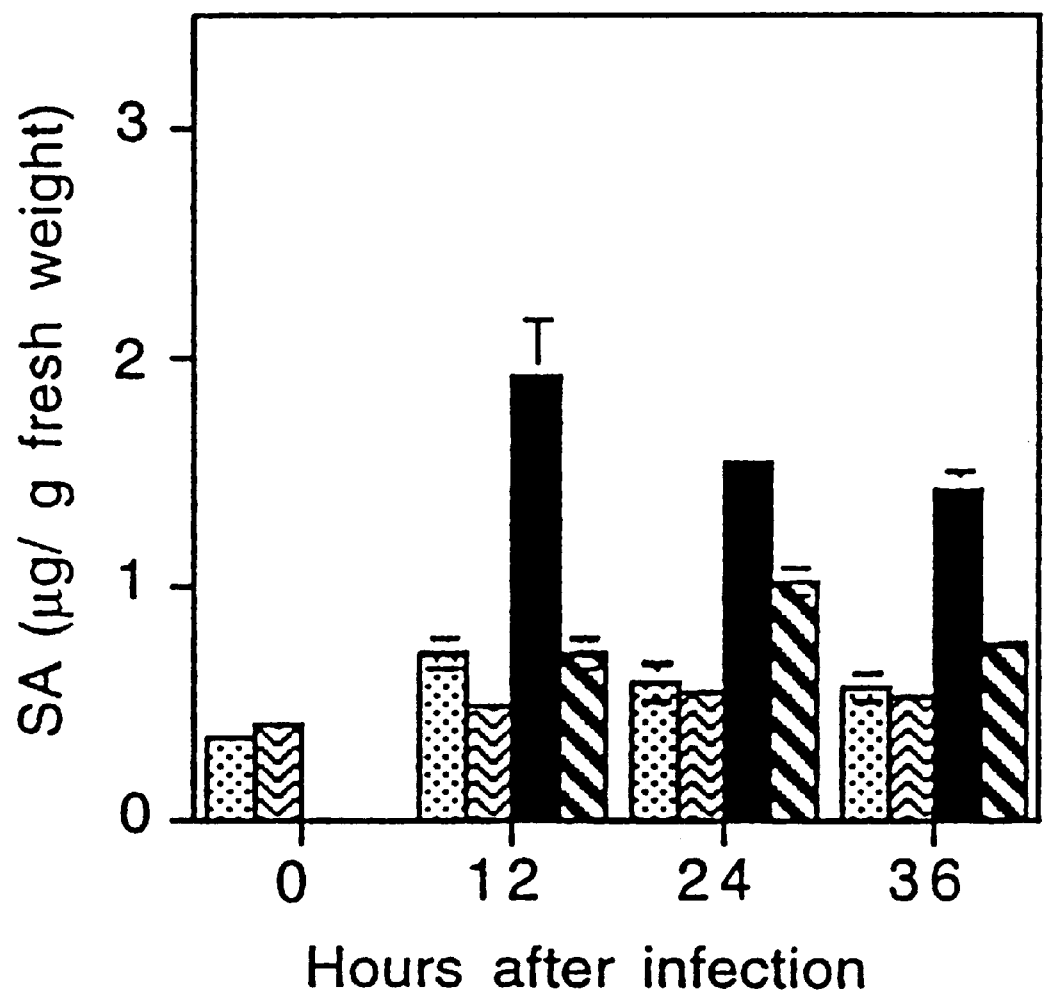

FIG. 5A. SA Levels in Plants Infected with *P. s. maculicola* ES4326.

▨ wt mock;

▨ pad4-1 mock;

■ wt Psm;

◩ pad4-1 Psm.

Figure 5B:
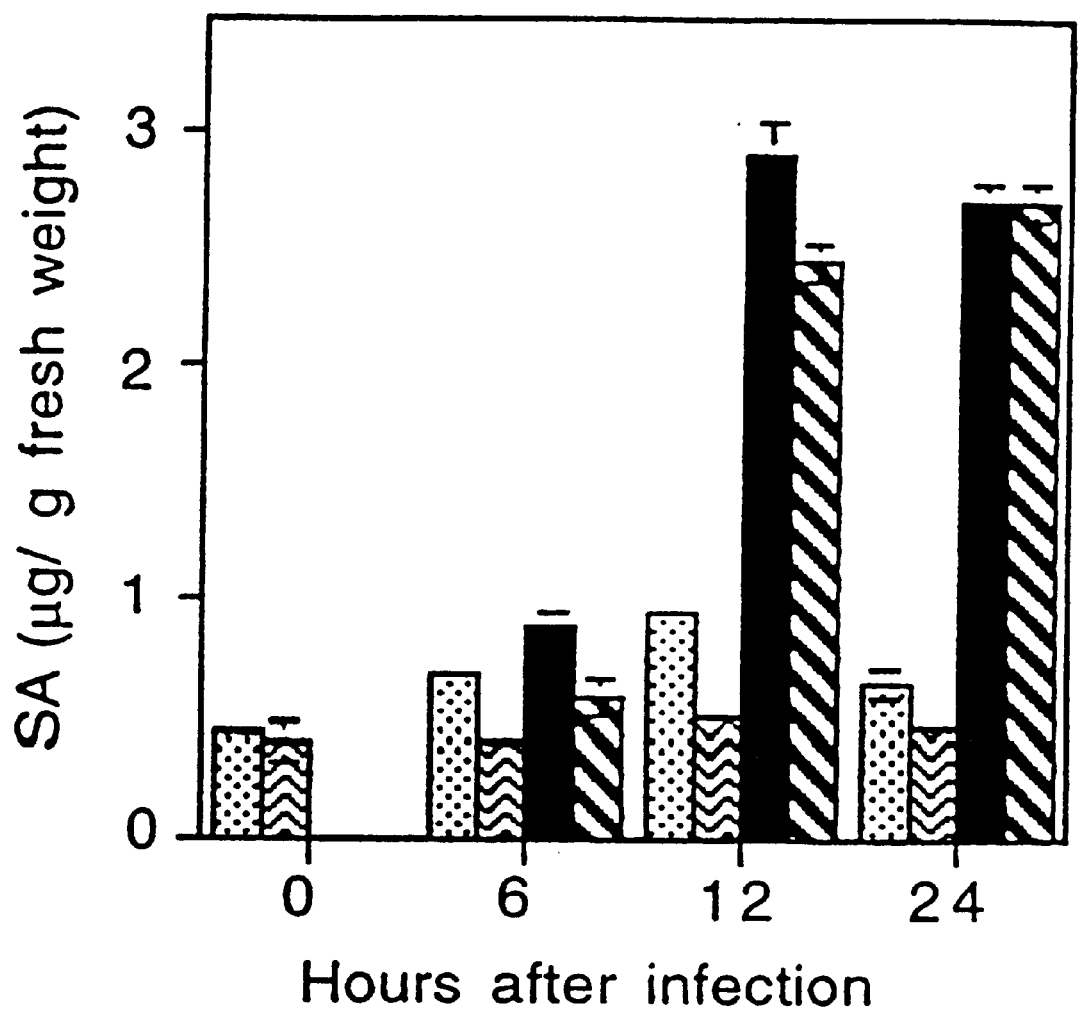

FIG. 5B. SA Levels in Plants Infected with *P. s. maculicola* ES4326 Carrying avrRpt2.

▨ wt mock;

▨ pad4-1 mock;

■ wt Psm avr;

◩ pad4-1 Psm avr.

Figure 5C:
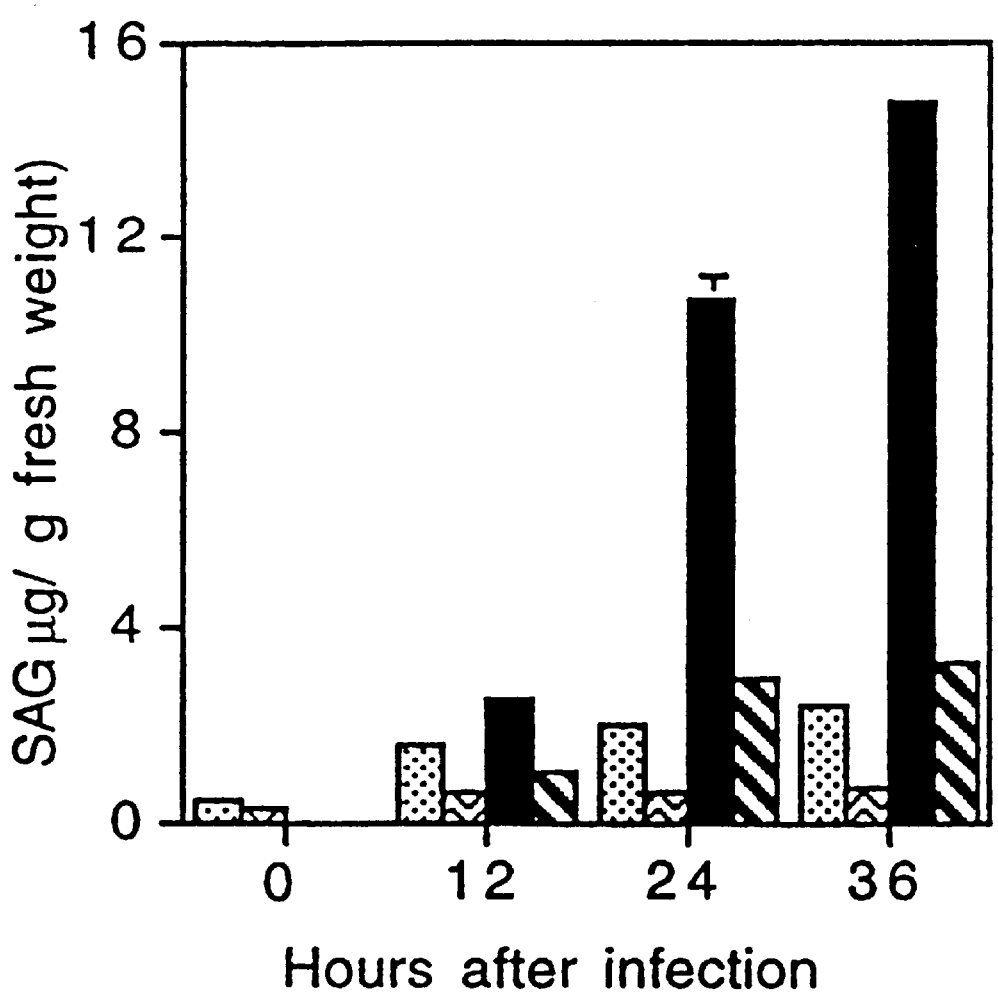

FIG. 5C. SAG levels in Plants Infected with *P. s. maculicola* ES4326.

▨ wt mock;

▨ pad4-1 mock;

■ wt Psm;

◩ pad4-1 Psm.

Figure 5D:
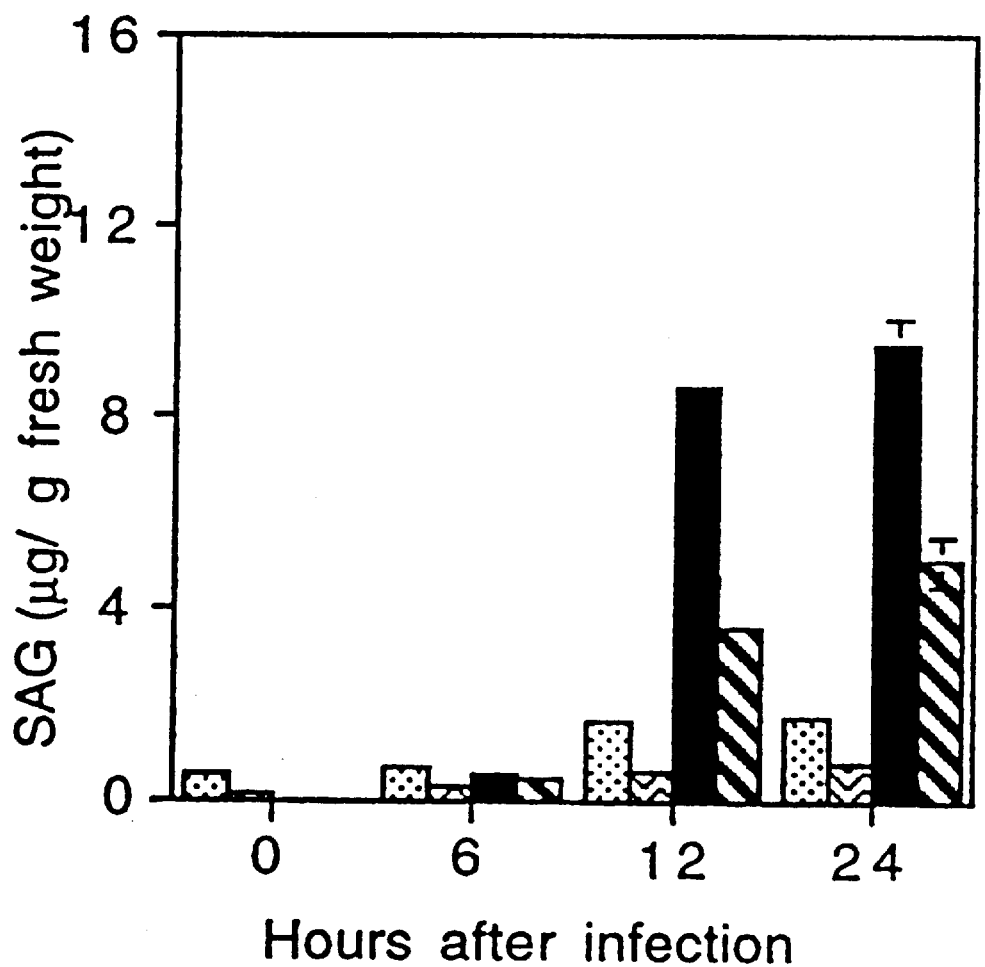

FIG. 5D. SAG Levels in Plants Infected with *P. s. maculicola* ES4326 Carrying avrRpt2.

▨ wt mock;

▨ pad4-1 mock;

■ wt Psm avr;

◩ pad4-1 Psm avr.

Figure 6A:
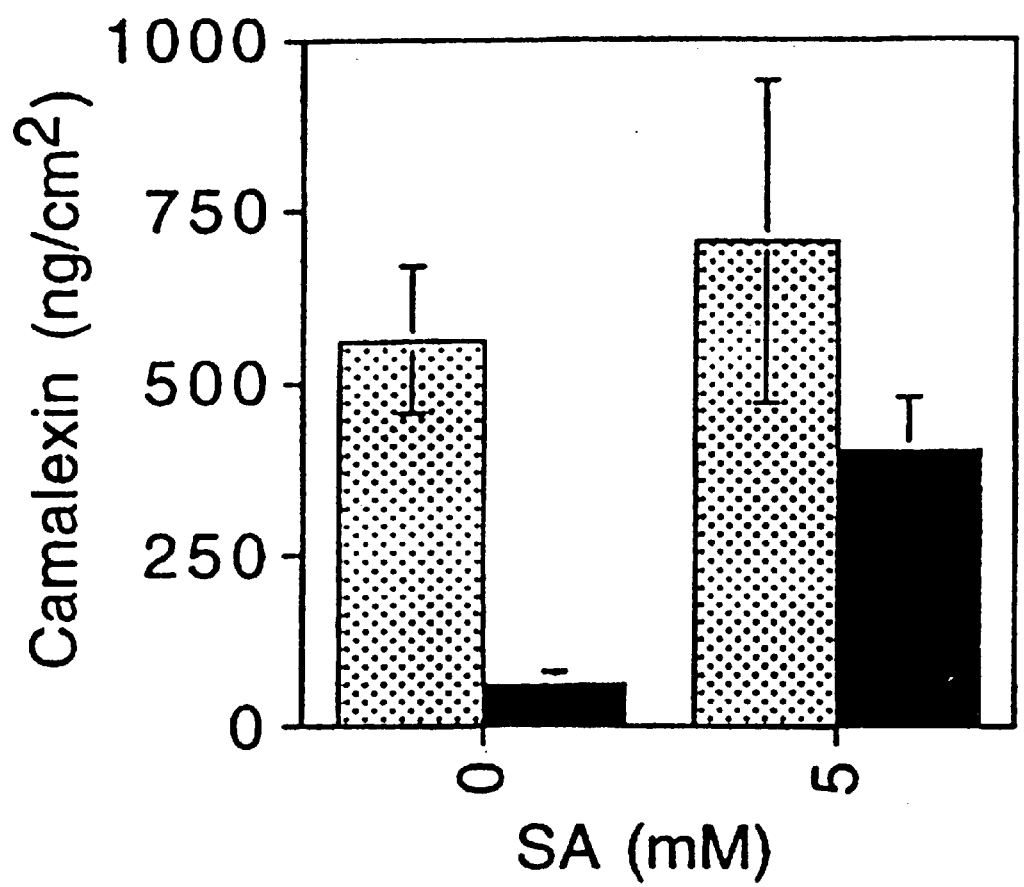
Figure 6B:
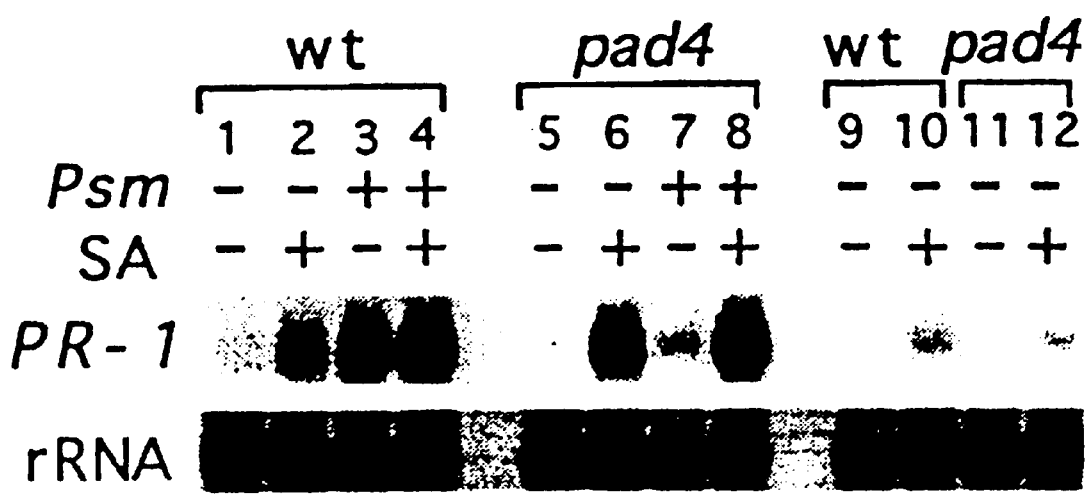

FIGS. 6A–6B. SA Application Prior to *P. s. maculicola* ES4326 Infection Restores Camalexin Accumulation and PR-1 Expression in pad4-1 Plants. Wild-type and pad4-1 plants were either treated with 5 mM SA in 0.02% (v/v) Silwet L-77, or with 0.02% Silwet alone, one day before infection with *P. s. maculicola* ES4326.

FIG. 6A. Effect of Exogenous SA on Camalexin Levels in *P. s. maculicola* ES4326-Infected Plants. Infected leaves were sampled 2 days after infection. Each data point represents the mean and standard deviation of six replicates.

▨ wt;

■ pad4-1.

FIG. 6B. Effect of Exogenous SA on PR-1 Expression in *P. s. maculicola* ES4326-Infected Plants. Leaves infected with *P. s. maculicola* ES4326 were sampled from mock-treated wild-type and pad4-1 plants (lanes 3 and 7) and SA-treated plants (lanes 4 and 8) 2 days after infection. For comparison, mock-treated plants were sampled 1 and 2 days after treatment (lanes 1 and 9, respectively, for wild-type, lanes 5 and 11, respectively, for pad4-1), as were SA-treated plants (lanes 2 and 10, respectively, for wild-type, lanes 6 and 12, respectively, for pad4-1). Similar results were obtained in another independent experiment. + and − in the row labeled SA indicate the presence or absence of SA treatment, respectively. + and − in the row labeled Psm indicate the presence or absence of *P. s. maculicola* ES4326 infection, respectively. Due to the strong PR-1 signal in leaves infected with *P. s. maculicola* ES4326, the exposure for this blot was shorter than the exposure for the blot shown in FIG. 3A; consequently, expression of PR-1 48 hours after SA treatment appears lower than it does in FIG. 3A.

Figure 7:
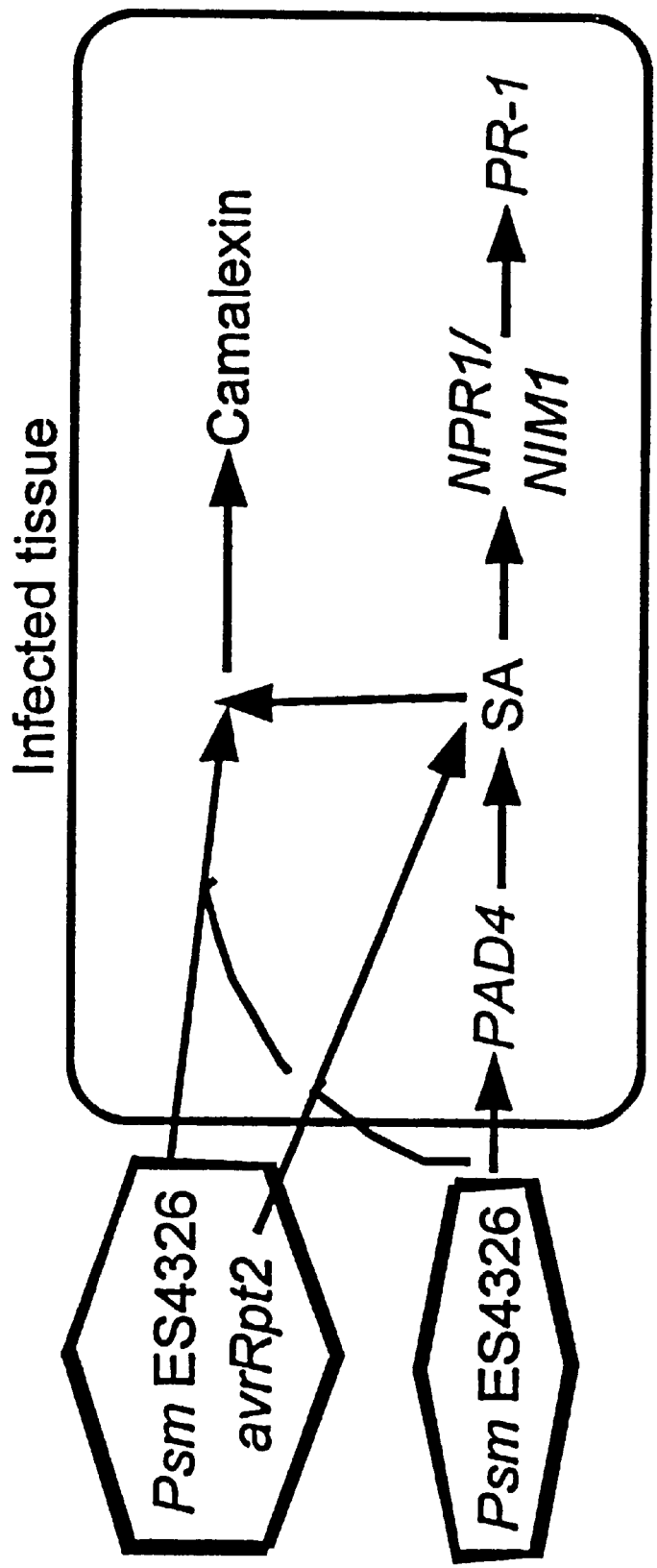

FIG. 7. Model for the Role of PAD4 in Signal Transduction. When plants are infected with *P. s. maculicola* (Psm) ES4326, PAD4 function is needed for SA accumulation and activation of defense responses that require SA, such as camalexin synthesis and PR-1 expression. When plants are infected with *P. s. maculicola* ES4326 carrying avrRpt2, SA accumulation occurs by a PAD4 independent mechanism, possibly an oxidative burst.

Figure 8:
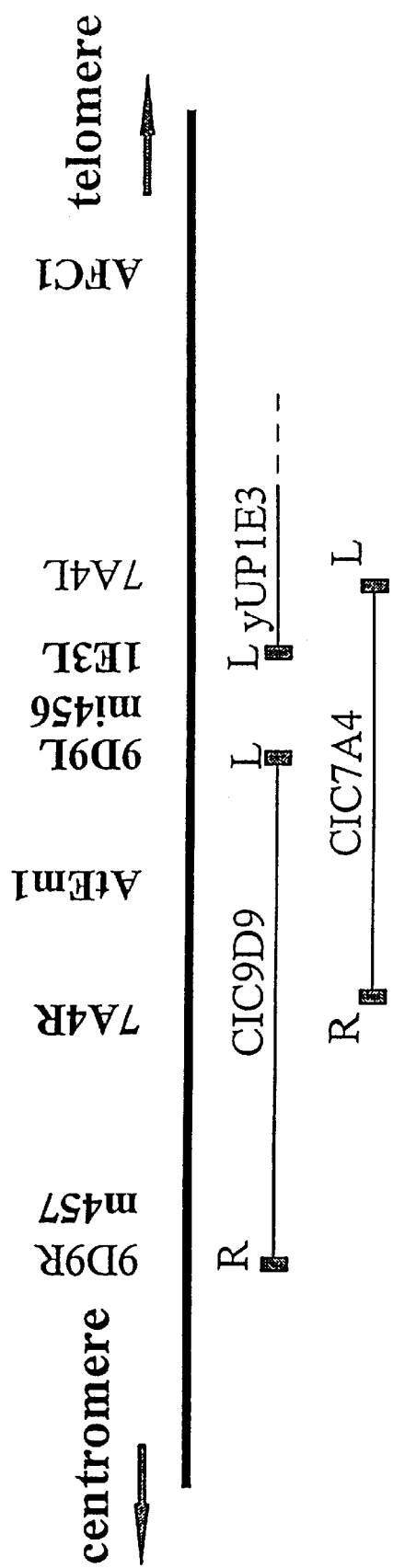

FIG. 8. YAC (Yeast Artificial Chromosome) Contig around Marker m457. Markers shown in bold face were used to map pad4-1. "R" and "L" refer to the right and left ends of YAC clones. According to convention, right and left are determined relative to the YAC vector, not the Arabidopsis chromosome. The map is not drawn to scale.

Figure 9:
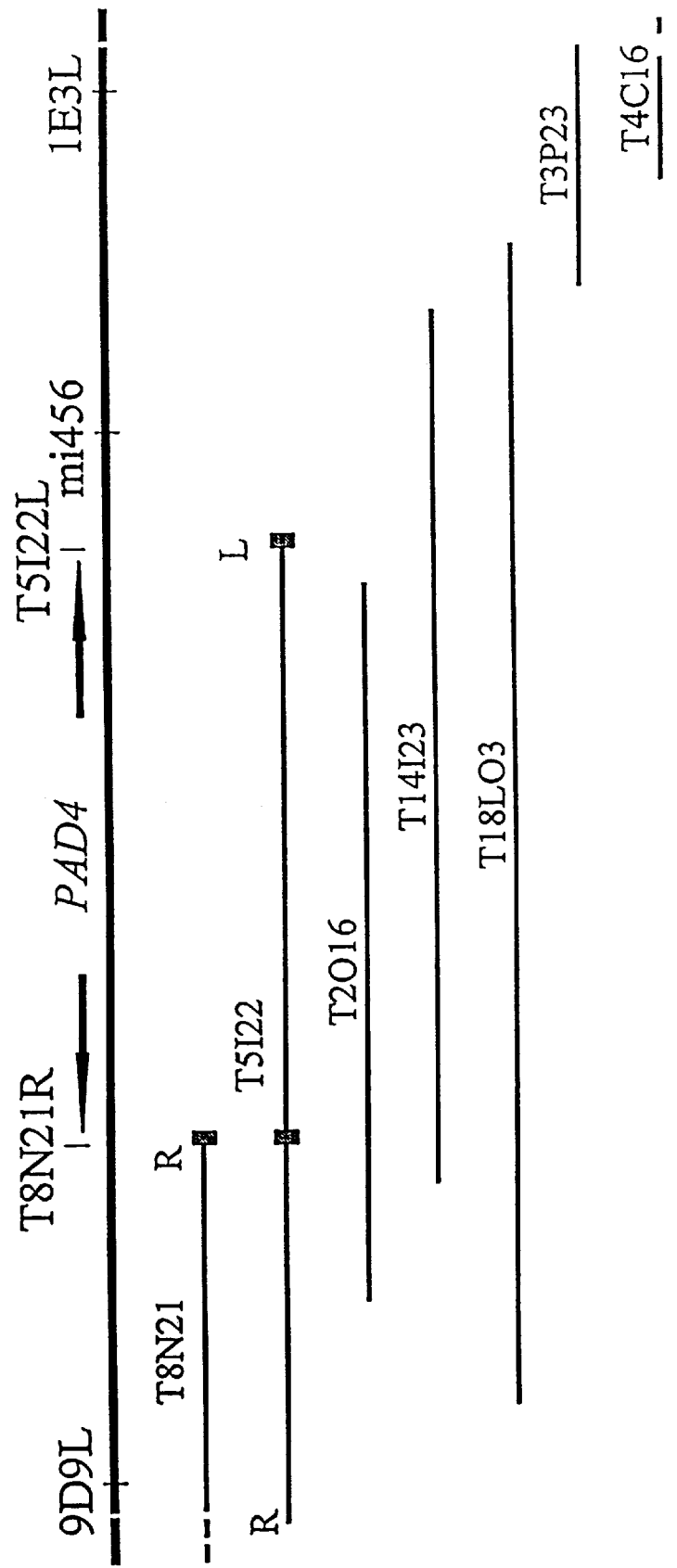

FIG. 9. BAC (Bacterial Artificial Chromosome) Clones in the PAD4 Region.

Figure 10B:
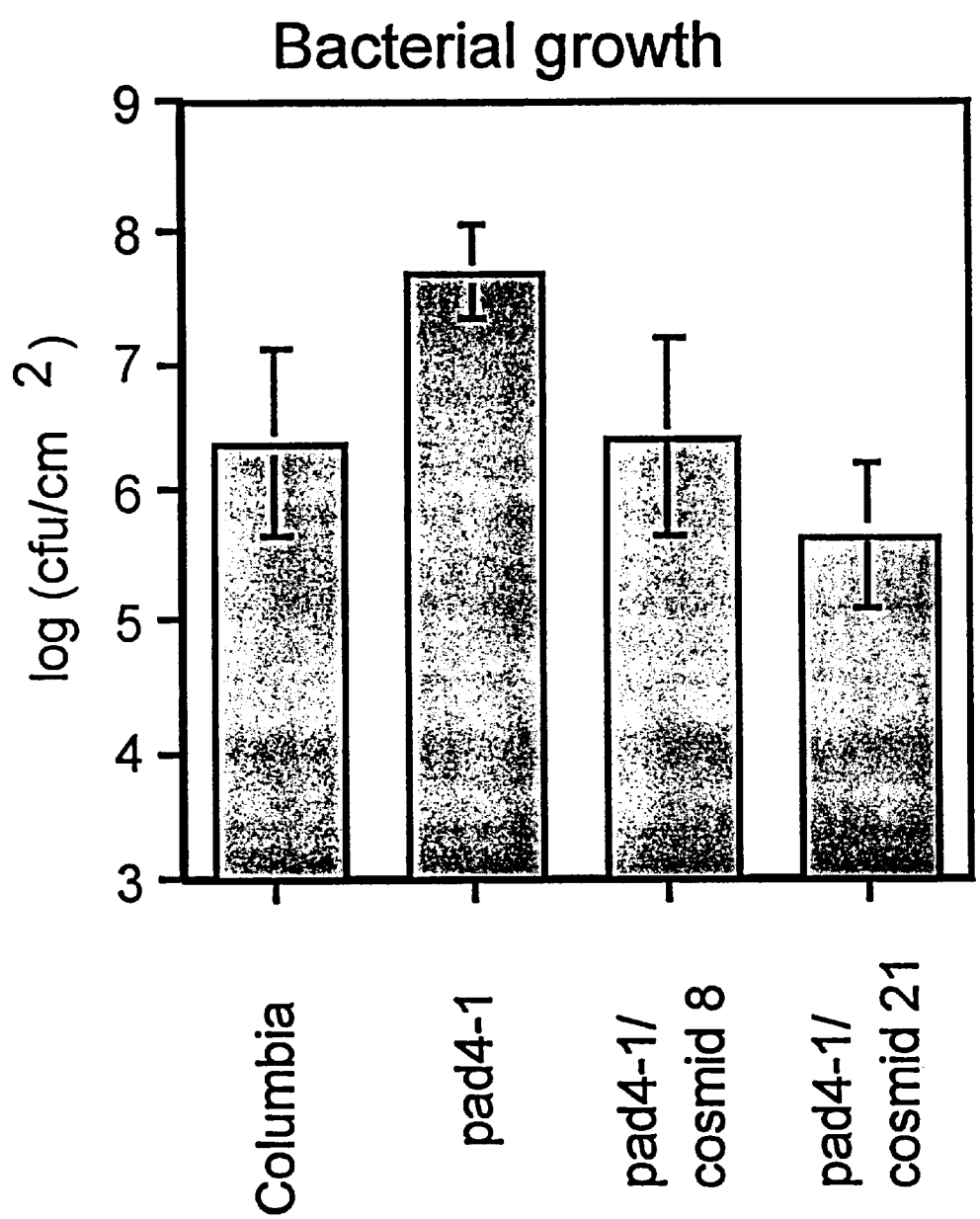
Figure 10C:
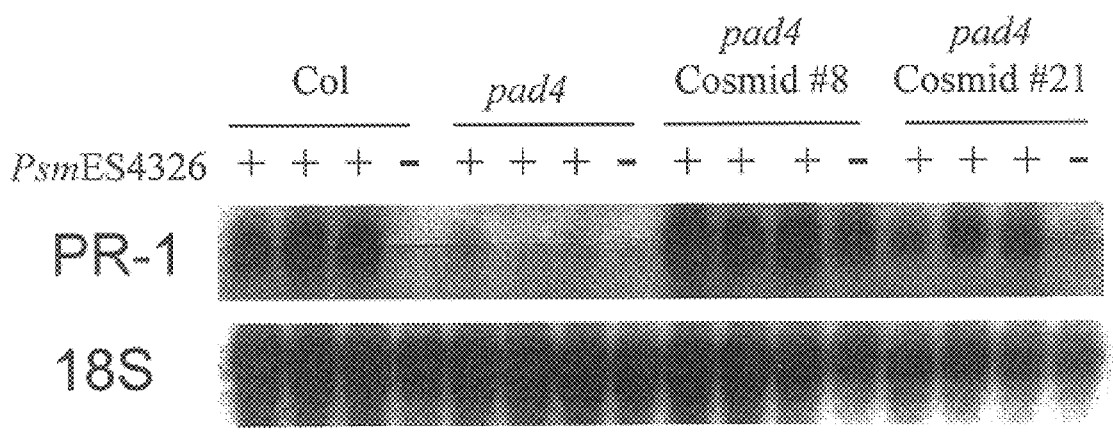

FIGS. 10–10C. Cosmids #8 and #21 Complement the Phytoalexin-Deficient, the Enhanced Bacterial Growth, and PR-1 Phenotypes of pad4-1 Mutants.

FIG. 10A. Cosmids #8 and #21 Complement the Phytoalexin-Deficient Phenotypes of pad4-1 Mutants. For camalexin assay, plants were infected with Psm ES4326 at a dose of $10^5$ cfu/cm$^2$ of leaf, and camalexin was assayed 30 hours later. Each bar represents the mean and standard deviation of at least 6 replicate samples.

FIG. 10B. Cosmids #8 and #21 Complement the Enhanced Bacterial Growth Phenotypes of pad4-1 Mutants. For determination of bacterial growth, plants infected with Psm ES4326 at a dose of $10^3$ cfu/cm$^2$ of leaf, and bacterial density was determined 3 days later. Note that bacterial density is expressed on a log scale. Each bar represents the mean and standard deviation of at least 6 replicate samples.

FIG. 10C. Cosmids #8 and #21 Complement the PR-1 Expression Defect of pad4-1 Mutants. Plants were infected with Psm ES4326 at a dose of OD600=0.002 (+) or left uninfected (−). After 33 hours, tissues were excised, RNA was extracted, and RNA was detected by hybridization with digoxygenin labeled probes. 18S indicates the 18S ribosomal RNA, which serves as a loading control.

Figure 11A:
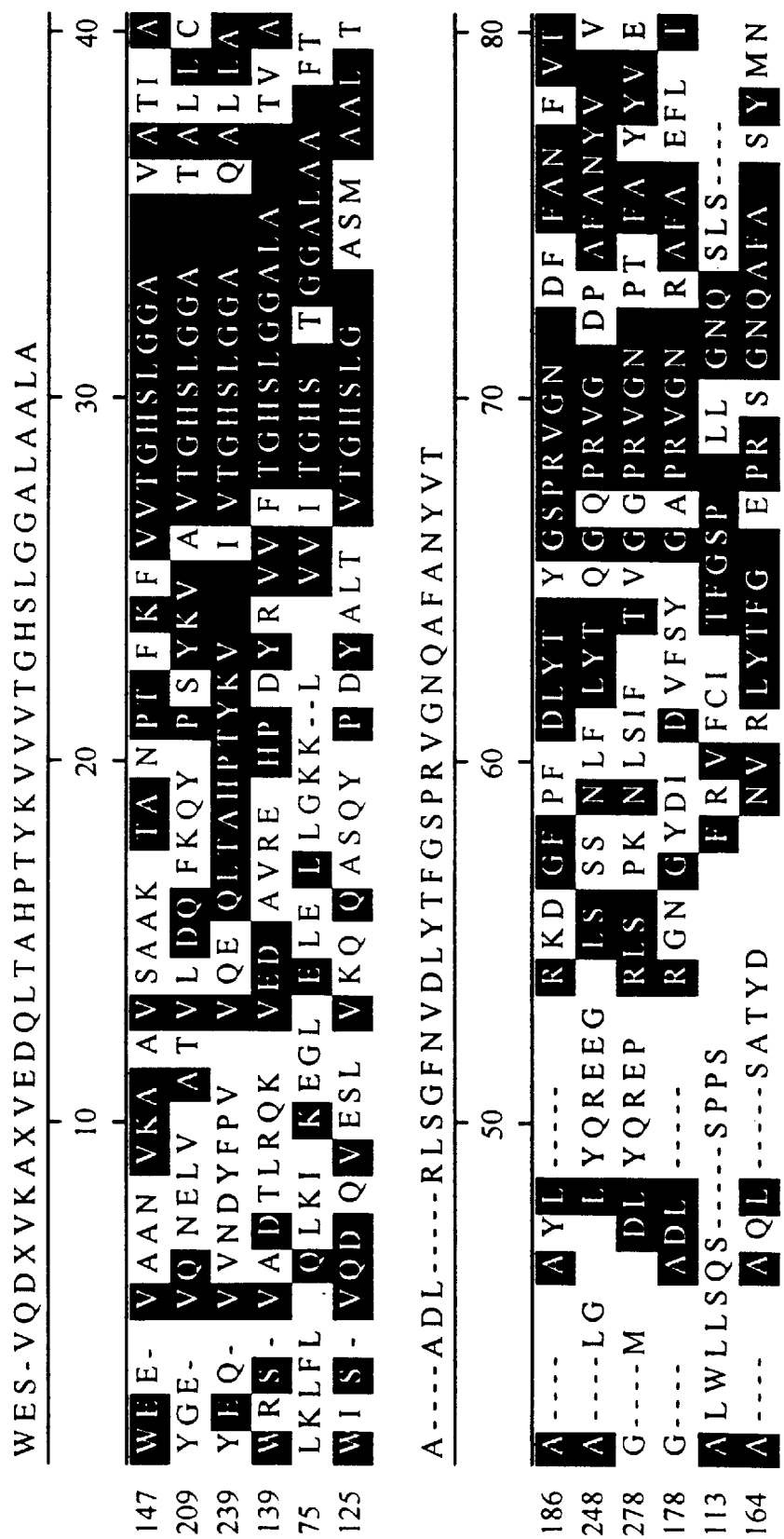

FIGS. 11A–11B. Alignment of Certain Segments of the PAD4 Amino Acid Sequence with Those of Various Lipases and a Hydrolase. Amino acid sequences listed above the numbered line that heads each group of six aligned sequences represent majority sequences. The first through sixth amino acid sequence, respectively, in each group of six aligned sequences are identified by the amino acid positions leftmost in each line as follows: the first amino acid sequences—having positions 147, 186, 217, and 250 leftmost—are from a triacyl glycerol lipase from *Fusarium heterosporum* (GenBank Accession number S77816; SEQ ID NO.:29), the second amino acid sequences—having positions 209, 248, 284, and 317 leftmost—are from a triacyl glycerol lipase from *Rhizomucor miehei* (GenBank accession number A34959; SEQ ID NO.:30), the third amino acid sequences—having positions 239, 278, 314, and 347 leftmost—are from a lipase from *Rhizopus niveus* (GenBank accession number AB013496; SEQ ID NO.:31), the fourth amino acid sequences—having positions 139, 178, 209, and 243 leftmost—are from a lipase from *Thermomyces lanuginosus* (GenBank accession number AF054513; SEQ ID NO.:32), the fifth amino acid sequences—having positions 75, 113, 144, and 183 leftmost—are from PAD4 (SEQ ID NO.:2), and the sixth amino acid sequences—having positions 125, 164, 195, and 235 leftmost—are from a ferulic acid esterase A from *Aspergillus niger* (Gen Bank accession number Y09330; SEQ ID NO.: 33).

Figure 12:
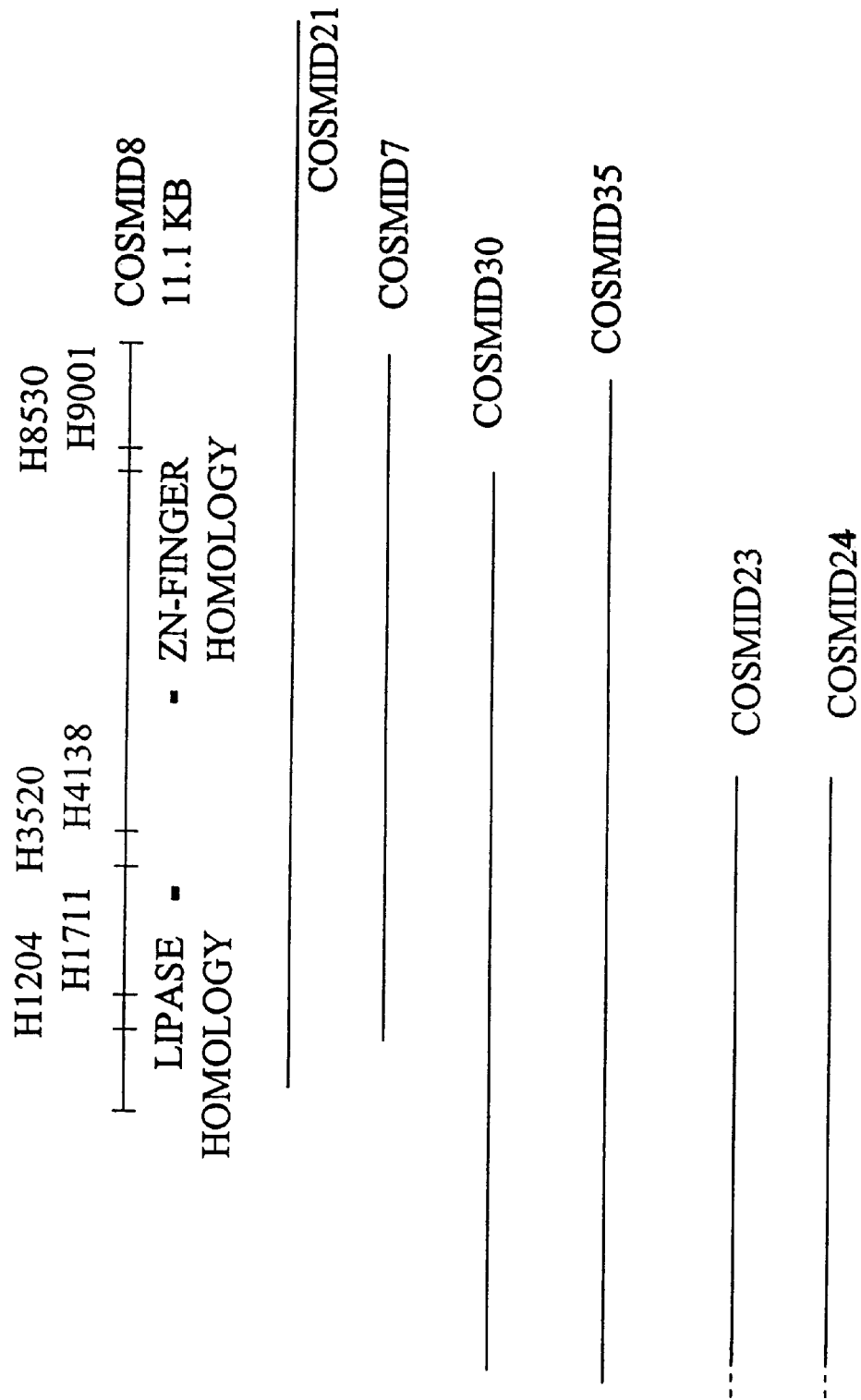

FIG. 12. Cosmids that Complement pad4-1. The approximate relative positions of the Arabidopsis DNA sequences carried by each cosmid are shown. The positions of the HindIII (H) restriction sites, lipase-like sequences, and zinc-finger sequences in cosmid #8 are shown.

Figure 13A:
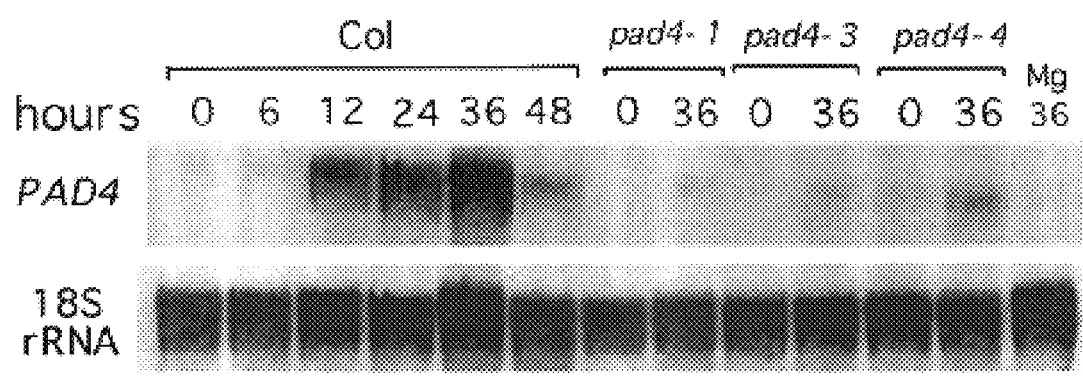
Figure 13B:
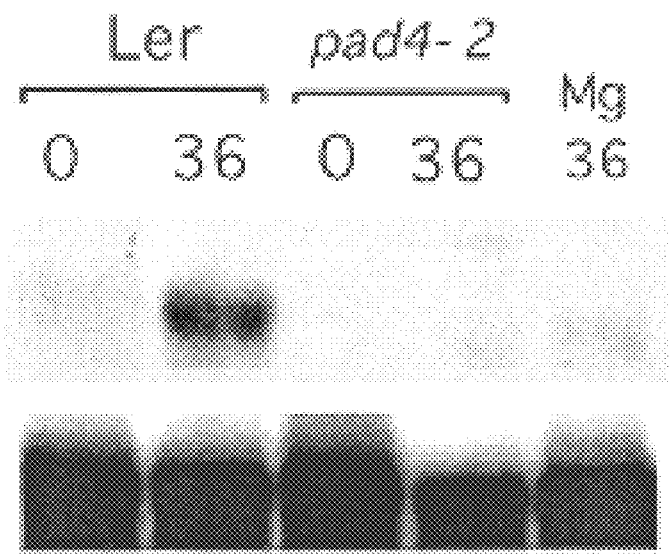

FIGS. 13A–13B. PAD4 Expression is Pathogen-inducible and is Low in pad4 Plants. After infection by Psm ES4326, PAD4 transcript levels are high in wild-type (Col and Ler) plants and greatly reduced in all four pad4 mutant (pad4-1, pad4-2, pad4-3, and pad4-4) plants.

FIG. 13A. Leaves from wild-type (Col) and three pad4 mutant (pad4-1, pad4-3, and pad4-4) plants were excised 0, 6, 12, 24, 36, or 48 hr after infection. "Mg 36" indicates wild-type (Col) leaves mock inoculated with 10 mM MgSO$_4$ and harvested after 36 hr.

FIG. 13B. Leaves from wild-type (Ler) and pad4-2 mutant plants were excised 0 or 36 hr after infection. "Mg 36" indicates wild-type (Ler) leaves mock inoculated with 10 mM MgSO$_4$ and harvested after 36 hr.

Figure 14A:
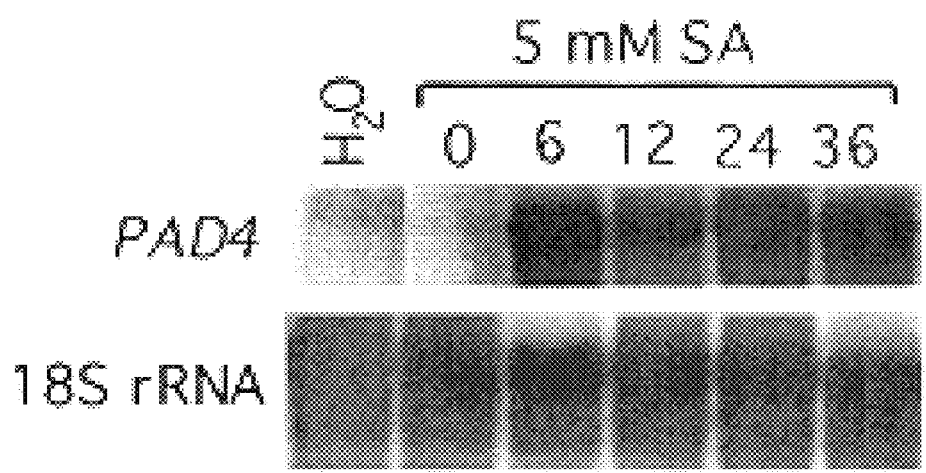
Figure 14B:
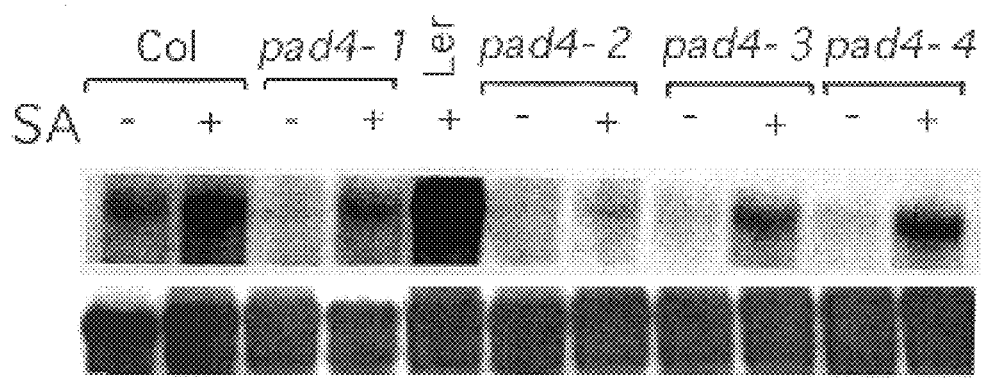

FIGS. 14A–14B. PAD4 Expression is Induced by SA in Wild-type, pad4-1, pad4-3, and pad4-4 Plants. Wild-type (Col and Ler) and all four pad4 mutant (pad4-1, pad4-2, pad4-3, and pad4-4) plants were treated with 5 mM SA in 0.02% Silwet L-77 [v/v] until uniformly wet. Control samples, indicated with "H$_2$O", were treated with 0.02% Silwet L-77 (H$_2$O).

FIG. 14A. Wild-type (Col) plants were sprayed with SA and PAD4 mRNA levels were determined 0, 6, 12, 24, and 36 hours after treatment.

FIG. 14B. Wild-type (Col and Ler) and all four pad4 mutant (pad4-1, pad4-2, pad4-3, and pad4-4) plants were treated with SA and PAD4 mRNA levels were determined 0 and 6 hours after treatment.

Figure 15:
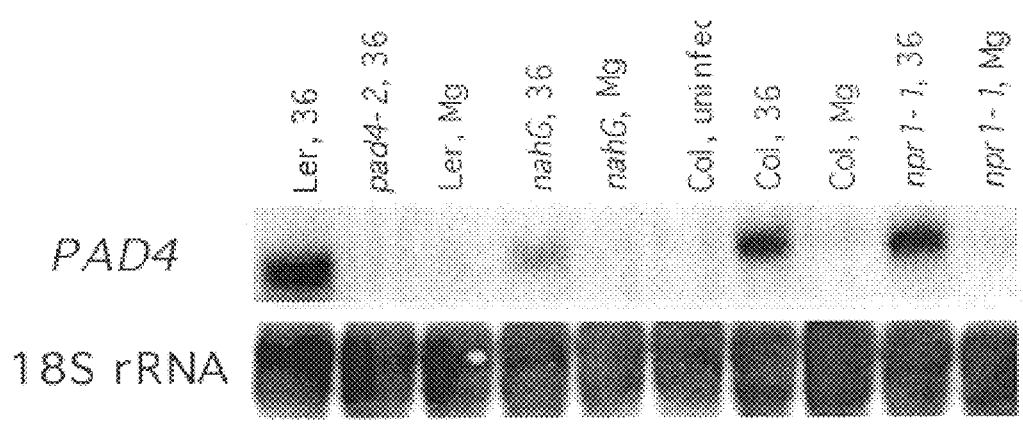

FIG. 15. PAD4 mRNA Induction by Psm ES4326 is SA-dependent but NPR1-independent. Wild-type (Col and Ler), nahG, and npr1-1 plants were infected with Psm ES4326. Samples were analyzed for PAD4 mRNA 36 hours after infection. "Ler, Mg", "nahG, Mg", "Col, Mg", and "npr1-1, Mg" indicate wild-type (Ler), nahG, wild-type (Col), and npr1-1 leaves, respectively, mock inoculated with 10 mM MgSO$_4$ and harvested at 36 hr.

Figure 16:
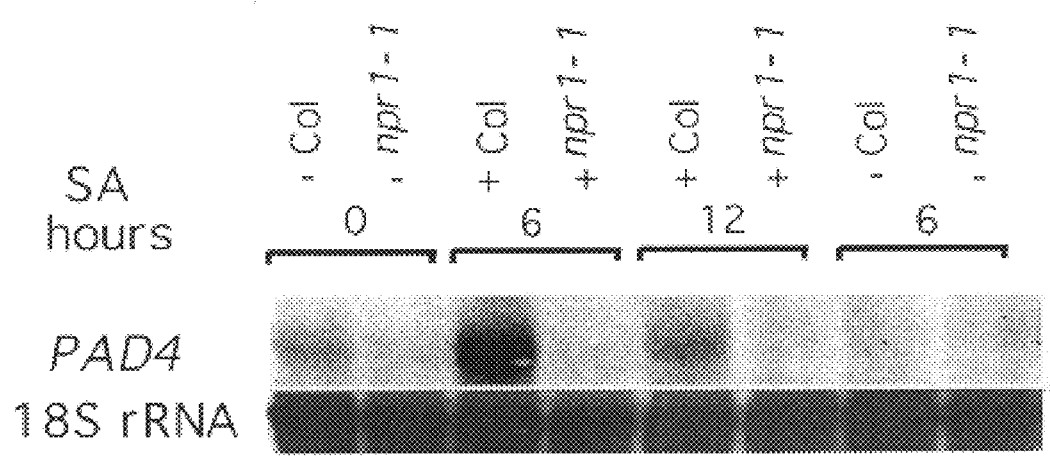

FIG. 16. PAD4 mRNA Induction by SA is NPR1-dependent. Wild-type (Col) and npr1-1 plants were treated with 5mM SA and PAD4 mRNA levels were determined at 0, 6, and 12 hours. Control samples were treated with 0.02% Silwet L-77 (H$_2$O).

FIGS. 17A–17B.

FIG. 17A. Proposed Model 1 for Roles of PAD4, SA, and NPR1 in Defense Gene Expression. SA is necessary but not sufficient for activation of expression of defense genes, including PAD4. Another component is required—either NPR1 or some unknown factor X from the pathogen. NPR1 also inhibits accumulation of SA.

Figure 17B:
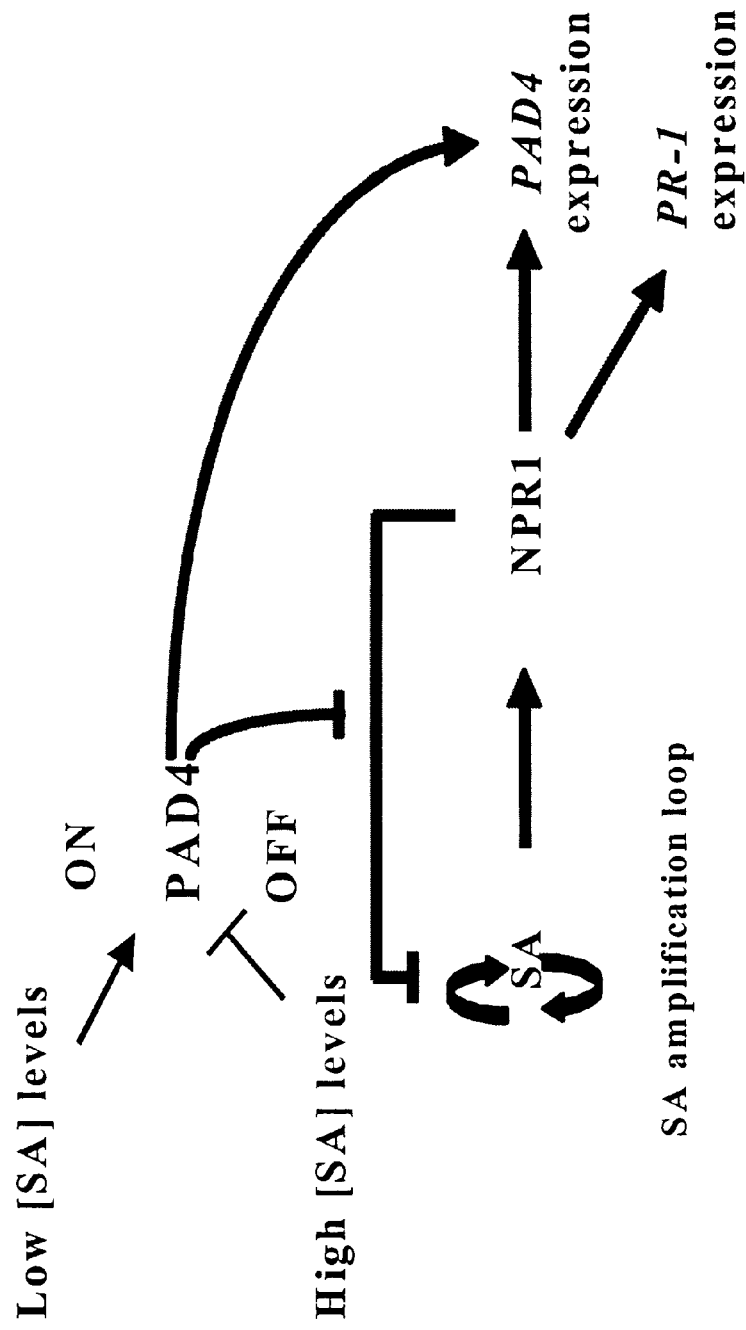

FIG. 17B. Proposed Model 2 for Roles of PAD4, SA, and NPR1 in Defense Gene Expression. Different SA levels modulate PAD4 activity differently. Low SA levels activate, and very high SA levels inactivate, PAD4. Activated PAD4 in turn stimulates expression of defense genes and inhibits the repressing activity of NPR1 on the SA amplification loop. Very high SA levels inactivate PAD4. In this situation, NPR1 activity is required for defense gene expression.

Figure 18A:
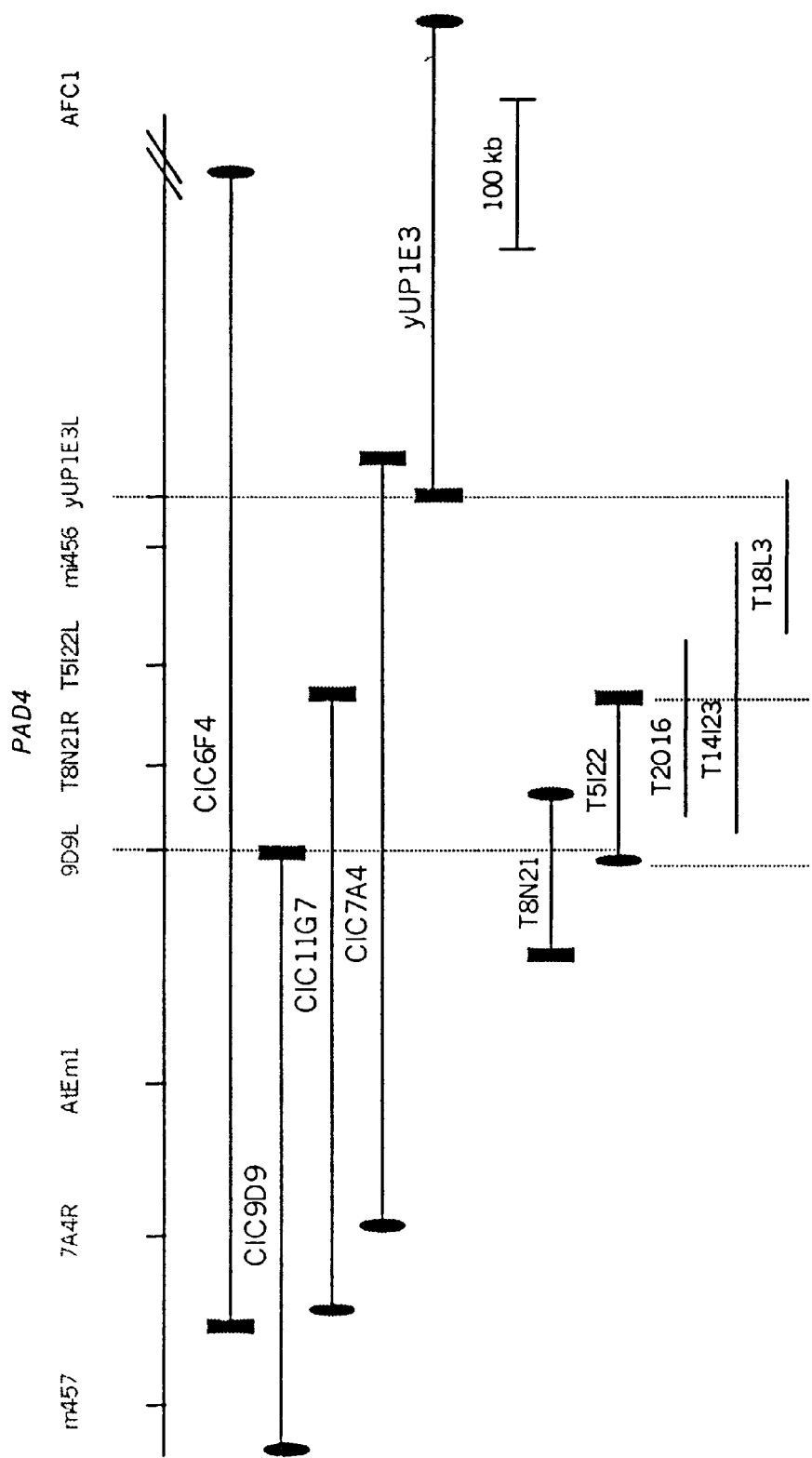
Figure 18B:
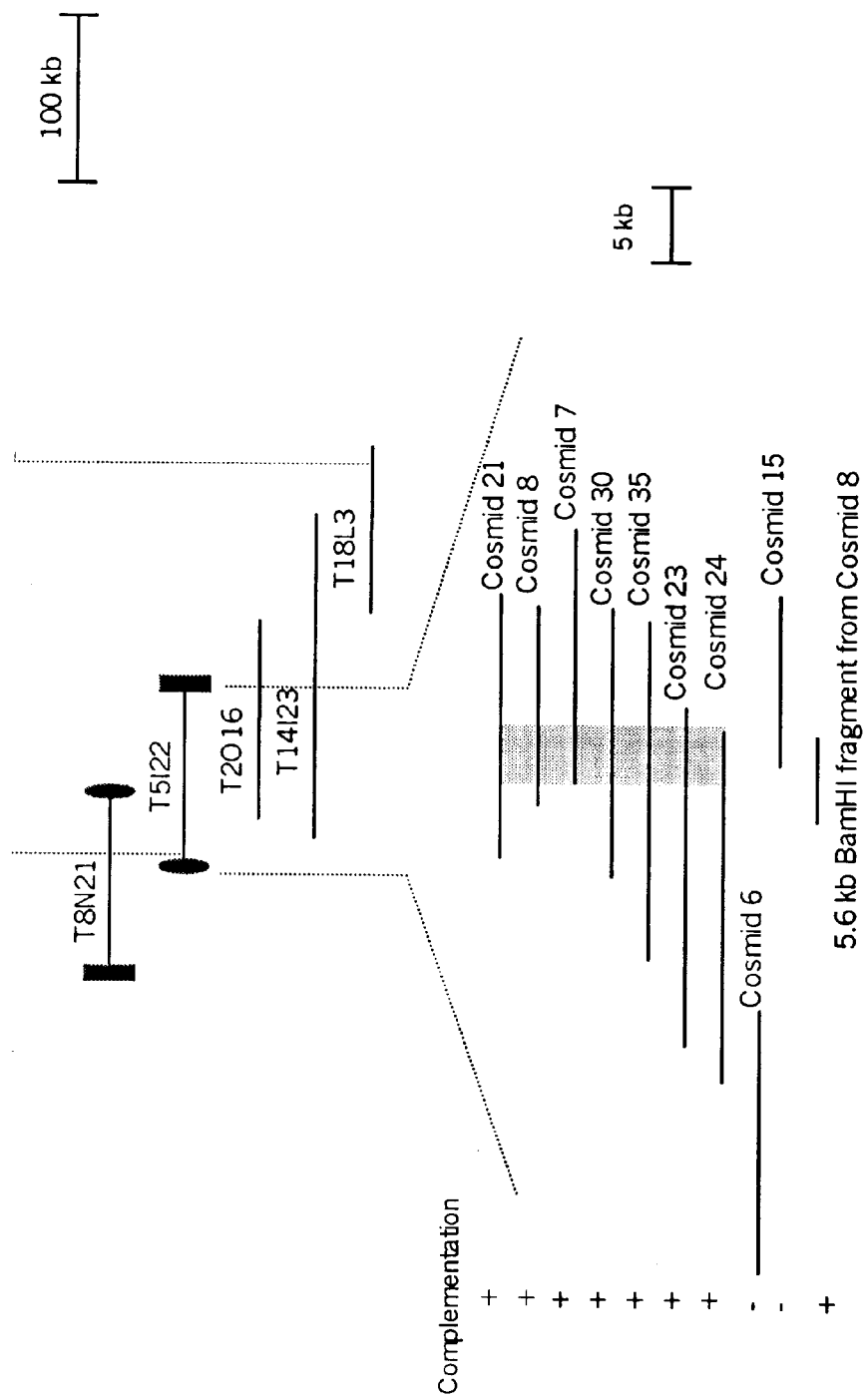

FIGS. 18A–18B. Postional Cloning of PAD4 Gene. A 5 cM region between CAPS markers m457 and AFC1 was partially spanned with YAC, BAC, and cosmid clones ●marks indicate right ends and ■ marks indicate left ends of YAC and BAC clones. The approximate overlap among these clones is shown.

FIG. 18A. BAC Clones and Additional YAC Clones. Relative positions of YAC clones CIC6F4, CIC9D9, CIC11G7, CIC7A4, and yUP1E3 are shown. As in FIG. 18B, relative positions of BAC clones T8N21, T5122, T2016, T14I23, and T18L3 are also shown.

FIG. 18B. BAC Clones and Complementation of Cosmids. Cosmids #7, #8, #21, #23, #24, #30, #35, and a 5.6 kb BamHI fragment from cosmid #8 complement the pad4-1 mutation. Shading indicates the region common to all cosmids. Only 2 of the 13 non-complementing cosmids (i.e., cosmids #6 and #15) are shown here.

Figure 19C:

FIGS. 19A–19C. Alignment of Amino Acid Segment of PAD4 Surrounding a Serine (FIG. 19A), an Aspartic Acid (FIG. 19B), and a Histidine (FIG. 19C) of Putative Lipase Catalytic Triad with those of Various Lipases, an Esterase, and EDS1 from Arabidopsis. Residues of the putative lipase catalytic triad consisting of a serine, a histidine, and an aspartate are indicated by arrows. RhizoTGL= triacylglycerol lipase (EC 3.1.1.3) precursor 1 from *Rhizomucor miehei;* FusaTGL=triacylglycerol lipase (EC 3.1.1.3) from *Fusarium heterosporum;* Rhizolip=triacylglycerol lipase (EC 3.1.1.3) precursor 1 from *Rhizomucor niveus;* Thermolip=lipase from *Thermomyces lanuginosus;* AspFAE=ferulic acid esterase A from *Aspergillus niger;* AtEDS1=*Arabidopsis thaliana* EDS 1; AtPAD4= *Arabidopsis thaliana* PAD4. Invariant residues are indicated in bold letters and conserved amino acids are underlined. The numbering of AtPAD4 residues follows the numbering of SEQ ID NO.:55.

DETAILED DESCRIPTION OF THE PREFERRED EMBODIMENTS

The present inventors demonstrate herein that pad4 mutants exhibit defects in defense responses, including phytoalexin accumulation and pathogenesis-related PR-1 gene expression while having substantially no regulatory effect on PR-5, BGL2, or ASA1 expression levels in a disease defense response when infected by Psm ES4326. In Psm ES4326-infected pad4 plants, synthesis of SA was found to be reduced and delayed when compared to SA synthesis in wild-type plants. Moreover, treatment of pad4 plants with SA partially reversed the phytoalexin deficiency and PR-1 gene expression phenotypes of Psm ES4326-infected pad4 plants. These results indicate that PAD4 acts upstream from SA accumulation in regulation of defense response expression in plants infected with Psm ES4326.

Not wanting to be bound by theory, the present inventors provide FIG. 7 as a working model of the role of PAD4 in defense response signaling. When plants are infected with Psm ES4326, PAD4 is needed for SA concentrations to reach the level required for phytoalexin synthesis and expression of PR-1. In contrast, when plants are infected with Psm ES4326 carrying avrRpt2, SA accumulates in a PAD4-independent manner.

The inventors also present evidence for the existence of a PAD4-SA amplification loop in defense signaling. Again, not wanting to be bound by theory, the inventors provide FIG. 17A and FIG. 17B as working models of the roles of PAD4, SA, and NPR1 in defense gene expression. For either model, PAD4 protein has a positive regulatory effect on expression levels of PAD4 and PR-1 (as well as, through SA and an unknown factor, on phytoalexin levels) at least, according to the second model (FIG. 17B), when SA levels are not so high as to prevent PAD4 from inhibiting NPR1 inhibition of a SA amplification loop.

The present inventors also provide the nucleotide sequence of nucleic acid adjacent to and including PAD4 from Arabidopsis, encoded protein sequences, and methods and uses thereof.

The compositions and methods described herein are useful for a variety of agricultural and commercial purposes including, but not limited to, enhancing disease resistance against plant pathogens and environmental factors, increasing crop yields, improving crop and ornamental quality, and reducing agricultural production costs. In particular, ectopic expression of a PAD4 gene in a plant cell is provided for enhanced disease resistance to plant pathogens and can be used to protect plants from pathogen infestation that reduces plant productivity and viability.

The invention also provides for broad-spectrum pathogen resistance by facilitating the natural mechanism of host resistance. For example, PAD4 transgenes can be expressed in plant cells at sufficiently high levels to initiate enhanced disease defense response constitutively in the absence of signals from the pathogen. The level of expression associated with such a plant defense response may be determined by measuring the levels of defense response gene expression as described herein or according to any conventional method. If desired, the PAD4 transgenes are expressed by a controllable promoter such as a tissue-specific promoter, cell-type specific promoter, or by a promoter that is induced by an external signal or agent such as a pathogen- or wound-inducible control element, thus limiting the temporal or tissue expression or both of a disease defense response. The PAD4 genes may also be expressed in roots, leaves, or fruits, or at a site of a plant that is susceptible to pathogen penetration and infection.

The invention is also useful to controlling plant disease by enhancing a plant's disease defense mechanisms. In particular, the invention is useful for combating diseases known to be inhibited by plant disease defense mechanisms.

Table 1 provides identification of sequences having sequence identifiers for the present invention.

TABLE 1

Identification of Sequences Having Sequence Identifiers

| SEQ ID NO: | IDENTITY |
|---|---|
| 1 | nucleotide sequence of wild type PAD4 cDNA from pAtcPAD4 |
| 2 | amino acid sequence of wild type PAD4 protein encoded by SEQ ID NO.:1 |
| 3 | nucleotide sequence of mutant pad4-1 cDNA |
| 4 | amino acid sequence of mutant pad4-1 protein encoded by SEQ ID NO.:3 |
| 5 | nucleotide sequence of Arabidopsis genomic clone from pAtgPAD4 |
| 6 | amino acid sequence of zinc finger homology region from SEQ ID NO.:5 |
| 7 | primer PAD4.18 used to sequence PAD4 and pad4-1 alleles, covering positions 1 to 20 in pAtgPAD4 |
| 8 | primer PAD4.19 used to sequence PAD4 and pad4-1 alleles, covering positions 1362 to 1342 in pAtgPAD4 |
| 9 | primer PAD4.4 used to sequence PAD4 and pad4-1 alleles, covering positions 1236 to 1255 in pAtgPAD4 |
| 10 | primer PAD4.20 used to sequence PAD4 and pad4-1 alleles, covering positions 2675 to 2654 in pAtgPAD4 |
| 11 | primer PAD4.21 used to sequence PAD4 and pad4-1 alleles, covering positions 2435 to 2457 in pAtgPAD4 |
| 12 | primer PAD4.22 used to sequence PAD4 and pad4-1 alleles, covering positions 3834 to 3813 in pAtgPAD4 |
| 13 | primer PAD4.23 used to sequence PAD4 and pad4-1 alleles, covering positions 3647 to 3665 in pAtgPAD4 |
| 14 | primer PAD4.24 used to sequence PAD4 and pad4-1 alleles, covering positions 4868 to 4848 in pAtgPAD4 |
| 15 | primer PAD4.25 used to sequence PAD4 and pad4-1 alleles, covering positions 4648 to 4668 in pAtgPAD4 |
| 16 | primer PAD4.26 used to sequence PAD4 and pad4-1 alleles, covering positions 5579 to 5555 in pAtgPAD4 |
| 17 | primer PAD4.16 used to sequence PAD4 and pad4-1 alleles, covering positions 5479 to 5498 in pAtgPAD4 |
| 18 | primer PAD4.29 used to sequence PAD4 and pad4-1 alleles, covering positions 6936 to 6917 in pAtgPAD4 |
| 19 | primer PAD4.30 used to sequence PAD4 and pad4-1 alleles, covering positions 6095 to 6114 in pAtgPAD4 |
| 20 | primer PAD4.5 used to sequence PAD4 and pad4-1 alleles, covering positions 8293 to 8273 in pAtgPAD4 |
| 21 | primer PAD4.31 used to sequence PAD4 and pad4-1 alleles, covering positions 8075 to 8094 in pAtgPAD4 |
| 22 | primer PAD4.13 used to sequence PAD4 and pad4-1 alleles, covering positions 9324 to 9304 in pAtgPAD4 |
| 23 | primer PAD4.33 used to sequence PAD4 and pad4-1 alleles, covering positions 9024 to 9045 in pAtgPAD4 |
| 24 | primer PAD4.34 used to sequence PAD4 and pad4-1 alleles, covering positions 9654 to 9632 in pAtgPAD4 |
| 25 | primer PAD4.7 used to sequence PAD4 and pad4-1 alleles, covering positions 9485 to 9506 in pAtgPAD4 |
| 26 | primer PAD4.11 used to sequence PAD4 and pad4-1 alleles, covering positions 10516 to 10494 in pAtgPAD4 |
| 27 | primer PAD4.35 used to sequence PAD4 and pad4-1 alleles, covering positions 10404 to 10430 in pAtgPAD4 |
| 28 | primer PAD4.36 used to sequence PAD4 and pad4-1 alleles, covering positions 11152 to 11134 in pAtgPAD4 |
| 29 | amino acid sequence of positions 147 to 276 of a triacyl glycerol lipase from *Fusarium heterosporum* |
| 30 | amino acid sequence of positions 209 to 357 of a triacyl glycerol lipase from *Rhizomucor miehei* |
| 31 | amino acid sequence of positions 239 to 385 of a lipade from *Rhizopus niveus* |
| 32 | amino acid sequence of positions 139 to 268 of a lipase from *Thermomyces lanuginosus* |
| 33 | amino acid sequence of positions 125 to 254 of a ferulic acid esterase A from *Aspergillus niger* |
| 34 | primer for gl1 CAPS marker |
| 35 | primer for gl1 CAPS marker |
| 36 | primer for TOPP5 CAPS marker |
| 37 | primer for TOPP5 CAPS marker |
| 38 | primer for m409 CAPS marker |
| 39 | primer for m409 CAPS marker |
| 40 | primer for m457 CAPS marker |

TABLE 1-continued

Identification of Sequences Having Sequence Identifiers

| SEQ ID NO: | IDENTITY |
|---|---|
| 41 | primer for m457 CAPS marker |
| 42 | primer for 7A4R CAPS marker |
| 43 | primer for 7A4R CAPS marker |
| 44 | primer for AtEM1 CAPS marker |
| 45 | primer for AtEM1 CAPS marker |
| 46 | primer for 1E3L CAPS marker |
| 47 | primer for 1E3L CAPS marker |
| 48 | primer for 9D9L CAPS marker |
| 49 | primer for 9D9L CAPS marker |
| 50 | primer for AFC1 CAPS marker |
| 51 | primer for AFC1 CAPS marker |
| 52 | primer for BGL1 CAPS marker |
| 53 | primer for BGL1 CAPS marker |
| 54 | nucleotide sequence of wild type PAD4 cDNA; pAtcPAD4.2 carries wild-type, PCR-amplified PAD4 cDNA in a Bluescript SK+ vector. |
| 55 | amino acid sequence of wild type PAD4 protein encoded by SEQ ID NO.:54 |
| 56 | nucleotide sequence of mutant pad4-1 cDNA corresponding to SEQ ID NO.:54 but for G-to-A base change at position 1076 |
| 57 | amino acid sequence of mutant pad4-1 protein encoded by SEQ ID NO.:56 |
| 58 | nucleotide sequence of mutant pad4-2 cDNA corresponding to SEQ ID NO.:54 but for insertion of an extra T at position 430 |
| 59 | amino acid sequence of mutant pad4-2 protein encoded by SEQ ID NO.:58 |
| 60 | nucleotide sequence of mutant pad4-3 cDNA corresponding to SEQ ID NO.:54 but for C-to-T base change at position 1156 |
| 61 | amino acid sequence of mutant pad 4-3 protein encoded by SEQ ID NO.:60 |
| 62 | nucleotide sequence of mutant pad4-4 cDNA corresponding to SEQ ID NO.:54 but for G missing at position 1537 |
| 63 | amino acid sequence of mutant pad4-4 protein encoded by SEQ ID NO.:62 |
| 64 | amino acid sequence of positions 199 to 254 of a triacyl glycerol lipase from *Rhizomucor miehei* |
| 65 | amino acid sequence of positions 250 to 302 of a triacyl glycerol lipase from *Rhizomucor miehei* |
| 66 | amino acid sequence of positions 342 to 356 of a triacyl glycerol lipase from *Rhizomucor miehei* |
| 67 | amino acid sequence of positions 139 to 190 from a triacyl glycerol lipase from *Fusarium heterosporum* |
| 68 | amino acid sequence of positions 189 to 235 from a triacyl glycerol lipase from *Fusarium heterosporum* |
| 69 | amino acid sequence of positions 279 to 293 from a triacyl glycerol lipase from *Fusarium heterosporum* |
| 70 | amino acid sequence of positions 228 to 283 from a lipase from *Rhizopus niveus* |
| 71 | amino acid sequence of positions 282 to 332 from a lipase from *Rhizopus niveus* |
| 72 | amino acid sequence of positions 371 to 385 from a lipase from *Rhizopus niveus* |
| 73 | amino acid sequence of positions 129 to 182 from a lipase from *Thermomyces lanuginosus* |
| 74 | amino acid sequence of positions 181 to 228 from a lipase from *Thermomyces lanuginosus* |
| 75 | amino acid sequence of positions 271 to 285 from a lipase from *Thermomyces lanuginosus* |
| 76 | amino acid sequence of positions 115 to 168 from a ferulic acid esterase A from *Aspergillus niger* |
| 77 | amino acid sequence of positions 168 to 220 from a ferulic acid esterase A from *Aspergillus niger* |
| 78 | amino acid sequence of positions 259 to 273 from a ferulic acid esterase A from *Aspergillus niger* |
| 79 | amino acid sequence of positions 83 to 142 from EDS1 from *Arabidopsis thaliana* |
| 80 | amino acid sequence of positions 145 to 192 from EDS1 from *Arabidopsis thaliana* |
| 81 | amino acid sequence of positions 308 to 322 from EDS1 from *Arabidopsis thaliana* |
| 82 | antisense primer for antisense PAD4 probe and gene-specific primer for 5' RACE product |
| 83 | gene-specific primer for 3' RACE product |
| 84 | primer for isolation of wild-type PAD4 cDNA (as in SEQ ID NO.:54) corresponding to one end of cDNA sequence |
| 85 | primer for isolation of wild-type PAD4 cDNA (as in SEQ ID NO.:54) corresponding to other end of cDNA sequence |

Nucleic Acid Embodiments of the Present Invention

As used herein, the term "purified nucleic acid molecule" refers to a DNA or RNA molecule that has been isolated free of total genomic nucleic acid. Therefore, a "purified nucleic acid molecule", as used herein, refers to a nucleic acid molecule that contains a PAD4-related nucleotide sequence, yet is isolated away from, or purified free from, total genomic DNA or total genomic RNA. The term "purified nucleic acid molecule" therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by polymerase chain reaction (PCR) or restriction endonuclease digestion) independent of other sequences. It also includes a recombinant DNA that is part of a hybrid gene encoding additional polypeptide sequence.

The term "essentially set forth as" as used herein related to nucleic acid molecules encoding an open reading frame, means that a nucleic acid sequence substantially corresponds to a portion of a sequence identifier and has relatively few codons which are not identical, or functionally equivalent, to the codons of said sequences. The term "functionally equivalent codon" is used herein to refer to codons that encode the same amino acid, such as the six codons for arginine or serine, for example, and also refers to codons that encode biologically equivalent amino acids.

The term "essentially set forth as" as used herein related to nucleic acid molecules not encoding an open reading frame means sequences, excepting flanking regions, that have between about 70% and about 80%; or more preferably, between about 80% and about 90%; or even more preferably, between about 90% and about 99%; of nucleotides which are identical to the nucleotides of a sequence identifier. Nucleotide sequences that are essentially the same as those set forth in a sequence identifier may also be functionally defined as sequences that are capable of hybridizing to a nucleic acid segment containing the complement of said sequences under relatively stringent conditions. Suitable relatively stringent hybridization conditions are well known to those of skill in the art and are set forth herein.

Included within the term "nucleic acid molecule" are allelic variants, natural mutants, nucleic acid segments and smaller fragments of such segments; and also recombinant vectors, including, for example, plasmids, cosmids, and the like.

By "PAD4" gene is meant a gene encoding: a protein, the protein capable of regulating phytoalexin accumulation and pathogenesis-related PR-1 gene expression while having substantially no regulatory effect on PR-5, BGL2, or ASA1 expression levels in a disease defense response in a plant cell or plant tissue. Without limiting the class of all PAD4 genes, some PAD4 genes may be characterized as encoding a protein, the protein additionally being capable of regulating PAD4 expression levels (i.e., in addition to regulating phytoalexin accumulation and pathogenesis-related PR-1 gene expression while having substantially no regulatory effect on PR-5, BGL2, or ASA1 expression levels in a disease defense response in a plant cell or plant tissue). PAD4 genes may be identified and isolated from any plant species, especially agronomically important crop plants, using any of the sequences disclosed herein in combination with conventional methods known in the art in light of the present disclosure. The term "gene" is used for simplicity to refer to a functional protein-, polypeptide- or peptide-encoding unit. As will be understood by those in the; art in light of this disclosure, this functional term includes genomic sequences, cDNA sequences or combinations thereof.

By "factor" is meant an aspect of a nucleic acid sequence capable of regulating a plant disease response as set forth supra. Such an aspect may be a cis-acting sequence, a transcript, or an encoded protein, for example.

As used herein, the term "recombinant vector", refers to a vector that has been modified to contain a nucleic acid segment that encodes a protein or peptide of the present invention, or fragment of interest thereof. The recombinant vector may be further defined as an expression vector comprising a promoter operatively linked to said protein or peptide encoding nucleic acid molecule. The recombinant vector may also comprise other sequences such as expression control sequences, markers, amplifying genes, signal sequences, and the like.

By way of example and not limitation, vectors may be further described as being among or like those disclosed in U.S. Pat. Nos. 4,757,011, 4,769,061, 4,940,835, and 4,971,908 (each of which is herein incorporated by reference); other examples include cloning/expression vectors such as pGEM-T (Promega Biotech, Madison, Wis.) or pBluescript (Strategene, La Jolla, Calif.), either of which is propagated in a suitable *E. coli* host cell.

For use in a vector-free system, nucleic acid sequences may be designed so as to effect homologous recombination, for example.

For expression, the PAD4 coding sequences are positioned adjacent to and under the control of a promoter. Further regulatory elements include, for example, a polyadenylation site, translation enhancer, sequences, or termination signals. The nucleic acid molecules of the present invention, regardless of the length of the coding sequence itself, may be combined with other DNA sequences, such as additional restriction enzyme sites, multiple cloning sites, other coding segments, and the like, such that their overall length may vary considerably.

Examples of promoters include the octopine synthase (ocs), mannopine synthase (mas), and nopaline synthase (nos) promoters of Agrobacterium plasmids; the actin promoter from rice; the ubiquitin promoter from maize; the LTP (Lipid Transfer Protein) promoters from broccoli; the chitinase promoter from Arabidopsis; the EIF-4A promoter from tobacco; the light-inducible promoter from the small subunit of ribulose-1,5-bisphosphate carboxylase (ssRUBISCO); the Figwort Mosaic Virus (FMV) 35S promoter; the cauliflower mosaic virus (CaMV) 19S and 35S promoters; enhanced CaMV promoters, and the like.

The present invention includes a purified nucleic acid molecule complementary, or essentially complementary, to a nucleic acid molecule having a sequence set forth in a sequence identifier. Nucleic acid sequences which are "complementary" are those which are capable of base-pairing according to the standard Watson-Crick complementation rules. As used herein, the term "complementary sequences" means nucleic acid sequences which are substantially complementary, as may be assessed by the same nucleotide comparison set forth above, or as defined as being capable of hybridizing to the nucleic acid segment of said sequences under relatively stringent conditions such as those described herein.

The invention further includes nucleotide sequences that facilitate specific detection of a PAD4 nucleic acid. Thus, PAD4 sequences described herein or portions thereof may be used as probes to hybridize to nucleotide sequences from other plants (e.g., dicots, monocots, gymnosperms, and algae) by standard hybridization techniques under conventional conditions. Sequences that hybridize to a PAD4 coding sequence or its complement and that encode a PAD4 polypeptide are considered useful in the invention. As used herein, the term "fragment," as applied to nucleic acid sequences, means at last 5 contiguous nucleotides, preferably at least 10 contiguous nucleotides, more preferably at least 20 to 30 contiguous nucleotides, and most preferably at least 40 to 80 or more contiguous nucleotides. Fragment of PAD4 nucleic acid sequences can be generated by methods known to those skilled in the art. Complementary nucleotide sequences are useful for detection and purification of hybridizing nucleic acid molecules.

By "reporter gene" is meant a gene whose expression may be assayed; such genes include, without limitation, β-glucuronidase (GUS), luciferase, chloramphenicol transacetylase (CAT), green fluorescent protein (GFP), β-galactosodase, herbicide resistant genes and antibiotic resistance genes.

Protein Embodiments

The present invention provides a purified protein having a positive regulatory effect on phytoalexin levels and on PR-1 expression levels while having substantially no regulatory effect on PR-5, BGL2, or ASA1 expression levels in a disease defense response by a host plant. In certain embodiments, the present invention further provides a purified protein having a positive regulatory effect on its own expression levels (in addition to having a positive regulatory effect on phytoalexin levels and PR-1 expression levels while having substantially no regulatory effect on PR-5, BGL2, or ASA1 expression levels in a disease defense response in a host plant). By "purified protein" is meant a protein that has been isolated free of total cellular milieu. In particular, proteins of the present invention are wild-type PAD4 having an amino acid sequence essentially set forth in SEQ ID NO.:2 or SEQ ID NO.:55, or comprising an amino acid sequence essentially set forth in SEQ ID NO.:2 or SEQ ID NO.:55. By "having a positive regulatory effect" is meant that, in the presence of the protein, levels of effected substances are increased. By "having substantially no regulatory effect" is meant that, in the presence of protein, no significant change of levels occurs.

A PAD4 polypeptide may be obtained, for example, by extraction from a natural source (for example, a plant cell); by expression of a recombinant nucleic acid encoding a PAD4 polypeptide; or by chemically synthesizing the protein. Purity can be measured by any appropriate method, for example, column chromatography, polyacrylamide gel electrophoresis, or by HPLC analysis.

The term "amino acid sequence essentially set forth", or the term "amino acid sequence essentially as set forth", in a sequence identifier means that the sequence substantially corresponds to a portion of the sequence of the sequence identifier and has relatively few amino acids which are not identical to, or a biologically functional equivalent of, the amino acids of the sequence identifier. The term "biologically functional equivalent" is well understood in the art and is further defined as a protein having a sequence essentially as set forth in a sequence identifier, capable of enhancing disease resistance in a plant. Accordingly, sequences which have between about 70% and about 80%; or more preferably, between about 81% and about 90%; or even more preferably, between about 91% and about 99%; of amino acids that are identical or functionally equivalent to the amino acids of a sequence identifier are sequences which are "essentially as set forth in" a sequence identifier.

By "polypeptide" or "protein" is meant any chain of amino acids, regardless of length or post-translational modification (for example, glycosylation or phosphorylation).

Modifications and changes may be made in the sequence of PAD4 proteins of the present invention and still obtain a peptide or protein having like or otherwise desirable characteristics. For example, certain amino acids may be substituted for other amino acids in a peptide without appreciable loss of function. Since it is the interactive capacity and higher order structure assumed by an amino acid sequence that defines a peptide's functional activity, certain amino acid sequences (or, of course, encoding nucleic acid sequences) may be added, replaced, or deleted, and a peptide with like properties obtained. It is thus contemplated by the inventors that certain changes may be made in the sequence of a PAD4 protein (or encoding nucleic acid) without appreciable loss of its ability to function.

Substitution of like amino acids can be made; on the basis of hydrophilicity. U.S. Pat. No. 4,554,101, incorporated herein by reference, states that the following hydrophilicity values have been assigned to amino acid residues: arginine: (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid may be substituted for another having a similar hydrophilicity value and still obtain a biologically equivalent peptide. In such changes, the substitution of amino acids whose hydrophilicity values are within ±2 is preferred, those which are within ±1 are more preferred, and those within ±0.5 are most preferred. Amino acid substitutions are generally, therefore, based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Sequence identity or homology is typically measured using sequence analysis software (for example, Sequence Analysis Software Package of the Genetics Computer Group, University of Wisconsin Biotechnology Center, 1710 University Avenue, Madison, Wis. 53705, BLAST, FASTA, or PILEUP/PRETTYBOX programs). Such software matches identical or similar sequences by assigning degrees of homology to various substitutions, deletions, and/or other modifications. Sequence analysis software or algorithms such as BLAST or FASTA are relied on, for example, in U.S. Pat. Nos. 5,859,197, 5,827,516, and 5,850,020, each incorporated herein by reference, in measuring or assigning degrees of homology.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

It will also be understood that amino acid and nucleic acid sequences may include additional residues, such as additional N- or C-terminal amino acids or 5' or 3' nucleotides, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region, or may include various coding or noncoding internal sequences, i.e., amino acids that form the junction between a protein fused to a PAD4 protein, for example.

The invention further includes analogs of any naturally-occurring plant PAD4 polypeptide. Analogs can differ from the naturally-occurring PAD4 protein by amino acid sequence differences, by post-translational modifications, or by both. Analogs of the invention will generally exhibit at least 40%, more preferably 50%, and most preferably 60% or even having 70%, 80%, or 90% identity with all or part of a naturally-occurring plant PAD4 amino acid sequence. Modifications include in vivo and in vitro chemical derivation of polypeptides, e.g., acetylation, carboxylation, phosphorylation, or glycosylation; such modifications may occur during polypeptide synthesis or processing or following treatment with isolated modifying enzymes. Analogs can also differ from the naturally occurring PAD4 polypeptide by alterations in primary sequence. These include genetic variants, both natural and induced (for example, resulting from random mutagenesis by irradiation or exposure to ethyl methylsulfate or by site-specific mutagenesis. Also included are cyclized peptides, molecules, and analogs which contain residues other than L-amino acids, e.g., D-amino acids or non-naturally occurring or synthetic amino acids, e.g., β or γ amino acids.

In addition to full-length and/or complete polypeptides, the invention also includes PAD4 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of PAD4 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

By "purified antibody" is meant antibody free from naturally-occurring milieu of antibody producing cells. By "binding specificity" is meant an antibody that has affinity for PAD4 protein and lacks affinity for other molecules in a sample, for example, a biological sample, which naturally includes a PAD4 protein.

PAD4 polypeptides described herein (or imunogenic fragments or analogs) may be used to raise antibodies useful in the invention; such polypeptides may be produced by recombinant or peptide synthetic techniques. The peptides may be coupled to a carrier protein, such as KLH, for example. The KLH-peptide is mixed with Freund's adjuvant and injected into guinea pigs, rats, or, preferably, rabbits. Antibodies may be purified by peptide antigen affinity chromatography.

Monoclonal antibodies may be prepared using PAD4 polypeptides described herein and standard hybridoma technology. Once produced, polyclonal or monoclonal antibodies are tested for specific PAD4 recognition by Western blot or immunoprecipitation analysis. Antibodies having binding specificity for PAD4 polypeptides are considered to be useful in the invention; such antibodies may be used, e.g., in an immunoassay to monitor the level of PAD4 polypeptide produced by a plant.

The provision of PAD4 sequences also facilitates the identification of polypeptides which interact with PAD4 protein. Such polypeptide-encoding sequences are isolated by any standard two hybrid system. For example, all or a part of a PAD4 sequence may be fused to a DNA binding domain (such as the GAL4 or LexA DNA binding domain). After establishing that this fusion protein does not itself activate expression of a reporter gene (for example, a lacZ or LEU2 reporter gene) bearing appropriate DNA binding sites, this fusion protein is used as an interaction target. Genes encoding candidate interacting proteins fused to an activation domain (for example, an acidic activation domain) are then co-expressed with genes encoding the PAD4-DNA binding domain fusion protein in host cells, and interacting proteins are identified by their ability to contact the PAD4 sequence and stimulate reporter gene expression. PAD4-interacting proteins identified using this screening method provide good candidates for proteins that are involved in the disease defense response.

Recombinant Cells

A further aspect of the present invention is a host cell, made recombinant with a recombinant vector comprising a nucleic acid molecule of the present invention, preferably a nucleic acid molecule encoding PAD4. The recombinant host cell may be a prokaryotic or a eukaryotic cell. In a more preferred embodiment, the recombinant host cell is a eukaryotic cell, in particular, a plant cell. As used herein, the term "engineered" or "recombinant" cell is intended to refer to a cell into which a recombinant gene, such as a gene encoding PAD4, has been introduced. Therefore, engineered cells are distinguishable from naturally occurring cells that do not contain a recombinantly introduced gene. Thus, engineered cells are cells having a gene introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene, or combinations thereof.

Exemplary host cells may be further defined as *Escherichia coli* or other prokaryotic cells, and the like, or eukaryotic cells including, for example, *Saccharomyces cerevisiae* cells, mammalian cells (for example, COS 1 or N1H 3T3 cells), or any of a number of plant cells including, without limitation, cells of algae, tree species, ornamental species, temperate fruit species, tropical fruit species, vegetable species, legume species, crucifer species, monocots, dicots, or in any plant of commercial or agricultural significance maintained in tissue culture or occurring in vivo.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgenic) is inserted by artifice into the nuclear or an organellar genome. A transgenic plant according to the invention may contain one or more PAD4 genes.

By "plant cell" is meant any self-propagating cell bounded by a semi-permeable membrane and containing a plastid. Such a cell also generally requires a cell wall if further propagation is desired. Plant cell, as used herein, includes, for example, algae, cyanobacteria, seeds, suspension cultures, embryos, meristematic regions, callus tissue, leaves, roots, shoots, gametophytes, sporophytes, pollen, and microspores.

By "crucifer" is meant any plant that is classified within the Cruciferae family. The Cruciferae include many agricultural crops, including, for example, rape (for example, *Brassica campestris* and *Brassica napus*), broccoli, cabbage, brussel sprouts, radish, kale, Chinese kale, kohlrabi, cauliflower, turnip, rutabaga, mustard, horseradish, and Arabidopsis. Cells of Cruciferae family plants are included among suitable host cells. Particular examples of other plant cells suitable as hosts include, but are not limited to, cells from conifers, petunia, tomato, potato, pepper, tobacco, lettuce, sunflower, flax, cotton, sugarbeet, celery, soybean, Medicago such as alfalfa, lotus, Vigna, cucumber, carrot, egg plant, morning glory, poplar, walnut, apple, grape, asparagus, cassava, rice, maize, millet, onion, barley, orchard grass, oat, rye, and wheat.

Compositions and Methods for Hybridization

DNA probes and primers useful in hybridization studies and PCR reactions may be derived from any portion of nucleic acid molecules of the present invention having sequence identifiers and are generally at least about seventeen nucleotides in length. Therefore, probes and primers are specifically contemplated that comprise nucleotides 1 to 17, or 2 to 18, or 3 to 19 and so forth up to a probe comprising the last 17 nucleotides of said sequences. Thus, each probe would comprise at least about 17 linear nucleotides of said sequences, designated by the formula "n to n+16," where n is an integer from 1 to an integer equal to the length of one of said sequences. Longer probes that hybridize to the nucleic acid molecules as provided herein under low, medium, or high stringency conditions are also contemplated, including those that comprise the entire nucleotide sequence of said sequences. Oligodeoxynucleotides or their analogues may be chemically synthesized, for example, by using an Applied Biosystem 380B DNA synthesizer or other suitable equipment (Applied Biosystems, Inc., Foster City, Calif.); by application of nucleic acid reproduction technology, such as the PCR technology of U.S. Pat. No. 4,683,202 (herein incorporated by reference) or by introducing selected sequences into recombinant vectors for recombinant production.

Oligonucleotide probes are useful in hybridization embodiments, such as Southern and Northern blotting. The total size of fragment, as well as the size of the complementary regions, will depend on the intended use or application of the particular nucleic acid segment. Smaller fragments will generally find use in hybridization embodiments, wherein the length of the complementary region may be varied, such as between about 20 and about 40 nucleotides, or even up to the full length of the nucleic acid as shown in said sequences according to the complementary sequences one wishes to detect.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin and digoxygenin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

Stringency conditions for hybridization depend upon a number of factors such as the length of hybridizing molecules, salt concentration, temperature, and the presence or absence of denaturing agents, for example.

High stringency conditions may include hybridization at about 42° C. and about 50% formamide, 0.1 mg/mL sheared salmon sperm DNA, 1% SDS, 2×SSC, 10% Dextran sulfate, a first wash at about 65° C., about 2×SSC, and 1% SDS, followed by a second wash at about 65° C. and about 0.1×SSC. Alternatively, high stringency conditions may include hybridization at about 42° C. and about 50% formamide, 0.1 mg/mL sheared salmon sperm DNA, 0.5% SDS, 5×SSPE, 1×Denhardt's, followed by two washes at room temperature and 2×SSC, 0.1% SDS, and two washes at between 55–60° C. and 0.2×SSC, 0.1% SDS.

Intermediate stringency conditions may include hybridization at 0–50% formamide, and varying the wash temperature between 37° C. and 65° C. and the salt between 6× and 0.1×SSC.

Low stringency hybridization conditions for detecting PAD4 genes having about 40% or greater sequence identity to the PAD4 genes described herein include, for example, hybridization at about 42° C. and 0.1 mg/mL sheared salmon sperm DNA, 1% SDS, 2×SSC, and 10% Dextran sulfate (in the absence of formamide), and a wash at about 37° C. and 6×SSC, about 1% SDS. Alternatively, the low stringency hybridization may be carried out at about 42° C. and 40% formamide, 0.1 mg/mL sheared salmon sperm DNA, 0.5% SDS, 5×SSC, 1×Denhardt's, followed by two washes at room temperature and 2×SSC, 0.1% SDS and two washes at room temperature and 0.5×SSC, 0.1% SDS. These stringency conditions are exemplary; other appropriate conditions may be determined by those skilled in the art.

Disease Resistance

Compositions of the present invention are useful for enhancing disease resistance in plants. Disease may be due to a variety of factors including pathogens and/or environmental stress, for example.

By "pathogen" is meant an organism whose infection of viable plant tissue elicits a disease response in the plant tissue. Such pathogens include, without limitation, bacteria, mycoplasmas, mycoplasmalike organisms, fungi, insects, nematodes, viruses, viroids, and oomycetes. Plant disease responses to pathogens may include those associated with systemic acquired resistance, local acquired resistance, or the hypersensitive response (or gene-for-gene resistance); alterations in gene expression, including genes encoding ribozymes, enzymes (and other protein factors) necessary for phytoalexin synthesis, osmotic potential regulation, modifications in intracellular structure, apoplastic or cell wall reorganization, cell division, apoptosis, wilting, localized necrosis, lignification, acclimation, hardening, or the like.

Examples of bacterial pathogens include, for example, Erwinia (for example, *E. carotovora*), Pseudomonas (for example, *P. syringae*), Xanthomonas (for example, *X. campepestris* and *X. oryzae*), Streptomyces (for example, *S. scabies*), Cornebacterium (for example, *C. michiganense*), and Agrobacterium (for example, *A. rubi*).

Examples of fungal disease-causing pathogens include, for example, Alternaria (for example, *A. brassicola* and *A. solani*), Ascochyta (for example, *A. pisi*), Botrytis (for example, *B. cinerea*), Cercospora (for example, *C. kikuchii* and *C. zaea-maydis*), Colletotrichum sp. (for example, *C. lindemuthianum*), Diplodia (for example, *D. maydis*), Erysiphe (for example, *E. graminis* f.sp. *graminis* and *E. graminis* f.sp. *hordei*), Fusarium (for example, *F. nivale* and *F. oxysporum, F. graminearum, F. solani, F. moniliforme,* and *F. roseum*), Gaeumanomyces (for example, *G. graminis* f.sp. *tritici*), Helminthosporium (for example, *H. turcicum, H. carbonum,* and *H. maydis*), Macrophomina (for example, *M. phaseolina* and *Maganaporthe grisea*), Nectria (for example, *N. heamatocacca*), Peronospora (for example, *P. mansurica, P. tabacina*), Phoma (for example, *P. betae*), Phymatotrichum (for example, *P. omnivorum*), Phytophthora (for example, *P. cinnamomi, P. cactorum, P. phaseoli, P. parasitica, P. citrophthora, P. megasperma* f.sp. *sojae*, and *P. infestans*), Plasmopara (for example, *P. viticola*), Podosphaera (for example, *P. leucotricha*), Puccinia (for example, *P. sorghi, P. striiformis, P. graminis* f.sp. *tritici, P. apsaragi, P. recondita,* and *P. arachidis*), Pythium (for example, *P. aphanidermatum*), Pyrenophora (for example, *P. tritici-repentens*), Pyricularia (for example, *P. oryzea*), Phytium (for example, *P. ultimum*), Rhizoctonia (for example, *R. solani* and *R. cerealis*), Scerotium (for example, *S. rolfsii*), Sclerotinia (for example, *S. sclerotiorum*), Septoria, (for example, *S. lycopersici, S. glycines, S. nodorum* and *S. tritici*), Thielaviopsis (for example, *T. basicola*), Uncinula (for example, *U. necator*), Venturia (for example, *V. inaequalis*), Verticillium (for example, *V. dahliae* and *V. albo-atrum*).

Examples of pathogenic nematodes include, for example, root-knot nematodes (for example, Meloidogyne sp. such as *M. incognita, M. arenaria, M. chitwoodi, M. hapa, M. javanica, M. graminocola, M. microtyla, M. graminis,* and *M. naasi*), cyst nematodes (for example, Heterodera sp. such as *H. schachtii, H. glycines, H. saccari, H. oryzae, H. avenae, H. cajani, H. elachista, H. goettingiana, H. graminis, H. mediterranea, H. mothi, H. sorghi,* and *H. zeae,* or, for example, Globodera sp. such as *G. rostochiensis* and *G. pallida*), root-attacking nematodes (for example, *Rotylenchulus reinformis, Tylenchuylus semipenetrans, Pratylenchus brachyurus, Radopholus citrophilus, Radpholus similis, Xiphinema americanun, Xiphinema rivesi, Paratrichodorus minor, Heterorhabditis heliothidis,* and *Bursapelenchus xylophilus*), and above-ground nematodes (for example, *Anguina funesta, Anguina tritici, Ditylenchus dipsaci, Ditylenchus myceliphagus,* and *Aphenlenchoides besseyi*).

Examples of viral pathogens include, for example, tobacco mosaic virus, tobacco necrosis virus, potato leaf roll virus, potato virus X, potato virus Y, tomato spotted wilt virus, and tomato ring spot virus.

Examples of oomycetes include, for example, Plasmopara (for example, *P. viticola* causing downy mildew of grape), Bremia (for example, *B. lactucae* causing downy mildew of lettuce), Peronospora (for example, *P. nicotianae* causing blue mold of tobacco), Sclerospora (for example, *S. gramicola* causing downy mildew of grasses), Pseudoperonospora (for example, *P. cubensis* causing downy mildew of cucurbits), Phytophthora (for example, *Phytophthora infestans* causing late blight of potato).

Deposit

Samples of *E. coli* DH5α bearing cosmid pAtgPAD4 (cosmid 8) and, separately, *E. coli* DH5α bearing cDNA clone pAtcPAD4 have been deposited with the American Type Culture Collection (ATCC) on Oct. 27, 1998, and bear the accession numbers ATCC No. 98961, and 98960, respectively. The ATCC is located at 10801 University Blvd., Manassas, Va. 20110-2209, and may be contacted by phone at (703) 365-2700. Samples of *E. coli* strain DH5α bearing pAtcPAD4.2 representing DNA isolated through PCR amplification from wild-type cDNA (corresponding to SEQ ID NO.: 54) within Bluescript SK+ plasmid were deposited with the ATCC on Oct. 25, 1999, and bear the accession number ATCC No. PTA-864. Applicants acknowledge their responsibility to replace these clones should it lose viability before the end of the term of a patent issued hereon, and their responsibility to notify the ATCC of the issuance of such a patent, at which time the deposit will be made available to the public. Prior to that time, the deposit will be made available to the Commissioner of Patents under the terms of 37 CFR §1.14 and 35 USC §112. These deposits are available as required by foreign patent laws in countries wherein counterparts of this subject application, or progeny, are filed. It should be understood that availability of a deposit does not constitute a license to practice the subject invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Phenotype Characterization of pad4 Mutant Plants

The present example provides studies that characterize the phenotype of Arabidopsis mutant plants having enhanced disease susceptibility.

Plants and Growth Conditions. Wild-type plants (*Arabidopsis thaliana* ecotype Columbia (Col)) and pad4 plants from a line that had been backcrossed four times to the wild-type parent (Col) (Glazebrook et al., 1996, Genetics 143, 973–982) were used in this study. Arabidopsis ecotype Keswick (Ksk) was provided by Eric Holub (Horticulture Research International, Warwick, UK). Arabidopsis ecotype Landsberg erecta (Ler) plants carrying the nahG transgene were provided by Xinnian Dong (Bowling et al., 1994, Plant Cell 6, 1845–1857). nahG mutant plants used in this example, and all other examples, were of the Ler ecotype. Plants were grown in pots in Metro-Mix 200 soil (Scotts-Sierra Horticultural Products Company, Marysville, Ohio) in a growth chamber (22±2° C., 85% relative humidity, 100 $\mu E$ $s^{-1}$ $m^{-2}$ fluorescent illumination) on a 12-hr light/dark cycle. Fully-expanded leaves of four-week old plants were used.

Inoculations with Bacteria and Treatment with Chemicals. *Pseudomonas syringae* pv *maculicola* (Psm) ES4326 (Dong et al., 1991, Plant Cell 3, 61–72; Crute et al., 1994, in *Arabidopsis,* eds. Meyerowitz & Somerville, Cold Spring Harbor Press, NY, pp. 705–747), *Pseudomonas. syringae* pv *tomato* (Pst) DC3000 (Cuppels, 1986, Appl. Environ. Microbiol. 52, 323–327) and *Xanthomonas campestris* pv *campestris* (Xcc) BP109 (Weiss et al., 1994, *J. Bacteriol.* 176, 3354–3359) have been described. The avirulence gene avrRpt2 was carried on plasmid pLH12 as described (Dong et al., 1991, Plant Cell 3, 61–72; Whalen et al., 1991, Plant Cell 3, 49–59). *P. syringae* strains were grown in King's B medium supplemented with appropriate antibiotics (Glazebrook and Ausubel, 1994, Proc. Natl. Acad. Sci. USA 91, 8955–8959), and Xcc BP1 09 was grown in Luria-Bertani medium supplemented with 50 $\mu$g/mL rifampicin. Bacteria were infiltrated into Arabidopsis plants as described (Glazebrook and Ausubel, 1994, PNAS USA 91, 8955–8959; Glazebrook et al., 1996, Genetics 146: 381–392). For camalexin assays, the bacterial dose for *P. syringae* strains was $3\times10^4$ colony-forming units (cfu)/$cm^2$ leaf area (equivalent to $OD_{600}$=0.006); for Xcc BP109 it was $5\times10^5$ cfu/$cm^2$ ($OD_{600}$=0.1). For experiments involving extraction of total RNA from infected leaves, Psm ES4326 and Psm ES4326 carrying avrRpt2 were introduced at a dose of $10^4$ cfu/$cm^2$ leaf area (equivalent to $OD_{600}$=0.002). For determination of Psm ES4326 growth, plants were infected with Psm ES4326 at a dose of $10^3$ cfu/$cm^2$ leaf area (equivalent to $OD_{600}$=0.0002). After 3 leaves were excised and bacterial growth was assayed as described (Glazebrook et al., 1996, Genetics 143, 973–982). Data are reported as means and standard deviations of the log(cfu/$cm^2$) of six replicates. For chemical treatment, plants were sprayed with 5 mM SA or 5 mM silver nitrate with 0.02% Silwet L-77 (Lehle Seeds, Tucson, Ariz.) to reduce surface tension. Control plants were sprayed with water containing 0.02% Silwet L-77.

Phytoalexin Quantitation. 1. Camalexin. For *P. syringae*-infected leaves, fresh weight changes markedly over the course of infection due to water loss from the infected tissue. Therefore, for *P. syringae*-infected leaves, samples consisted of four leaf discs cut with a number 3 cork borer (1.1 $cm^2$ total), and camalexin concentrations were normalized to leaf area. For leaves infected with Xcc BP109 or treated with silver nitrate, samples consisted of approximately 100 mg of tissue, and camalexin concentrations were normalized to fresh weight. Camalexin assays were performed as described (Glazebrook et al., 1996, Genetics 143: 973–982). Plants were infected with Psm ES4326 at a dose of $10^5$ cfu/$cm^2$ leaf area, and 36–48 hr later camelexin was extracted from infected tissue and visualized on thin layer chromatography plates under long-wave ultra-violet illumination as described previously (Glazebrook and Ausubel, 1994, Proc. Natl. Acad. Sci. USA 91: 8955–8959). For each data point, the results are reported as the mean and standard deviation from six replicates.

2. Other phytoalexins include pisatin (for example, from pea, *Pisum sativum*), glycollin, medicarpin, cyclobrassinin, methoxybrassinin, brassinin, resveratrol, dianthalexin, phaseollin, ipomeamarone, orchinol, rishitin, coumestrol, kievitone, capsidiol, lubimin, 3-hydroxylubimin, and debneyol. The antimicrobial activity of phytoalexins is assayed on thin-layer chromatography (TLC) plates in the presence of 2,3,5-triphenyl-tetrazolium chloride (TZC) using, for example, a bacterium such as *Pseudomonas syringae* pv *phaseolicola* as the indicator organism (Slusarenko, A J et al., 1989, Botanica Helvetica 99(2):203–207). Fairly crude plant extracts developed on TLC plates can be assayed without significant apparent interference from plant pigments or other endogenous substances. After applying a bacterial suspension in an agar medium to the TLC plates, areas where bacterial growth have been inhibited by phytoalexins are indicated by pale spots against a deep pink-red background (Slusarenko, A J et al., 1989, Botanica Helvetica 99(2):203–207).

Isolation of a pad4 mutants. The pad4-1 mutant was isolated in a screen for mutants that demonstrated enhanced disease susceptibility (eds mutants) when infected with Psm ES4326. Plants were infected with a very low dose of Psm ES4326, such that wild-type plants did not develop the chlorotic lesions characteristic of Psm ES4326 infection, but several mutant plants did develop lesions. Characterization of one of these mutants revealed that it synthesized reduced levels of camalexin in Psm ES4326-infected leaves, and that it complemented all other camalexin-deficient mutants, so it was named pad4 (Glazebrook et al., 1996, Genetics 143: 973–982). In bacterial growth assays, the maximal titer of Psm ES4326 in pad4 plants was 100-fold higher than in wild-type plants. When plants were challenged with Psm ES4326 carrying the avirulence gene avrRpt2, both wild-type and pad4 plants showed the hypersensitive response, and growth of the avirulent strain was greatly reduced relative to the isogenic virulent strain, demonstrating that pad4 plants are not significantly compromised in gene-for-gene resistance triggered by avrRpt2 (Glazebrook et al., 1997, Genetics 146:381–392). Studies described herein were carried out using this pad4 allele, termed pad4-1.

Drs. Louise Frost and Jane Parker (The Sainsbury Laboratory, Norwich Research Park, Colney, Norwich, UK) isolated the pad4-2 mutant from fast neutron mutagenized Landsberg erecta (Ler) seed (Lehle Seeds, Round Rock, Tex.) in a screen for suppressors of RPP5-mediated resistance to *Peronospora parasitica* (Parker et al., 1996, Plant Cell 8:2033–2046). F1 and F2 complementation testing by Drs. Frost and Parker revealed that pad4-2 was allelic to pad4-1. Drs. Frost and Parker kindly provided pad4-2 seed to Dr. Jane Glazebrook.

Drs. T. Lynne Reuber and Frederick M. Ausubel (Massachusetts General Hospital, (Boston, Mass.) identified pad4-3 and pad4-4 plants in the Columbia ecotype in a screen for plants with enhanced susceptibility to the fungal pathogen *Erisyphe orontii*. The screen was carried out by inoculating 4½-week-old M2 Arabidopsis plants grown from fast neutron mutagenized seed pools (Lehle Seeds, Round Rock, Tex.) with *E. orontii* conidia as described (Reuber et al., 1998, Plant J. 16:473–485). Complementation testing by Drs. Reuber and Ausubel revealed that pad4-3 and pad4-4 were allelic to pad4-1. Drs. Reuber and Ausubel kindly provided pad4-3 and pad4-4 seed to Dr. Jane Glazebrook.

PAD4 Functions in Regulation of Camalexin Synthesis. The previous demonstration that pad4 plants show a defect in camalexin synthesis in response to infection by the virulent bacterial pathogen *P. s. maculicola* ES4326, but not in response to challenge by the non-host fungal pathogen *C. carbonum* (Glazebrook et al., 1997, Genetics 146:381–392), led the present inventors to examine the effect of pad4 on camalexin synthesis in response to various elicitors. Wild-type and pad4-1 plants were infected with Psm ES4326 or an isogenic strain carrying the avirulence gene avrRpt2. Camalexin levels in the infected leaves were determined at various intervals after infection. FIG. 1A shows that when plants were infected with Psm ES4326, camalexin levels in wild-type plants were much higher than those in pad4-1 plants. In contrast, when plants were infected with Psm ES4326 carrying avrRpt2, camalexin levels in wild-type and pad4-1 plants were not significantly different. Similar results were obtained using a different virulent *P. syringae* strain, Pst DC3000, and Pst DC3000 carrying avrRpt2. This result suggests that the signal transduction pathway leading to camalexin synthesis in response to Psm ES4326 or Pst DC3000 infection requires PAD4, whereas camalexin synthesis in response to strains carrying avrRpt2 is mediated by a PAD4-independent pathway. Two other treatments known to trigger camalexin synthesis are infection with Xcc BP109 and spraying with silver nitrate. FIG. 1B and FIG. 1C show that pad4-1 did not affect camalexin synthesis in response to either of these treatments, suggesting that responses to these stimuli are also independent of PAD4.

RNA Blot Analysis. Tissue samples consisting of 3–5 leaves were collected and frozen in liquid nitrogen and stored at −80 ° C. Total RNA was extracted and 5 $\mu$g of RNA per sample was separated on formaldehyde-agarose gels. After blotting onto Hybond-N$^+$ membrane (Amersham, Arlington Heights, Ill.), hybridizations were performed using various digoxigenin-labeled probes, followed by washes in 0.5×SSC (1×SSC is 0.15 M NaCl and 0.015 sodium citrate) at 65° C. and chemiluminescent detection with CSPD according to instructions provided by the supplier (Boehringer Mannheim, Indianapolis, Ind.). For hybridization with more than one probe, blots were stripped and reprobed. Single-stranded DNA probes were prepared by amplification of appropriate sequences from cDNA clones (PR-1 and PR-5; Uknes et al., 1992, Plant Cell 4: 645–656) and from plasmid pATBG12 (BGL2; Dong et al., 1991, Plant Cell 3: 61–72) as previously described (Glazebrook et al., 1996) except that digoxigenin-11-dUTP was used as the label, according to the instructions of the supplier (Boehringer Mannheim). For the ASA1 probe, a single-stranded probe was made from plasmid pKN41 (Niyogi and Fink, 1992, Plant Cell 4, 721–723) using sense and antisense primers (Zhou et al., 1998, Plant Cell 10:1021–1030). Blots were stripped and reprobed with the 18S rRNA probe to assess equal loading of RNA samples. RNA blot analyses with PAD4 probes are provided in Example 12, infra.

Expression of the Defense Gene PR-1 is Impaired in pad4 Plants. The finding that PAD4 is required for activation of camalexin synthesis in response to infection by Psm ES4326 raised the possibility that PAD4 might encode a pleiotropic regulator of defense responses. To test whether pad4 affects activation of other defense responses in addition to camalexin synthesis, mRNA levels of several defense-related genes were examined by RNA gel blot hybridization. FIG. 2A shows that the mRNA levels of PR-1 were greatly reduced in infected pad4-1 leaves relative to the levels in wild-type plants. Expression of PR-5, BGL2, and ASA1 were essentially unaffected by the pad4-1 mutation. ASA1 encodes anthranilate synthase, which is required for camalexin synthesis since anthranilate is a precursor to camalexin. A tight correlation was previously observed between camalexin levels and ASA1 expression, however, this correlation is not maintained in pad4-1 plants. Clearly, pad4 has effects on defense gene expression, but these effects are not consistent among all genes induced by Psm ES4326 infection.

Infection with Psm ES4326 carrying avrRpt2 also leads to increases in expression of defense genes, including PR-1 (Greenberg et al., 1994, Cell 77: 551–563). However, FIG. 2B shows that PR-1 mRNA levels in plants infected with Psm ES4326 carrying avrRpt2 were unaffected by pad4-1. Taken together, the results of FIG. 1A and FIG. 1B show that host defense responses to Psm ES4326 carrying avrRpt2 are largely PAD4 independent.

Determination of endogenous levels of salicylic acid (SA) and salicylic acid glucoside (SAG). Mature leaves of 4 week-old wild-type and pad4-1 plants were infected with Psm ES4326 at a dose of $10^4$ cfu/cm$^2$ (equivalent to OD$_{600}$= 0.002) or mock infected with 10 mM MgSO$_4$. At intervals after infection, samples were collected (1 g of tissue per sample, from approximately 7 plants) and frozen in liquid nitrogen. SA and SAG were determined as described (Bowling et al., 1994, Plant Cell 9: 1573–1584). Raw data were multiplied by 2 to reflect 50% recovery of SA and SAG in this assay.

Signaling downstream from SA is not affected by pad4. It is known that SA is required for induction of PR-1 gene expression in infected leaves. SA treatment is also sufficient for induction of PR-1 gene expression and SAR. To determine whether pad4 affects responses to SA, pad4-1 plants were treated with SA and tested for increased PR-1 gene expression and enhanced pathogen resistance. Wild-type and pad4-1 plants were sprayed with SA, and PR-1 mRNA levels were monitored for several days. FIG. 3A shows that SA treatment induced similar levels of PR-1 expression in wild-type and pad4-1 plants, with PR-1 mRNA present at high levels one day after treatment and declining thereafter. The effect of SA on pathogen growth was tested by infecting plants with Psm ES4326 one day after plants were sprayed with either 5 mM SA or water and measuring bacterial titer three days after infection. FIG. 3B shows that SA treatment induced comparable levels of resistance to Psm ES4326 in wild-type and pad4-1 plants. Based on these experiments, the signal transduction pathway between SA and PR-1 expression appears intact in pad4-1 plants, suggesting that PAD4 acts elsewhere in controlling PR-1 gene expression.

SA Accumulation in Response to Psm ES4326 Infection is Reduced in pad4 Plants. SA is required for both PR-1 gene expression and for camalexin synthesis. In the case of PR-1, SA is both necessary and sufficient for increased PR-1 expression in response to pathogen attack. In the case of camalexin accumulation, SA is not sufficient, since SA treatment does not lead to significant camalexin accumulation. However, SA is required, because nahG-transgenic plants fail to accumulate camalexin in response to *P. s. maculicola* ES4326 infection. The accumulation of camalexin in wild-type and nahG plants infected with Psm ES4326 or Psm ES4326 carrying avrRpt2 was tested. As shown in FIG. 4, camalexin levels in nahG plants infected with either pathogen were much lower than in wild-type plants. Thus, SA is required for full induction of camalexin synthesis in response to either Psm ES4326 or Psm ES4326 carrying avrRpt2.

Whether pad4 plants have a defect in SA accumulation in response to Psm ES4326 infection, thereby resulting in reduced camalexin synthesis and reduced PR-1 expression, was tested. Wild-type and pad4-1 plants were infected with Psm ES4326, or Psm ES4326 carrying avrRpt2, and both SA and SAG were monitored over the course of the infection. FIG. 5A shows that the SA levels in pad4-1 plants infected with Psm ES4326 were much lower than the levels in infected wild-type plants at all time points tested. In wild-type plants, SA levels were highest at 12 hr after infection, whereas in pad4-1 plants, SA levels were highest at 24 hr after infection. FIG. 5C shows that after infection with Psm ES4326, SAG levels were greatly reduced in pad4-1 plants. In contrast, when plants were infected with Psm ES4326 carrying avrRpt2, there was very little difference between SA levels in pad4-1 and wild-type plants, as shown in FIG. 5B. The data of FIG. 5D shows that after infection with Psm ES4326 carrying avrRpt2, the SAG levels in pad4-1 plants were significantly lower than those in wild-type plants, but these differences were not as large as those observed in Psm ES4326-infected plants (FIG. 5C). These findings suggested that pad4 plants have a defect in SA accumulation in response to Psm ES4326 infection, and that this leads to reduced PR-1 expression and camalexin synthesis.

Exogenous SA Restores Camalexin Accumulation and PR-1 Expression in Psm ES4326-Infected pad4 plants. If the defects in SA accumulation in response to Psm ES4326 infection observed in pad4 plants are the cause of the camalexin accumulation and PR-1 gene expression defects, then it should be possible to restore camalexin synthesis and PR-1 gene expression to Psm ES4326-infected pad4 plants by supplying them with SA. To test for rescue of the camalexin deficiency of pad4 plants by SA treatment, wild-type and pad4-1 plants were sprayed with water or SA, and then infected with Psm ES4326 one day later. Camalexin levels (were assayed two days after infection. FIG. 6A shows that pad4-1 plants treated with SA prior to infection displayed much higher camalexin levels than did pad4-1 plants that were not pretreated with SA. In the study shown in FIG. 6A, SA treatment of wild-type plants had little effect on camalexin levels. The reversal of the camalexin-deficient phenotype of pad4-1 plants by SA treatment provides strong evidence that the camalexin deficiency caused by pad4-1 results from failure to accumulate sufficient SA for activation of camalexin synthesis.

The possibility that SA treatment might also rescue the PR-1 gene expression defect of pad4 plants was tested. Wild-type and pad4-1 plants were sprayed with either 5 mM SA or with water. After one day, plants were infected with Psm ES4326, and PR-1 mRNA levels were assessed two days after infection. FIG. 6B shows that one day after SA treatment, PR-1 mRNA levels were elevated in both wild-type and pad4-1 plants (lanes 2 and 6). In the absence of Psm ES4326 infection, two days after treatment the PR-1 mRNA levels in both genotypes had declined to barely detectable levels. In plants that were treated with SA prior to infection, the PR-1 mRNA level in pad4-1 plants was comparable to that in wild-type plants (FIG. 6B, lanes 4 and 8). The PR-1 expression in SA-treated, Psm ES4326-infected pad4-1 plants cannot be solely due to the SA treatment, since the PR-1 mRNA level in pad4-1 plants treated only with SA had declined by two days after treatment. Rather, the SA treatment must have restored the ability of the pad4-1 plants to respond to Psm ES4326, demonstrating that the PR-1 gene expression defect caused by pad4-1 is also reversed by SA treatment. The observations that SA treatment can reverse the camalexin accumulation and PR-1 gene expression defects of Psm ES4326-infected pad4-1 plants provide strong support for the idea that the alteration in SA accumulation in pad4 plants is the cause of the defects in camalexin synthesis and PR-1 gene expression.

Responses to avirulent pathogens expressing avrRpt2 do not require PAD4. When pad4-1 plants were infected with the avirulent pathogen Psm ES4326 carrying avrRpt2, camalexin synthesis, PR-1 expression, and SA accumulation were all indistinguishable from responses in wild-type plants. Clearly, PAD4 does not play a crucial role in activating these defenses in response to Psm ES4326 carrying avrRpt2. That pad4-1 mutants are susceptible to *Peronospora parasitica* isolates that are avirulent on wild-type Col plants (Glazebrook et al., 1997, Genetics 146:381–392) is known. Therefore, PAD4 function is required in some gene-for-gene resistance responses, but not all.

Not wanting to be bound by theory, the present inventors provide FIG. 7 as a working model of the role of PAD4 in defense response signaling. When plants are infected with Psm ES4326, PAD4 is needed for SA concentrations to reach the level required for camalexin synthesis and expression of PR-1. In contrast, when plants are infected with Psm ES4326 carrying avrRpt2, SA accumulates in a PAD4-independent manner. For PR-1 expression, activation of the SA pathway is sufficient, but camalexin synthesis requires a signal from another pathway as well.

EXAMPLE 2

Molecular Mapping of PAD4

The present example provides molecular mapping of the PAD4 gene using a technique called positional cloning (also called "map-based cloning" or "chromosome-walking"). In general, the gene is obtained by determining its genetic map position at high resolution, isolating all of the DNA lying between the positions of the two closest genetic markers flanking the gene of interest, introducing various fragments of this DNA into mutant plants to locate the sequences that complement the mutant phenotype, and determining the sequence of the complementing DNA from wild-type and mutant plants. The correct gene must complement the mutant phenotype and contain alterations in mutant plants. In particular, pad4-1 and PAD4 genes were mapped using Cleaved Amplified Polymorphic Sequence (CAPS) markers (Konieczny and Ausubel, 1993, Plant J. 4: 403–410) derived from clones of Arabidopsis chromosome #3 loci such as g11, TOPP5, m409, m457, 7A4R, and AtEm1 (GenBank Accession # Z 11158) (FIGS. 8 and 18A), as well as from ends of YACs CIC7A4, CIC9D9, and yUP1E3, as detailed infra.

Low-resolution mapping of PAD4. Ecotype Keswick (Ksk) was chosen for mapping because it has many DNA sequence polymorphisms relative to Columbia, and because it was not possible to use a more common ecotype, Landsberg, because the camalexin deficient phenotype of pad4-1 plants shows aberrant segregation in crosses to Landsberg. Homozygous pad4-1 mutant plants (ecotype Columbia) were crossed to wild-typePAD4 plants of the Keswick ecotype. The F1 progeny were allowed to self, and F2 plants were assayed for camalexin deficiency in response to infection by Psm ES4326 to identify pad4-1 homozygotes. Among 251 plants tested, 58 were camalexin deficient (Pad⁻), in accordance with the expected 3:1 ratio for segregation of a recessive allele of a single-copy gene.

Cleaved Amplified Polymorphic Sequence (CAPS) markers (Konieczny and Ausubel, 1993, Plant J. 4: 403–410), were used to map pad4-1 (and PAD4). CAPS markers are restriction fragment length polymorphisms (RFLPs) that are detected by restriction enzyme digestion of small DNA fragments generated by PCR. A large number of these markers have been described, and a list curated by Dr. Frederick M. Ausubel and staff is publicly available from the Arabidopsis database (http://genome-www.stanford.edu/Arabidopsis/aboutcaps.html). For some markers, it was necessary to identify a restriction enzyme that detected a polymorphism between Col and Ksk, as Ksk is not a commonly used ecotype. A list of all CAPS markers used in this project is provided in Table 2.

TABLE 2

CAPS Markers

| Marker | Primer Sequences | SEQ ID NO: | Enzyme Showing Polymorphism |
|---|---|---|---|
| g11 | 5'-ATATTGAGTACTGCCTTTAG-3' | 34 | TaqI |
|  | 5'-CCATGATCCGAAGAGACTAT-3' | 35 |  |
| TOPP5 | 5'-TCGACGACATCATTCGTCGT-3' | 36 | RsaI |
|  | 5'-GAACTGAAGCATCCTGCAGT-3' | 37 |  |
| m409 | 5'-CATAACTCGTTATTGAAAAAGGGC-3' | 38 | EcoRV |
|  | 5'-CCCACTAGATCGTCACACT-3' | 39 |  |
| m457 | 5'-CTTCGCATCAGGAAGGAATT-3' | 40 | HinfI |
|  | 5'-GATCAACTGCTATGATAGCTACG-3' | 41 |  |
| 7A4R | 5'-CCACACCGGGAAAGTGATGGAGTTCGC-3' | 42 | HaeIII |
|  | 5'-TGTTGCTGATCACCGGTCGGTCAGGG-3' | 43 |  |
| AtEM1 | 5'-CAGGAGAGGTAAGACTCAGCTCCTTCTCG-3' | 44 | AflIII |
|  | 5'-CATCTGGGAAACCTTATTATGCGTTGGCG-3' | 45 |  |
| 1E3L | 5'-TCGCCTTTGACCCAACACAGAGATGTC-3' | 46 | BsrBI |
|  | 5'-CTGAAGGGAAGCGAATATCCTCATTCTC-3' | 47 |  |
| 9D9L | 5'-CTCAATGTCTGGCAGCTTTCTGGGATGC-3' | 48 | HinfI |
|  | 5'-CAATTCCGATGTAGTGACCAATCGGAGC-3' | 49 |  |
| AFC1 | 5'-GGAACTCTCAAGTCTAAACAG-3' | 50 | PvuII |
|  | 5'-AGCTTTATCACGATACACACTGC-3' | 51 |  |
| BGL1 | 5'-TCTTCTCGGTCTATTCTTCG-3' | 52 | RsaI |
|  | 5'-TTATCACCATAACGTCTCCC-3' | 53 |  |

DNA was prepared from 34 Pad⁻ F2 plants, and the genotypes of these plants at CAPS markers NCC1, g11447, and ADH on chromosome #1, GPA1 on chromosome #2, GL1 and BGL2 on chromosome #3, AG on chromosome #4, and PHYC on chromosome #5 were determined. Linkage of pad4-1 to markers GL1 (17 recombination events among 68 chromosomes, 25%) and BGL2 (9 recombination events among 68 chromosomes, 13%) was observed, demonstrating that pad4-1 lies between GL1 and BGL2 on chromosome #3.

High-resolution mapping of PAD4. Additional markers lying between GL1 and BGL2 were identified by examination of the list of CAPS markers and the Lister and Dean recombinant inbred map publicly available at: http://genome-www3.stanford.edu/cgi-bin/AtDB/RIintromap. TOPP5 and AFC1 were CAPS markers. m457 and m409 are plasmids that can be used to detect RFLP markers that we converted to CAPS markers by obtaining the plasmids from the Arabidopsis Biological Resource Center (ABRC) at Ohio State Univeristy (Columbus, Ohio), sequencing the ends, designing suitable oligonucleotide primers, using these for PCR amplification of DNA fragments from Col and Ksk, and screening a panel of restriction enzymes for those that detected a polymorphism between Col and Ksk. The position of pad4-1 relative to these markers was determined using large numbers of Pad⁻ F2 plants from the mapping cross. For TOPP5, there were 31 recombination events among 242 chromosomes (12.8%). All of the chromosomes tested that had recombination events between TOPP5 and pad4-1 ("TOPP5 recombinants") were GL1 recombinants, while none of the TOPP5 recombinants were BGL2 recombinants, indicating that pad4-1 lies between TOPP5 and BGL2. For m409, there were 46 recombination events among 362 chromosomes (12.7%). All of the m409 recombinants tested were also TOPP5 recombinants, while none were BGL2 recombinants, indicating that pad4-1 lies between m409 and BGL2. For AFC1, there were 11 recombination events among 622 chromosomes (1.7%). All of the AFC1 recombinants were BGL2 recombinants, while none of them were m409 recombinants, indicating that pad4-1 lies between m409 and AFC 1. For m457, there were 10 recombination events among 624 chromosomes. All of the m457 recombinants were also m409 recombinants, while none were AFC1 recombinants, indicating that pad4-1 lies between m457 and AFC1.

Locating PAD4 on the physical map. Dr. David Bouchez provided the present inventors with a description of an alignment of YACs (Yeast Artificial Chromosome clones of Arabidopsis genomic DNA) that spanned marker m457, but did not extend as far as marker AFC1 (Camilleri et al., 1998, Plant J 14:633–642). Relevant parts of this map are shown in FIG. 8 (and in FIG. 18A). YAC clones CIC7A4, CIC9D9, and yUP1E3 were obtained from the ABRC. Several markers were generated for mapping PAD4 within the physical map. CAPS markers were generated from the ends of YAC clones by cloning the ends of the YACs using a modification of the adaptor-ligation PCR method (Siebert et al., 1995, Nucleic Acid Res. 23: 1087–1088), sequencing the cloned ends, designing primers, amplifying the corresponding DNA from Col and Ksk, and screening a panel of restriction enzymes for those that detected polymorphisms. Marker AtEM1 represents a sequenced Arabidopsis gene. The sequence was obtained from GenBank and used to generate a CAPS marker as described above for cloned YAC ends.

For marker 7A4R, there were 8 recombination events among 624 chromosomes (1.3%). All of the 7A4R recombinants were also m457 recombinants, while none were AFC1 recombinants, indicating that pad4-1 lies between 7A4R and AFC1. For 1E3L, there were 5 recombination events among 624 chromosomes (0.8%). All of the 1E3L recombinants were also AFC1 recombinants, while none of them were 7A4R recombinants, indicating that pad4-1 lies between 7A4R and 1E3L, within the interval covered by the physical map. For AtEm1, there were 5 recombination events among 624 chromosomes (0.8%). All of the AtEm1 recombinants were also 7A4R recombinants, while none of them were 1E3L recombinants, indicating that pad4-1 lies between AtEm1 and 1E3L. For 9D9L, there was one recombination event among 624 chromosomes. This recombinant was also an AtEM1 recombinant, but was not a 1E3L recombinant, indicating that pad4-1 lies between 9D9L and 1E3L.

Locating PAD4 within a BAC contig. The position of PAD4 was further defined using BACs (bacterial artificial chromosome clones of Arabidopsis genomic DNA). Hybridization filters carrying a BAC library were obtained from the ABRC. Hybridization with a 9D9L probe identified BACs T8N21 and T5I22. Hybridization with 1E3L identified BACs T3P23 and T4C16. BACs T2O16, T14I23 and T18L3 that completed the BAC contig were obtained using the BAC fingerprint database at http://genome.wustl.edu/gsc/arab/arabidopsis.html (FIG. 9; see also, FIG. 18A and FIG. 18B). Markers T8N21R and T5I22L were obtained by cloning the BAC ends as described above for YAC ends, and using the clones as hybridization probes on a DNA blot of Col and Ksk DNA digested with various enzymes to identify RFLPs. An RFLP for mi456 was found by obtaining the mi456 plasmid from the ABRC and using it as a hybridization probe. The 9D9l and 1E3L recombinants were tested to determine their genotypes at these markers. For mi456, there were 3 recombination events. The mi456 recombinants were also 1E3L recombinants while none of them were 9D9L recombinants, indicating that pad4-1 lies between 9D9L and mi456. For T5I22L, there was one recombination event. This recombinant was also a mi456 recombinant, but was not a 9D9L recombinant, indicating that pad4-1 lies between 9D9L and T5I22L. For T8N21R, there was one recombination event. This recombinant was the 9D9L recombinant, but was not the T5I22L recombinant, indicating that pad4-1 lies between T8N21R and T5I22L, and that PAD4 must lie within T5I22. That is, mapping in particular with RFLP markers derived from the right end of BAC T8N21 (T8N21R) and left end of T5I22 (T5I22L) revealed that PAD4 lies on BAC T5I22.

EXAMPLE 3

Identification and Nucleic Acid Sequence of a Cosmid Insert Containing PAD4; Encoded Protein Sequence of PAD4 and pad4

The present example provides the identification and nucleic acid sequence of an 11.168 kb region of Arabidopsis DNA that contains a region having complementing activity for the pad4 mutation.

Construction of the Cosmid Contig Spanning PAD4 and Identifiying PAD4. BAC clone T5I22 was subcloned into binary cosmid vector pCLD04541 (Bent, et al., 1994, Science 265:1856–1860. More particularly, BAC DNA was purified on a CsCl gradient (Siebert and Chenchik, 1995, Nucleic Acid Res. 23: 1087–1088) and partially digested with TaqI. The fragments were cloned into the ClaI site of the binary vector pCLD04541 (Bent et al., 1994, Science 265: 1856–1869).

The cosmid clones were packaged into bacteriophage lambda particles using the Gigapack XL kit from Stratagene (La Jolla, Calif.). Thirty-six randomly-chosen cosmids from the library were aligned into a contig using BAC end probes T8N21R, T5I22L and inserts from cosmids which hybridized to these two probes. DNA preparations from cosmids which complemented the camalexin-deficient phenotype of pad4-1 were analyzed by EcoRI, HindIII and BamHI digestion followed by Southern hybridization with probes made from different fragments of cosmid #8. A restriction map of the cosmids was then constructed.

A cosmid contig spanning BAC T5I22 was assembled by hybridization of cosmids with each other and with T5I22L (FIG. 12; see also, FIG. 18B) using DNA blot hybridization. Various cosmids were used to transform pad4-1 mutant plants using a modified vacuum infiltration protocol (Bechtold et al., 1993, C.R. Acad. Sci. Paris, Life Sciences 316: 1194–1199). In particular, twenty cosmids that collectively contained all of the BAC DNA were used to transform pad4-1 plants and the transfomants were tested for complementation of the camalexin-deficient phenotype of pad4-1 after PsmES4326 infection. Thirteen cosmids, including cosmids #6 and #15 (see FIG. 18B), failed to complement. However, plants transformed with cosmids #8 (termed pAtgPAD4), #21, and #23, among others (see FIG. 18B), produced wild-type levels of camalexin, indicating that PAD4 must lie in sequences common among these three cosmids. Cosmid #8 was the smallest of the three cosmids (i.e, cosmids #8, #21, and #23), carrying 11.168 kb of Arabidopsis DNA. This DNA was entirely sequenced and is provided as SEQ ID NO.:5. The sequence was compared with GenBank using BLAST, and two regions with homology to known genes were identified. One region (for example, nucleotides 3112 to 3267) had homology to certain lipases, while the other (nucleotides 5637–5816) contained a zinc-finger motif (FIG. 12). The region containing homology to lipases was contained in cosmids #21 and #23. Restriction mapping of cosmid #23 revealed that the Arabidopsis DNA in cosmid #23 ended approximately 600 nucleotides to the right of the HindIII site at nucleotide 4138 in cosmid #8, demonstrating that the zinc-finger gene was not contained in cosmid #23. Since all of the complementing cosmids contained the lipase-like gene, but they did not all contain the zinc-finger gene, the lipase-like gene was identified as PAD4. Furthermore, a 5.6 kb BamHI fragment from cosmid #8 (FIG. 18B) also complemented the camalexin-deficient phenotype of pad4-1, demonstrating that this fragment contains PAD4.

DNA Sequence Analysis. Fragments obtained from EcoRI and HindIII digests of cosmid #8 were subcloned into pBLUESCRIPT SK(+) (Stratagene, La Jolla, Calif.). These subcloned fragments were then sequenced using an ABI automated sequencer. Furthermore, in order to analyze mutant alleles, PAD4 sequences were amplified from wild-type and pad4 mutant (pad4-1, pad4-2, pad4-3, and pad4-4) plants and sequenced directly. In particular, the 5.6 kb BamHI region of genomic DNA from wild-type (Col), Landsberg erecta (Ler), and all four mutant (pad4-1, pad4-2, pad4-3, and pad4-4) plants was amplified, and the DNA sequence of the amplified products determined.

The sequence data were analyzed using the software DNA Star (Lasergene) (www.dnastar.com; Madison, Wis.) and DNA Strider. Sequence data were also submitted for a BLAST (Altschul et al., 1990, J. Mol. Biol. 215:403–10) search of all public databases. Multiple sequence alignment of the predicted protein sequences was performed using the CLUSTALW(1.73) Program at http://transfac.gbf.braunschweig.de/dbsearch/clustalw.html. The predicted protein sequence showed similarity to lipases and other esterases.

Each mutant allele had a single mutation in the 5.6 kb BamHI region of the genomic DNA, and, each of these mutations lay in the predicted open reading frame of the lipase-like gene, demonstrating that it encodes a PAD4 protein.

Isolation of a PAD4 cDNA Clone. A cDNA clone of the lipase-like gene was obtained using the Marathon kit (Clontech) for PCR cloning of cDNAs. The template was made from mRNA prepared from PsmES4326-infected wild-type Columbia plants. Again, Arabidopsis DNA of the genomic clone (termed pAtgPAD4) from cosmid #8 was 11.168 kb having the sequence provided as SEQ ID NO.: 5. The cDNA clone (termed pAtcPAD4) was approximately 1,722 bp_in length and is provided as SEQ ID NO.: 1. Examination of the sequence of the genomic clone revealed the existence of an in-frame ATG codon seven bases upstream from the 5'-end of the cDNA represented in SEQ ID NO.:1. A second cDNA clone (termed pAtcPAD4.2) representing DNA amplified from wild-type cDNA of a sequence corresponding to SEQ ID NO.:54 (and representing DNA which includes the upstream ATG codon) was prepared following the procedure presented in Example 11, infra. Determination of the nucleotide sequences of the cDNA clones and comparison of the cDNA and genomic sequences revealed that the PAD4 gene contained a single intron of 1.1 kb between nucleotides 281 and 282 of the pAtcPAD4 cDNA of SEQ ID NO.:1 (and between nucleotides 291 and 292 of the pAtcPAD4.2 cDNA of SEQ ID NO.: 54).

Unambiguous identification of PAD4 using mutant alleles. The molecular nature of each pad4 mutation, identified using cDNA residue positions corresponding to those of SEQ ID NO. 54, is presented in Table 3. The sequencing results were consistent with the reasoning that if the lipase-like gene is PAD4, it must contain mutations in pad4 mutant plants. Consequently, the gene from which the cDNAs are transcribed is the PAD4 gene.

TABLE 3

Molecular nature of pad4 mutations:

| Allele | Base Change from PAD4 | Amino Acid Change to Stop |
|---|---|---|
| pad4-1 (as in SEQ ID NO.:3) | G1066 to A | W344 to stop |
| pad4-1 (as in SEQ ID NO.:56) | G1076 to A | W359 to stop |
| pad4-2 (as in SEQ ID NO.:58) | Insertion of T at T430 | R182 to stop |
| pad4-3 (as in SEQ ID NO.:60) | C1156 to T | Q386 to stop |
| pad4-4 (as in SEQ ID NO.:62) | Deletion of G1537 | L516 to stop |

The predicted PAD4 protein has significant homology with certain triacyl glycerol lipases and an esterase. An alignment of the PAD4 sequence with those of some of these enzymes is shown in FIG. 11A and FIG. 11B, as well as in FIG. 19A, FIG. 19B, and FIG. 19C. This homology suggests that PAD4 controls expression of defense responses by synthesizing or destroying a signal molecule by hydrolysis.

FIG. 19A, FIG. 19B, and FIG. 19C show more completely alignments of the N-terminal region of PAD4 with these lipases and an esterase. While the overall amount of amino acid identity of PAD4 to the lipases is relatively low (27–35%), PAD4 is as similar to any of these known lipases as they are to each other (FIG. 19A–FIG. 19C). The region similar to lipases includes three conserved amino acid residues: a serine (FIG. 19A), an aspartate (FIG. 19B), and a histidine (FIG. 19C). The corresponding residues in a triacylglycerol lipase from Mucor miehei have been shown, using X-ray crystallography (Brady et al., 1990, 343: 767–770), to form a catalytic triad. The COOH-terminal sequence of 360 amino acids did not show significant sequence similarity to any known protein. However, since the pad4-1 mutation causes truncation of much of this region of the PAD4 protein, the C-terminal region must be essential for PAD4 activity.

Lipases are hydrolytic enzymes that break down triacylglycerols into fatty acids and glycerol and operate at the surface of emulsified substrates. It has been shown that diacylglycerol, a lipid molecule, is capable of activating protein kinase C in vitro and in vivo (Go et al., 1987, Biochemical and Biophysical Research Communications 144: 598–605). The activation of protein kinase C is required to modulate many $Ca^{2+}$-dependent cellular processes (Nishizuka, 1986, Science 223: 305–312). In addition, interleukin 4 has been found to induce a lipase in cytotoxic T lymphocytes (CTLs); the activity of the induced lipase may be involved in the effector function of CTLs (Grusby et al., 1990, Cell 60: 451–459). It is possible that the function of PAD4 is associated with a lipolytic activity that gives rise to or degrades a molecule involved in signal transduction pathways leading to disease resistance.

However, PAD4 is also similar to ferulic acid esterase from Aspergillus niger (FIG. 11A, FIG. 11B, FIG. 19A, FIG.

19B, and FIG. 19C). Consequently, it is also possible that PAD4 acts on a substrate that is non-lipid in nature, such as ferulic acid.

While it is also entirely possible that the sequence similarity of PAD4 to lipases and esterases does not signify any lipolytic activity as such, regions of homology in PAD4 primary structure suggest such activity. As such, PAD4 may be involved in degradation of a precursor of jasmonic acid (JA). There is a considerable amount of evidence for the involvement of JA, a small lipid-derived molecule, in regulation of a defense response pathway parallel to but distinct from the SA-regulated pathway. It is possible that a function of PAD4 is to degrade a precursor of JA, thereby activating the SA-dependent pathway;

EDS1 is another Arabidopsis gene that has an important role in activation of defense responses (Falk et al., 1999, Proc. Natl. Acad. Sci. USA 96:3292–3297). EDS1 encodes a key component of disease resistance pathways activated in response to bacterial and oomycete pathogens (Parker et al., 1996, Plant Cell 8: 2033–2046; Aarts et al., 1998, Proc. Natl. Acad. Sci USA 95: 10306–10311). While EDS1 and PAD4 are distinct genes, PR-1 expression phenotypes of eds1 (Falk et al., 1999, Proc. Natl. Acad. Sci. USA 96:3292–3297) and pad4 (Zhou et al., 1998, Plant Cell 10:1021–1030) suggest that both genes act upstream from SA. The predicted amino acid sequence of EDS1 also shows similarity to the same class of eukaryotic lipases and esterases as PAD4 (FIG. 19A–FIG. 19C).

Though analysis revealed no sequence similarity for the COOH-terminal 360 amino acids of the PAD4 protein of SEQ ID NO. 55 with other known proteins, this region of the PAD4 protein must be essential to PAD4 function, since this region is truncated in pad4-1, pad4-3, and pad4-4 mutants (while it is absent in pad4-2 mutants).

The PAD4 gene complements all of the pad4-1 phenotypes tested. Transgenic plants that were homozygous for pad4-1, and carried either of the complementing cosmids #8 or #21 were tested for various pad4-1 phenotypes to confirm that PAD4 had indeed been cloned, and to test whether all of the phenotypes of pad4-1 plants are caused by the pad4-1 mutation. FIG. 10A–FIG. 10C shows that both cosmids complemented the phytoalexin-deficient, the enhanced bacterial growth, and the PR-1 expression defect phenotypes of pad4-1 mutants. For all three phenotypes, wild-type plants and complemented pad4-1 plants were indistinguishable, confirming that both cosmids carry PAD4, and demonstrating that the camalexin deficiency, enhanced bacterial growth, and PR-1 expression defects observed in pad4-1 plants all result from the pad4-1 mutation.

Additional tests demonstrated that other cosmids carrying the PAD4 gene (i.e., cosmids #7, #30, #35, and #24) complemented the phytoalexin-deficient, the enhanced bacterial growth, and the PR-1 expression defect of pad4-1 plants (FIG. 18B). Other cosmids that lacked all (e.g. cosmid #6) or a substantial part (e.g., cosmid #15), of the PAD4 gene did not complement the mutant phenotype of pad4-1 plants (FIG. 18B).

EXAMPLE 4

PAD4 Compositions for Enhancing Disease Resistance to Oomycetes

As-noted in Example 1, pad4 mutants of *Arabidopsis thaliana* plants have been isolated that show enhanced disease susceptibility when infected with virulent Psm ES4326. Plants homozygous for the recessive mutation pad4-1 also display susceptibility to several isolates of *Peronospora parasitica* (Glazebrook et al., 1997, Genetics 146: 381–392). Therefore, PAD4 compositions provided by the present invention may be used to enhance the resistance of plants to oomycetes such as Peronospora. Methods of recovering plants transgenic for PAD4 are used in the complementation studies involving cosmids described in Example 3, supra. Such methods are discussed in more detail in Example 8, infra.

Methods of assaying levels of resistance to *Peronospora parasitica* isolates exhibited by plants transgenic for PAD4 include qualitatively rating asexual reproduction of Peronospora on inoculated seedlings. Quantitatively analyzing the number of sporangiophores per cotyledon of inoculated seedlings may also be used as a method of assaying levels of resistance. To conduct seedling assays, Peronospora isolates were originally derived and bulked from oospore infection (sexual inoculum) of a single Arabidopsis seedling. Inoculum was adjusted to $5 \times 10^4$ conidiospores per milliliter and was applied in a fine mist onto seedlings using an atomizer. The degree of parasite reproduction may be determined quantitatively by counting the number of sporangiophores produced per seedling with the aid of a hand-held magnifying lens (×3) or dissecting microscope (×6–10) (Glazebrook et al., 1997, Genetics 146: 381–392). Other methods will be recognized by those of skill in the art in light of the present disclosure as also having potential applicability. Measuring ion leakage from infected leaf discs (U.S. Pat. No. 5,629,470, column 10, lines 31–40; this entire patent is incorporated herein by reference) may provide an example of such a method.

Growth of *Peronospora parasitica* isolates on seedlings of wild-type *Arabidopsis thaliana* plants (i.e., plants that express PAD4) was observed as rare or absent, while being qualitatively heavy on pad4-1 mutant plants (Glazebrook et al., 1997, Genetics 146: 381–392). Since transformation of pad4 mutant *Arabidopsis thaliana* plants with cosmids containing PAD4 restores camalexin accumulation and PR-1 -gene expression, growth of *Peronospora parasitica* isolates on seedlings of *Arabidopsis thaliana* that express PAD4 as a transgene is expected to be rare or absent.

EXAMPLE 5

A Test Method for Identifying Plants Where Incorporation Break of Recombinant PAD4 Would Enhance Disease Resistance Developing a test method for identifying plants in which recombinant PAD4 has the effect of enhancing disease resistance is readily accomplished using standard techniques.

By "enhancing disease resistance" is meant a greater level of resistance to a disease-causing pathogen or to an environmental stress in a transgenic plant (or cell or seed thereof) of the invention than the level of resistance relative to a control plant (for example, a non-transgenic plant). In preferred embodiments, the level of resistance in a transgenic plant of the invention is at least 20% (and preferably 30% or 40%) greater than the resistance of a control plant. In other preferred embodiments, the level of resistance is 50%/ o greater, 60% greater, and more preferably even 75% or 90% greater than a control plant; with up to 100% above the level of resistance as compared to a control plant being most preferred.

The generation and identification of plants in which recombinant PAD4 has been incorporated into a genome of a plant may be accomplished using methods such as those set forth in Example 8, infra.

The level of disease resistance is measured using conventional methods. For example, methods of assaying levels of resistance to oomycetes such as Peronospora exhibited by plants transgenic for PAD4 include qualitative and quantitative assays noted in Example #4, supra. In general, the level of resistance may be determined by comparing physical features and characteristics (for example, plant height and weight, or by comparing disease symptoms, for example, delayed lesion development, reduced lesion size, leaf wilting and curling, water-soaked spots, and discoloration of cells) of transgenic plants with non-transgenic control plants after plants of both categories are challenged with a disease inducing agent. See also, U.S. Pat. No. 5,629,470, which herein is incorporated by reference. Disease symptoms that may be assayed include not only those of plant physical features readily apparent to the naked eye, but also symptoms revealed through diagnostic tests utilizing biochemical and/or microscopic procedures.

EXAMPLE 6

Isolation of PAD4 Homologs

Using Arabidopsis nucleic acid sequences, or fragments thereof, as provided herein, the isolation of PAD4 homologs that are found in other plants is readily accomplished using standard techniques.

For example, a *Nicotiana glutinosa* cDNA library can be screened for the presence of a PAD4 homolog. The library is constructed in the lambda ZAP II vector from poly (A+)RNA isolated from *Nicotiana glutinosa* plants infected with tobacco mosaic virus (TMV) (Whitham et al., *Cell* 78:1101–1115, 1994). Commercial sources of libraries are also available (Clontech, Palo Alto Calif., Strategene, La Jolla Calif.). Bacteriophage are plated on NZY media using XL-I Blue host cells. Approximately $10^6$ placques are screened by transferring the phage DNA onto positively charged nylon membrane (GeneScreen; DuPont-New England Nuclear) and probing with a random primed $^{32}P$ labeled probe prepared using an Arabidopsis PAD4 cDNA as the template. Hybridization is performed at 37° C. in 40% formamide, 5×SSC, 5×Denhardt, 1% SDS, and 10% dextran sulfate. The filters are washed in 2×SSC for fifteen minutes at room temperature and 2×SSC, 1% SDS for thirty minutes at 37° C. Hybridizing clones are identified and purified. pBluescript plasmids are excised using XL-1 Blue host cells and R408 helper phage (Strategene, La Jolla Calif.). Restriction enzyme analysis and sequencing is carried out to determine the identity of insert DNA. Sequencing may be carried out using $^{35}S$-dATP and the Sequenase sequencing kit (*U.S. Biochemicals, Cleveland, Ohio*) or by using a Perkin Elmer/Applied Biosystems Model 373 Automated Sequencer (Foster City, Calif.).

Any plant cell can serve as the nucleic acid source for the molecular cloning of a PAD4 gene. Isolation of a PAD4 gene involves the isolation of those nucleic acid sequences that encode a protein exhibiting PAD4 function, for example, having a positive regulatory effect on phytoalexin levels and on PR-1 expression levels while having substantially no regulatory effect on PR-5, BGL2, or ASA1 expression levels in a disease defense response by a host plant, or, as another example, a protein having a positive regulatory effect on PAD4 expression levels (in addition to having a positive regulatory effect on phytoalexin levels and PR-1 expression levels while having substantially no regulatory effect on PR-5, BGL2, or ASA1 expression levels in a disease defense response in a host plant). Based on the PAD4-related nucleic acid sequences and polypeptides described herein, the isolation of additional plant PAD4 coding sequences is made possible using standard strategies and techniques that are well known in the art in light of the present disclosure.

For example, the PAD4 sequences described herein may be used, together with conventional screening methods of nucleic acid hybridization screening. Such hybridization techniques and screening procedures are well known to those skilled in the art and are described, for example, in Sambrook et al., *Molecular Cloning: A Laboratory Manual*, Cold Spring Harbor Laboratory Press, New York, 1989. In one particular example, the PAD4 cDNA (SEQ ID NO.:1), or fragments thereof, may be used as a probe to screen a recombinant plant DNA library for genes having sequence homology or identity to the PAD4 gene. Similarly, in another particular example, PAD4 cDNA (SEQ ID NO.:54), or fragments thereof, may be used as a probe to screen a recombinant plant DNA library for genes having sequence homology or identity to PAD4. Hybridizing sequences are detected by plaque or colony hybridization according to the methods described below.

Alternatively, using all or a portion of the amino acid sequence of a PAD4 polypeptide, one may readily design PAD4 specific oligonucleotide probes, including PAD4 degenerate oligonucleotide probes (i.e., a mixture of all possible coding sequences of a given amino acid sequence). These oligonucleotides may be based upon the sequence of either DNA strand and any appropriate portion of the PAD4 sequence. General methods for designing and preparing such probes are provided, for example, in Ausubel et al., 1996, *Current Protocols in Molecular Biology*, Wiley Interscience, New York. These oligonucleotides are useful for PAD4 gene isolation, either through their use as probes capable of hybridizing to PAD4 complementary sequences or as primers for various amplification techniques, for example, PCR cloning strategies. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, or they may be obtained from commercial sources.

In one particular example of this approach, related PAD4 sequences having greater than 80% identity are detected or isolated using high stringency conditions as provided herein.

If desired, RNA gel blot analysis of total or poly(A+) RNAs isolated from any plant (e.g., those crop plants described herein) may be used to determine the presence or absence of a PAD4 transcript using conventional methods. As an example, a Northern blot of plant RNA is prepared according to standard methods and probed with a DNA sequence set forth as SEQ ID NO.:1 in a hybridization solution containing 50% formamide, 5×SSC, 2.5× Denhardt's solution, and 300 μg/mL salmon sperm DNA at 37° C. Following overnight hybridization, the blot is washed two times for ten minutes each in a solution containing 1×SSC, 0.2% SDS at 37° C. An autoradiogram of the blot would demonstrate the presence or absence of a PAD4-hybridizing RNA in the plant RNA sample, indicating whether the plant encoded a PAD4 gene. Isolation of the hybridizing transcript is performed using standard cDNA cloning techniques.

As provided herein, PAD4 oligonucleotides may also be used as primers in amplification cloning strategies, for example, using PCR. Primers are optionally designed to allow cloning of the amplified product into a suitable vector, for example, by including appropriate restriction sites at the 5' and 3' ends of the amplified fragment. If desired, PAD4 sequences may be isolated using the PCR "RACE" technique, or Rapid Amplification of cDNA Ends. By this method, oligonucleotide primers based on a PAD4 sequence are oriented in the 3' and 5' directions and are used to generate overlapping PCR fragments. These overlapping 3' and 5'-Random-Amplified-cDNA-End (RACE) products are combined to produce an intact complete cDNA, as also described further in Example 11, infra.

Alternatively, a plant cDNA containing a putative PAD4 gene may be tested by functional complementation of a pad4 mutant (for example, the pad4 mutant described herein) according to standard methods described herein.

Confirmation of relatedness of a sequence to the PAD4 polypeptide family may be accomplished by a variety of conventional methods including, but not limited to, functional complementation assays and sequence comparison of the gene and its expressed product. In addition, the activity of the gene product may be evaluated according to any of the techniques described herein, for example, the functional or immunological properties of its encoded product.

Once a PAD4 sequence is identified, it is cloned according to standard methods and used for the construction of plant expression vectors as described below.

EXAMPLE 7

PAD4 Recombinant Protein Expression

PAD4 polypeptides may be expressed and produced by transformation of a suitable host cell with all or part of a PAD4 cDNA (for example, SEQ ID NO.:1 or SEQ ID NO.:54) in a suitable expression vehicle or with a plasmid construct engineered for increasing the expression of a PAD4 polypeptide in vivo.

Those skilled in the field of molecular biology will understand that any of a wide variety of expression systems may be used to provide the recombinant protein. The precise host cell used is not critical to the invention. The PAD4 protein may be produced in a prokaryotic host, for example, *E. coli*, or in a eukaryotic host, for example, *Saccharomyces cerevisiae*, mammalian cells (for example, COS 1 or N1H 3T3 cells), or any of a number of plant cells or whole plant including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, conifers, petunia, tomato, potato, pepper, tobacco, Arabidopsis, broccoli, cabbage, brussel sprouts, radish, kale, Chinese kale, kohlrabi, turnip, rutabaga, mustard, lettuce, sunflower, oilseed rape, flax, cotton, sugarbeet, celery, soybean, Medicago such as alfalfa, lotus, Vigna, cucumber, carrot, eggplant, cauliflower, horseradish, morning glory, poplar, walnut, apple, grape, asparagus, cassava, rice, maize, millet, onion, barley, orchard grass, oat, rye, and wheat.

Such cells are available from a wide range of sources including the American Type Culture Collection (Rockland, Md.); or from any of a number of seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I.K., *Cell Culture and Somatic Cell Genetics of Plants*, Vol. I, II, III Laboratory Procedures and Their Applications Academic Press, New York, 1984; Dixon, R. A. and R. A. Gonzales, Ed, *Plant Cell Culture—A Practical Approach*, $2^{nd}$ Ed, IRL Press, Oxford, England, 1994; Green et al., *Plant Tissue and Cell Culture*, Academic Press, New York, 1987; and Gasser and Fraley, *Science* 244:1293, 1989.

For prokaryotic expression, DNA encoding a PAD4 polypeptide is carried on a vector operably linked to control signals capable of effecting expression in the prokaryotic host. For example, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Commonly used regulatory elements are defined herein to include promoters for transcription initiation, optionally with an operator, along with ribosome binding site sequences. Promoters commonly used to direct protein expression include the beta-lactamase (penicillinase), the lactose (lac), the tryptophan (Trp), and the tac promoter systems, as well as the lambda-derived $P_1$ promoter and N-gene ribosome binding site.

One particular bacterial expression system for PAD4 polypeptide production is the *E. coli* pET expression system (Novagen, Inc., Madison, Wis.). According to this expression system, DNA encoding a PAD4 polypeptide is inserted into a pET vector in an orientation designed to allow expression. Since the PAD4 gene is under the control of T7 regulatory signals, expression of PAD4 is induced by inducing the expression of T7 RNA polymerase in the host cell. This is typically achieved using host strains which express T7 RNA polymerase in response to IPTG induction. Once produced, recombinant PAD4 polypeptide is then isolated according to standard methods known in the art.

Another bacterial expression system for PAD4 polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

For eukaryotic expression, the method of transformation or transfection and the choice of vehicle for expression of PAD4 polypeptide will depend on the host system selected. Transformation and transfection methods are described, e.g., in Ausubel et al., 1996, *Current Protocols in Molecular Biology*, Wiley Interscience, New York; Weissbach and Weissbach, *Methods for Plant Molecular Biology*, Academic Press, 1989; Gelvin et al., *Plant Molecular Biology Manual*, Kluwer Academic Publishers, 1990; Kindle K., *Proc. Nat i. Acad. Sci., USA* 87:1228, 1990; Potrykus, I., *Annu. Rev.*

*Plant Physiol. Plant Mol. Biology* 42:205, 1991; and Biorad (Hercules, Calif.) Technical Bulletin #1687 (Biolistic Particle Delivery Systems). Expression vehicles may be chosen from those provided, e.g., in *Cloning Vectors: A Laboratory Manual* (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above. Other expression constructs are described by Faley et al. (U.S. Pat. No. 5,352,605, incorporated by reference herein).

EXAMPLE 8

Construction of PAD4 Transgenic Plants

Most preferably, a PAD4 polypeptide is produced by a stably-transfected plant cell line, a transiently-transfected plant cell line, or by a transgenic plant. A number of vectors suitable for stable or extrachromosomal transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra).

Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once a desired PAD4 nucleic acid sequence is obtained as described above, it may be manipulated in a variety of ways known in the art. For example, where the sequence involves non-coding flanking regions, the flanking regions may be subjected to mutagenesis.

A PAD4 DNA sequence of the invention may, if desired, be combined with other DNA sequences in a variety of ways. A PAD4 DNA sequence of the invention may be employed with all or part of the gene sequences normally associated with a PAD4 protein. In its component part, a DNA sequence encoding a PAD4 protein is combined in a DNA construct having a transcription initiation control region capable of promoting transcription and translation in a host cell.

In general, the constructs will involve regulatory regions functional in plants that provide for modified production of PAD4 protein as discussed herein. The open reading frame coding for a PAD4 protein or functional fragment thereof will be joined at its 5' end to a transcription initiation regulatory region such as the sequence naturally found in the 5' upstream region of a PAD4 structural gene. Numerous other transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well. Transcript termination regions may be provided by a DNA sequence encoding a PAD4 protein or any convenient transcription termination region derived from a different gene source. The transcript termination region will contain preferably at least 1–3 kb of sequence 3' to the structural gene from which the termination region is derived. Plant expression constructs having PAD4 as the DNA sequence of interest for expression (in either the sense or antisense orientation) may be employed with a wide variety of plant life, particularly plant life involved in the production of storage reserves (for example, those for a variety of industrial and agricultural applications as discussed infra). Importantly, this invention is applicable to dicotyledons and monocotyledons, and will be readily applicable to any new or improved transformation or regeneration method.

The expression constructs include at least one promoter operably linked to at least one PAD4 gene. An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. Examples of plant expression constructs using these promoters are found in Fraley et al., U.S. Pat. No. 5,352,605, incorporated by reference herein. In most tissues of transgenic plants, the CaMV 35S promoter is a strong promoter. The CaMV promoter is also highly active in monocots. Moreover, activity of this promoter can be further increased (i.e., between 2–10 fold) by duplication of the CaMV 35S promoter (see, e.g., U.S. Pat. No. 5,378,142, incorporated by reference herein).

Other useful plant promoters include, without limitation, the nopaline synthase (NOS) promoter (U.S. Pat. No. 5,034,322, incorporated by reference herein), the octopine synthase promoter, figwort mosaic virus (FMV) promoter (Rodgers, U.S. Pat. No. 5,378,619, incorporated by reference herein), and the rice actin promoter.

Exemplary monocot promoters include, without limitation, commelina yellow mottle virus promoter, sugar cane badna virus promoter, rice tungro bacilliform virus promoter, maize streak virus element, and wheat dwarf virus promoter.

For certain applications, it may be desirable to produce a PAD4 gene product in an appropriate tissue, at an appropriate level, or at an appropriate developmental time. For this purpose, there are an assortment of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression, light-regulated gene expression (e.g., the pea rbcS-3A; the maize rbcS promoter; the chlorophyll a/b-binding protein gene found in pea; the ARabssu promoter; or the rice rbs promoter), hormone-regulated gene expression (for example, the abscisic acid (ABA) responsive sequences from the Em gene of wheat; the ABA-inducible HVA1 and HVA22, and rd29A promoters described for barley and Arabidopsis; and wound-induced gene expression (for example, of wunI), organ-specific gene expression (for example, of the tuber-specific storage protein gene; the 23-kDa zein gene from maize; or the French bean β-phaseolin gene), or pathogen-inducible promoters (for example, PR-1, prp-1, or β-1,3 glucanase promoters, the fungal-inducible wirla promoter of wheat, and the nematode-inducible promoters, TobRB7-5A and Hmg-1, of tobacco and parsley, respectively).

Plant expression vectors may also optionally include RNA processing signals, e.g., introns, which have been shown to be important for efficient RNA synthesis and accumulation. The location of the RNA splice sequences can dramatically influence the level of transgene expression in plants. In view of this fact, an intron may be positioned upstream or downstream of a PAD4 polypeptide-encoding sequence in the transgene to modulate levels of gene expression.

In addition to the aforementioned 5' regulatory control sequences, the expression vectors may also include regulatory control regions which are generally present in the 3' regions of plant genes. For example, the 3' terminator region may be included in the expression vector to increase stability of the mRNA. One such terminator region may be derived from the P1–11 teminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltrhansferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 175–100 $\mu$g/mL (kanamycin), 20–50 $\mu$g/mL (hygromycin), or 5–10 $\mu$g/mL (bleomycin). A useful strategy for selection of transformants for herbicide resistance is described, e.g., by Vasil, supra.

In addition, if desired, the plant expression construct may contain a modified or fully-synthetic structural PAD4 coding sequence which has been changed to enhance the performance of the gene in plants. Methods for constructing such a modified or synthetic gene are described in U.S. Pat. No. 5,500,365, incorporated by reference herein.

It is apparent to one skilled in the art of plant molecular biology, that the level of gene expression is dependent, not only on the combination of promoters, RNA processing signals, and terminator elements, but also on how these elements are used to increase the levels of selectable marker gene expression.

Upon construction of the plant expression vector, several standard methods are available for introduction of the vector into a plant host, thereby generating a transgenic plant. These methods include (1) Agrobacterium-mediated transformation (A. tumefaciens or A. rhizogenes), (2) the particle delivery or biolistic system, (3) microinjection protocols, (4) polyethylene glycol (PEG) procedures, (5) liposome-mediated DNA uptake, (6) electroporation protocols, and (7) the vortexing method. The method of transformation is not critical to the invention. Any method which provides for efficient transformation may be employed. As newer methods are available to transform crops or other host cells, they may be directly applied. Suitable plants for use in the practice of the invention have been listed herein.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in E. coli, and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in E. coli. This permits facile production and testing of transgenes in E. coli prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into the nucleus or the chloroplast or the mitochondria.

In general, transfer and expression of transgenes in plant cells are now routine practices to those skilled in the art, and have become major tools to carry out gene expression studies in plants and to produce improved plant varieties of agricultural or commercial interest.

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant.

In one particular example, a cloned PAD4 polypeptide construct under the control of the 35S CaMV promoter and the nopaline synthase terminator and carrying a selectable marker (for example, kanamycin resistance) is transformed into Agrobacterium. Transformation of leaf discs (for example, of tobacco or potato leaf disks), with vector-containing Agrobacterium is carried out. Putative transformants are selected after a few weeks (for example, 3 to 5 weeks) on plant tissue culture media containing kanamycin (e.g. 100 $\mu$g/mL). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques.

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify the expression-positive plants. Standard techniques for RNA analysis are employed and include PCR amplification assays using oligonucleotide primers designed to amplify only transgene RNA templates and solution hybridization assays using transgene-specific probes. The RNA-positive plants are then analyzed for protein expression by Western immunoblot analysis using PAD4 specific antibodies. In addition, in situ hybridization and immunocytochemistry according to standard protocols can be done using transgene-specific nucleotide probes and antibodies, respectively, to localize sites of expression within transgenic tissue.

Ectopic expression of PAD4 genes is useful for the production of transgenic plants having an increased level of resistance to disease.

In addition, if desired, once the recombinant PAD4 protein is expressed in any cell or in a transgenic plant (for example, as described above), it may be isolated, e.g., using affinity chromatography. In one example, an anti-PAD4 polypeptide antibody may be attached to a column and used to isolate the polypeptide. Lysis and fractionation of PAD4-producing cells prior to affinity chromatography may be performed by standard methods. Once isolated, the recombinant protein can, if desired, be further purified, for example, by high performance liquid chromatography.

Polypeptides of the invention, particularly short PAD4 protein fragments, can also be produced by chemical synthesis. These general techniques of polypeptide expression and purification can also be used to produce and isolate useful PAD4 fragments or analogs.

EXAMPLE 9

Ectopic Expression of PAD4 Genes for Engineering Plant Defense Responses to Pathogens As discussed supra, plasmid constructs designed for the expression of PAD4 gene products are useful, for example, for activating plant defense pathways that confer anti-pathogenic properties to a transgenic plant. PAD4 genes that are isolated from a host plant (e.g., Arabidopsis or Nicotiana) may be engineered for expression in the same plant, a closely related species, or a distantly related plant species. For example, a cruciferous Arabidopsis PAD4 gene may be engineered for constitutive low level expression and then transformed into an Arabidopsis host plant. Alternatively, an Arabidopsis PAD4 gene may be engineered for expression in other cruciferous plants, such as Brassicas (for example, broccoli, cabbage, and cauliflower). Similarly, a PAD4 homolog of *Nicotiana glutinosa* is useful for expression in related solanaceous plants, such as tomato, potato, and pepper. To achieve pathogen resistance, it is important to express an PAD4 protein at an effective level. Evaluation of the level of pathogen protection conferred by a plant by ectopic expression of a PAD4 gene is determined according to conventional methods and assays.

For example, constitutive ectopic expression of a PAD4 gene of Arabidopsis (e.g., SEQ ID NO:1 or SEQ ID NO.:54) or a PAD4 homolog of *Nicotiana glutinosa* in Russet Burbank potato may be used to control *Phytophthora infestans* infection. A plant expression vector is constructed that contains a PAD4 cDNA sequence expressed under the control of the enhanced CaMV 35S promoter as described by McPherson and Kay (U.S. Pat. No. 5,359,142, incorporated by reference herein). This expression vector is then used to transform Russet Burbank according to the methods described in Fischoff et al. (U.S. Pat. No. 5,500,365, incorporated by reference herein). To assess resistance to fungal infection, transformed Russet Burbank and appropriate controls are grown to approximately eight-weeks-old, and leaves (for example, the second or third from the top of the plant) are inoculated with a mycelial suspension of *P. infestans*. Plugs of *P. infestans* mycelia are inoculated on each side of the leaf midvein. Plants are subsequently incubated in a growth chamber at 27° C. with constant fluorescent light.

Leaves of transformed Russet Burbank and control plants are then evaluated for resistance to *P. infestans* infection according to conventional experimental methods. For this evaluation, the number of lesions per leaf and percentage of leaf area infected are recorded every twenty-four hours for seven days after inoculation. From these data, levels of resistance to *P. infestans* are determined. Transformed potato plants that express a PAD4 gene having an increased level of resistance of *P. infestans* relative to control plants are taken as being useful in the invention.

In another example, expression of a PAD4 homolog of *Nicotiana glutinosa* in tomato may be used to control bacterial infection, for example, to *Pseudomonas syringae*. Specifically, a plant expression vector is constructed that contains the cDNA sequence of a PAD4 homolog from *Nicotiana glutinosa* which is expressed under the control of the enhanced CaMV 35S promoter as described by McPherson and Kay, supra. This expression vector is then used to transform tomato plants according to the methods described in Fischoff et al., supra. To assess resistance to bacterial infection, transformed tomato plants and appropriate controls are grown, and their leaves are inoculated with a suspension of *P. syringae* according to the standard methods, for example, those described herein. Plants are subsequently incubated in a growth chamber, and the inoculated leaves are subsequently analyzed for signs of disease resistance according to standard methods. For example, the number of chlorotic lesions per leaf and percentage of leaf area infected are recorded and evaluated after inoculation. From a statistical analysis of these data, levels of resistance to *P. syringae* are determined. Transformed tomato plants that express a PAD4 homolog of *Nicotiana glutinosa* and that have an increased level of resistance to *P. syringae* relative to control plants are taken as being useful in the invention.

In still another working example, expression of a PAD4 homolog of rice is used to control fungal diseases, for example, the infection of tissue by *Magnaporthe grisea,* the cause of rice blast. In one particular approach, a plant expression vector is constructed that contains the cDNA sequence of a rice PAD4 homolog that is constitutively expressed under the control of the rice actin promoter. This expression vector is then used to transform rice plants according to conventional methods. To assess resistance to fungal infection, transformed rice plants and appropriate controls are grown, and their leaves are inoculated with a mycelial suspension of *M. grisea* according to standard methods. Plants are subsequently incubated in a growth chamber and the inoculated leaves are subsequently analyzed for disease resistance according to standard methods. For example, the number of lesions per leaf and percentage of leaf area infected are recorded and evaluated after inoculation. From a statistical analysis of these data, levels of resistance to *M. grisea* are determined. Transformed rice plants that express a rice PAD4 homolog having an increased level of resistance to *M. grisea* relative to control plants are taken as being useful in the invention.

EXAMPLE 10

Camalexin Expression Levels in pad4-1 Plants Transformed with PAD4 EDNA Corresponding to SEQ ID NO.: 1 in Plasmid pBI1.4t PAD4 cDNA corresponding to SEQ ID -NO.:1 was introduced into the transformation vector plasmid pBI1.4t behind the vector's 35S promoter (Mindrinos et al., 1994, Cell 78: 1856–1869). This construct, as well as the vector alone as a control, was used to transform pad4-1 plants. Both the control plant and PAD4-transformed plants (i.e., original transformants) were infected with Psm ES4326, and camalexin levels were assayed 2 days later using methods detailed in Example 1, supra. Camalexin levels were found to be as in Table 4.

TABLE 4

Camalexin Levels in pad4-1 Transformants

| Plant | Camalexin Level (ng per $cm^2$ leaf area) |
|---|---|
| Control (transformed with vector alone) | 79 |
| Experimental #1 | 175 |
| Experimental #2 | 261 |
| Experimental #3 | 236 |
| Experimental #4 | 212 |
| Experimental #5 | 94 |

While camalexin levels in wild-type plants were not assayed for this example, camalexin levels in wild-type plants are typically ten times camalexin levels in pad4-1 plants (such as the Control) after infection with Psm ES4326. Consequently, while not a ten-fold increase, the significant increase in camalexin levels in the Experimental Plants #1–#4 carrying PAD4 cDNA corresponding to SEQ ID NO.:1 suggested that the cDNA was complementing the camalexin-deficient phenotype of pad4-1 plants, although to levels lower than the camalexin levels of wild-type plants. These data further suggest that the PAD4 cDNA corresponding to SEQ ID NO.:1 does encode a functional PAD4 protein.

Experimental Plants #1–#4 of the original transformants were allowed to set seed, and seeds were allowed to germinate on agar medium containing kanamycin in order to select for progeny plants carrying at least one copy of the transgene. Five kanamycin-resistant plants from each line, as well as untransformed pad4-1 plants, were infected with Psm ES4326, and camalexin was assayed two days later. None of progeny plants selected for kanamycin resistance displayed higher camalexin levels than the pad4-1 controls.

A possible explanation for the failure of the progeny plants to display higher camalexin levels could be that gene silencing occurs in progeny plants. Silencing of a 35S-driven cDNA of the disease resistance gene RPS2 has been observed even in original transformants (Midrinos et al., 1994, Cell 78: 1856–1860). A construct in which PAD4 cDNA corresponding to SEQ ID NO.:1 is driven by a different promoter; such as an Arabidopsis promoter, for example, may not elicit a silencing effect.

EXAMPLE 11

Preparation of PAD4 cDNA in pAtcPAD4.2

This example presents details of preparation of a complete PAD4 cDNA. The nucleotide sequence of a complete PAD4 cDNA is provided in SEQ ID NO.:54.

A cDNA library was constructed using poly-A RNA purified from wild-type (Col) leaves infected with Psm ES4326. The 5' and 3'-RACE ends of the PAD4 cDNA were isolated using the Marathon cDNA isolation kit (Clontech, Palo Alto, Calif.) according to instructions provided by the supplier. The gene-specific primers used were 5'-CGTGAAATTGAGGTGGAGAGAGATTGGTTTCCG-3' (SEQ ID NO.:82) and 5'-GAATTGTTAGGTAAAAAGCTGGTGGTGATAAC CGG-3' (SEQ ID NO.:83) for the 5' and 3' RACE products, respectively. A complete cDNA was then isolated from the cDNA library using PCR with primers 5'-ATGGACGATTGTCGAGACGAG-3' (SEQ ID NO.:84) and 5'-AGAATATATAGTAACATTCATCAGAAAGTC-3' (SEQ ID NO.: 85) corresponding to the ends of the cDNA sequence, and cloned into plasmids pCR2.1 (Invitrogen, Carlsbad, Calif.) and pBLUESCRIPT SK+ (Strategene, La Jolla, Calif.). The resultant recombinant Bluescript plasmid was named pAtcPAD4.2 and deposited with the ATCC in *E. coli* strain DH5α, having accession number ATCC Deposit No. PTA-864.

EXAMPLE 12

PAD4-SA Amplification Loop

This example details evidence for a PAD4-SA amplification loop, as revealed by PAD4 RNA blot analysis of PAD4 expression (presented in FIGS. 13A–FIG. 13B, FIG. 14A–FIG. 14B, FIG. 15, and FIG. 16). Conditions under which *Arabidopsis thaliana* plants were grown, inoculations of plants with Psm ES4326 (see legends of FIG. 13A–FIG. 13B, and FIG. 15, supra), and treatments of plants with SA (see legends of FIG. 14A–FIG. 14B, and FIG. 16, supra) were as noted in Example 1, supra.

PAD4 RNA Blot Analysis. Tissue samples consisting of three to five leaves were collected, frozen in liquid nitrogen and stored at −80° C. Total RNA was extracted and 5 μg of RNA per sample was loaded and separated on formaldehyde-agarose gels (Reuber and Ausubel, 1996, Plant Cell 8:241–249). Samples were blotted onto a Hybond-$N^+$ membrane (Amersham Corp., Arlington Heights, Ill.). Hybridizations were performed using digoxygenin-labeled probes followed by washes in 0.5×SSC at 65° C. and chemiluminescent detection with CSPD, according to the supplier's instructions (Boehringer Mannheim, Indianapolis, Ind.). For the RNA blots, single-stranded antisense PAD4 probe was made from the plasmid pDJ5.1 (i.e., ATCC pAtcPAD4 in *E. coli* strain DH5α) using antisense primer 5'-CGTGAAATTGAGGTGGAGAGAGATTGGTTTCCG-3' (SEQ ID NO.:82). The single-stranded 18S rRNA probe was made as described in Zhou et al. (1998, Plant Cell 10: 1021–1030). Blots were stripped and reprobed with the 18S rRNA probe to assess equal loading of RNA samples.

PAD4 Expression is Induced by Pathogen Infection and SA. PAD4 RNA blot analysis on wild-type and pad4 leaves infected with Psm ES4326 revealed that PAD4 mRNA levels increased beginning at 12 hours and reached a maximum at 36 hours after infection (FIG. 13A and FIG. 13B). PAD4 transcript levels were very low in all of the four pad4 mutants even. 36 hours after infection with Psm ES4326 (FIG. 13A and FIG. 13B). A possible explanation for this difference in mRNA levels is that PAD4 function is required for activation of PAD4 expression.

In order to test, inter alia, if activation of PAD4 expression requires SA, wild-type (Col and Ler) and mutant pad4 plants were treated with SA at a concentration of 5 mM. Such SA treatment has previously been shown to rescue pad4-1 mutant phenotypes (Zhou et al., 1998, Plant Cell 10: 1021–1030). PAD4 mRNA levels increased rapidly after SA treatment in wild-type (Col) (FIG. 14A, FIG. 14B, and FIG. 16) and wild-type (Ler) (FIG. 14B) plants, as well as pad4-1, pad4-3, and pad4-4 plants (FIG. 14B), but not in pad4-2 plants (FIG. 14B). These results (other than those from pad4-2 plants) suggested that SA is sufficient for induction of PAD4 mRNA synthesis.

The results from pad4-2 plants may be accounted for through the-molecular nature of the pad4-2 mutation. The mutation in pad4-2 causes a translation stop early in the protein (i.e., a stop replaces arginine at position 182, see Table 3, supra). mRNAs containing premature chain termination mutations ("nonsense mRNAs") are often unstable because they are subject to nonsense mediated mRNA decay (NMD) (Culbertson, 1999, Trends in Genetics 15: 74–80). Chain termination mutations near the 5'-end of an open reading frame tend to cause a stronger NMD effect than those near the 3'-end (Peltz et al., 1993, Genes and Development 7:1737–1754). NMD may explain how strong SA-induction of the PAD4 transcript could be detected in pad4-1, pad4-3, and pad4-4 plants, but not pad4-2 plants.

Psm ES4326-inducibility of PAD4 is SA-dependent. In order to confirm the requirement of SA for induction of PAD4 by pathogen infection, PAD4 transcript levels in SA-deficient plants transgenic for the bacterial gene salicylate hydroxylase (nahG) plants were examined. Again, all nahG plants in all Examples provided herein were of the Landsberg erecta ecotype. Salicylate hydroxylase, which is encoded by the bacterial gene nahG, breaks down SA to catechol, and transgenic plants expressing nahG are unable to acquire SAR (Gaffney et al., 1993, Science 261:754–756). In plants infected with Psm ES4326, PAD4 transcript levels were much lower in nahG plants than in wild-type (Col and Ler) plants 36 hours after treatment (FIG. 15). On the other hand, in wild-type (Col and Ler) and nahG plants mock inoculated with 10 mM $MgSO_4$ levels of PAD4 mRNA 36 hours after infection were comparable to the low levels of PAD4 mRNA in uninfected wild-type plants (FIG. 15). These results demonstrate that Psm ES4326-inducibility of PAD4 expression is strongly SA-dependent.

Psm ES4326-inducibility of PAD4 is NRP1-independent. In order to determine if pathogen-inducibility of PAD4 mRNA requires NRP1, levels of PAD4 mRNA in wild-type (Col and Ler) and npr1-1 plants were examined after infection with Psm ES4326. Again, when infected with a pathogen (like Psm ES4326) that induces SAR in wild-type plants, npr1-1 mutant plants accumulate high levels of SA, but do not develop SAR, indicating that NPR1 acts downstream from SA. RNA blot analysis revealed that PAD4 transcript levels 36 hours after infection with Psm ES 4326 were comparable to wild-type (Col and Ler) in npr1-1 plants (FIG. 15), demonstrating that pathogen-inducibility of PAD4 mRNA is NPR1-independent.

SA-inducibility of PAD4 is NPR1-dependent. In order to determine if induction of PAD4 by exogenous SA requires NPR1, wild-type (Col) and npr1-1 plants treated with 5 mM SA were examined for PAD4 expression six and twelve hours after treatment. RNA blot analysis revealed that PAD4 transcript levels were undetectable in npr1-1 plants six and twelve hours after SA treatment, while being markedly detectable in wild-type plants after SA treatment (FIG. 16). These results demonstrate that SA-induced expression of PAD4 is NPR1-dependent.

Models to Explain Patterns of PAD4 mRNA Expression. These patterns of PAD4 mRNA expression provide further support for the existence of SA potentiation mechanisms in activation of plant defense responses, and strongly suggest the existence of a PAD4-SA amplification loop in defense signaling. That is, these patterns of PAD4 expression strongly suggest that PAD4 and SA form part of signal amplification loop that is required for expression of PR-1 and other defense responses.

One model that may explain the expression patterns of PAD4 is shown in FIG. 17A. This model postulates that SA is necessary but not sufficient for activation of PAD4 transcription. Another component is required for activation of PAD4 transcription—NPR1 or a yet-unidentified signal resulting from pathogen infection. Support for this model comes from studies on defense gene expression in npr1 plants after pathogen infection (FIG. 15) or SA treatment (FIG. 16). The expression of PAD4 follows is NPR1-dependent upon SA treatment (FIG. 16) but not so upon infection with Psm ES4326 (FIG. 15). Furthermore, this model is consistent with PAD4 function promoting PAD4 expression (i.e., having a positive regulatory effect on PAD4 expression levels).

A second model that may explain the expression patterns of PAD4 is shown in FIG. 17B. This model postulates two different responses of PAD4 to different SA levels. Low SA levels activate PAD4 function, while very high SA levels turn it off. NPR1 inhibits the SA-amplification loop and PAD4 inhibits this activity of NPR1. When pathogen infection occurs, SA levels rise and PAD4 is activated. Consequently, NPR1 inhibition of the SA-amplification loop is itself inhibited by PAD4, the SA signal is amplified, and an increase in PAD4 transcript levels is observed (in a NPR1-independent manner). However, when plants are sprayed with SA, the SA levels are too high, and PAD4's inhibitory activity (against NPR1's inhibition of the SA amplification loop) is quenched. With NPR1-inhibiting the SA amplification loop, transcription of PAD4 is turned off. In short, inhibition of NRP1 by PAD4 at low SA levels is required for PAD4 expression, or, as for the previously-presented model, this second model is consistent with PAD4 function promoting PAD4 expression (i.e., having a positive regulatory effect on PAD4 expression levels).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A purified nucleic acid molecule having a nucleotide sequence selected from the group consisting of:
   a) the nucleotide sequence of SEQ ID NO:1; and
   b) a nucleotide sequence that is the complement of a).

2. The purified nucleic acid molecule of claim 1 wherein the molecule is obtained from a plant of the genus Arabidopsis.

3. A recombinant vector comprising the purified nucleic acid molecule of claim 1.

4. A method of producing a transgenic plant, comprising incorporating the nucleic acid molecule of claim 1 into a plant cell and regenerating a transgenic plant from the plant cell.

5. A purified nucleic acid molecule having a nucleotide sequence selected from the group consisting of:
   a) the nucleotide sequence of SEQ ID NO:54; and
   b) a nucleotide sequence that is the complement of a).

6. The purified nucleic acid molecule of claim 5 wherein the molecule is obtained from a plant of the genus Arabidopsis.

7. A recombinant vector comprising the purified nucleic acid molecule of claim 5.

8. A recombinant host cell comprising the nucleic acid molecule of claim 5.

9. A method of producing a transgenic plant, comprising incorporating the nucleic acid molecule of claim 5 into a plant cell and regenerating a transgenic plant from the plant cell.

10. A purified nucleic acid molecule comprising the coding portion of SEQ ID NO:1 beginning with nucleotide 36, the coding portion of SEQ ID NO:1 beginning with nucleotide 39, the coding portion of SEQ ID NO:54 beginning with nucleotide 1, or the coding portion of SEQ ID NO:54 beginning with nucleotide 4.

* * * * *

SEQUENCE LISTING

<160> NUMBER OF SEQ ID NOS: 85

<210> SEQ ID NO 1
<211> LENGTH: 1722
<212> TYPE: DNA
<213> ORGANISM: Arabidopsis thaliana
<220> FEATURE:
<221> NAME/KEY: CDS
<222> LOCATION: (36)..(1616)

<400> SEQUENCE: 1

```
gtcgattcga gacgagtgag ttgcaagctt cggta atg ata tcg act cct tta           53
                                      Met Ile Ser Thr Pro Leu
                                       1               5 ttt acc gat tct tgg agt tca tgc aac acc gca aat tgc aac ggg agt         101
Phe Thr Asp Ser Trp Ser Ser Cys Asn Thr Ala Asn Cys Asn Gly Ser
             10                  15                  20 ata aag atc cat gac atc gcc ggg att aca tac gtt gct ata ccg gcg         149
Ile Lys Ile His Asp Ile Ala Gly Ile Thr Tyr Val Ala Ile Pro Ala
         25                  30                  35 gta tcg atg att cag ttg ggg aat ctt gtg ggc ttg cca gtc acc gga         197
Val Ser Met Ile Gln Leu Gly Asn Leu Val Gly Leu Pro Val Thr Gly
     40                  45                  50 gat gtt ctt ttc ccc ggc tta tcc tcc gat gaa cct cta cct atg gtc         245
Asp Val Leu Phe Pro Gly Leu Ser Ser Asp Glu Pro Leu Pro Met Val
 55                  60                  65                  70 gac gct gcc ata ctc aaa ctc ttt ctt cag tta aag atc aag gaa gga         293
Asp Ala Ala Ile Leu Lys Leu Phe Leu Gln Leu Lys Ile Lys Glu Gly
                 75                  80                  85 ttg gaa ttg gaa ttg tta ggt aaa aag ctg gtg gtg ata acc ggc cat         341
Leu Glu Leu Glu Leu Leu Gly Lys Lys Leu Val Val Ile Thr Gly His
             90                  95                 100 tca acc ggc ggc gca ttg gcc gct ttc acc gca ctt tgg ctt cta tct         389
Ser Thr Gly Gly Ala Leu Ala Ala Phe Thr Ala Leu Trp Leu Leu Ser
        105                 110                 115 caa tct tct ccg ccg tca ttc cgc gtc ttt tgt atc acc ttt ggc tct         437
Gln Ser Ser Pro Pro Ser Phe Arg Val Phe Cys Ile Thr Phe Gly Ser
    120                 125                 130 cct ctg ctc gga aac caa tct ctc tcc acc tca att tca cga tca cgt         485
Pro Leu Leu Gly Asn Gln Ser Leu Ser Thr Ser Ile Ser Arg Ser Arg
135                 140                 145                 150 tta gca cac aac ttc tgc cac gtg gtc tcc atc cac gac ctc gtt cct         533
Leu Ala His Asn Phe Cys His Val Val Ser Ile His Asp Leu Val Pro
                155                 160                 165 aga agc agc aat gaa caa ttc tgg ccc ttt gga act tac ttg ttc tgt         581
Arg Ser Ser Asn Glu Gln Phe Trp Pro Phe Gly Thr Tyr Leu Phe Cys
            170                 175                 180 tcc gac aaa gga ggt gtc tgt cta gac aac gct ggt tct gtt cgt ctg         629
Ser Asp Lys Gly Gly Val Cys Leu Asp Asn Ala Gly Ser Val Arg Leu
        185                 190                 195 atg ttt aat atc ctc aac acc aca gca act caa aac acc gag gaa cat         677
Met Phe Asn Ile Leu Asn Thr Thr Ala Thr Gln Asn Thr Glu Glu His
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 200 |     |     |     |     | 205 |     |     |     |     |     | 210 |     |     |
| cag | agg | tac | gga | cac | tat | gtg | ttc | aca | ctt | tca | cac | atg | ttt | ctt | aaa | 725 |
| Gln | Arg | Tyr | Gly | His | Tyr | Val | Phe | Thr | Leu | Ser | His | Met | Phe | Leu | Lys |
| 215 |     |     |     |     | 220 |     |     |     |     | 225 |     |     |     |     | 230 |
| tct | aga | agc | ttt | ctt | ggt | ggg | agt | atc | ccc | gac | aat | agc | tac | caa | gct | 773 |
| Ser | Arg | Ser | Phe | Leu | Gly | Gly | Ser | Ile | Pro | Asp | Asn | Ser | Tyr | Gln | Ala |
|     |     |     |     | 235 |     |     |     |     | 240 |     |     |     |     | 245 |     |
| ggt | gtt | gcg | tta | gcc | gtt | gaa | gct | cta | ggt | ttc | tct | aac | gat | gac | aca | 821 |
| Gly | Val | Ala | Leu | Ala | Val | Glu | Ala | Leu | Gly | Phe | Ser | Asn | Asp | Asp | Thr |
|     |     < /br>  | 250 |     |     |     |     | 255 |     |     |     |     | 260 |     |     |     |
| agt | ggc | gtt | tta | gtc | aaa | gaa | tgt | ata | gaa | aca | gct | aca | aga | att | gtt | 869 |
| Ser | Gly | Val | Leu | Val | Lys | Glu | Cys | Ile | Glu | Thr | Ala | Thr | Arg | Ile | Val |
|     |     | 265 |     |     |     |     | 270 |     |     |     |     | 275 |     |     |     |
| cgg | gct | cct | att | ctg | agg | tca | gct | gag | tta | gcc | aat | gag | ctt | gct | agt | 917 |
| Arg | Ala | Pro | Ile | Leu | Arg | Ser | Ala | Glu | Leu | Ala | Asn | Glu | Leu | Ala | Ser |
|     | 280 |     |     |     |     | 285 |     |     |     |     | 290 |     |     |     |     |
| gtc | ttg | cca | gca | aga | ctc | gag | att | caa | tgg | tac | aaa | gat | cgt | tgc | gat | 965 |
| Val | Leu | Pro | Ala | Arg | Leu | Glu | Ile | Gln | Trp | Tyr | Lys | Asp | Arg | Cys | Asp |
| 295 |     |     |     |     | 300 |     |     |     |     | 305 |     |     |     |     | 310 |
| gca | tca | gaa | gag | cag | cta | ggt | tac | tac | gat | ttc | ttc | aaa | cga | tat | tcg | 1013 |
| Ala | Ser | Glu | Glu | Gln | Leu | Gly | Tyr | Tyr | Asp | Phe | Phe | Lys | Arg | Tyr | Ser |
|     |     |     |     | 315 |     |     |     |     | 320 |     |     |     |     | 325 |     |
| ttg | aag | aga | gac | ttt | aaa | gtg | aac | atg | agt | cgc | ata | aga | cta | gct | aag | 1061 |
| Leu | Lys | Arg | Asp | Phe | Lys | Val | Asn | Met | Ser | Arg | Ile | Arg | Leu | Ala | Lys |
|     |     |     | 330 |     |     |     |     | 335 |     |     |     |     | 340 |     |     |
| ttt | tgg | gac | aca | gtg | att | aaa | atg | gtg | gag | acg | aat | gag | tta | cct | ttt | 1109 |
| Phe | Trp | Asp | Thr | Val | Ile | Lys | Met | Val | Glu | Thr | Asn | Glu | Leu | Pro | Phe |
|     |     |     | 345 |     |     |     |     | 350 |     |     |     |     | 355 |     |     |
| gat | ttt | cat | tta | gga | aag | aaa | tgg | att | tac | gca | tct | caa | ttt | tat | caa | 1157 |
| Asp | Phe | His | Leu | Gly | Lys | Lys | Trp | Ile | Tyr | Ala | Ser | Gln | Phe | Tyr | Gln |
|     | 360 |     |     |     |     | 365 |     |     |     |     | 370 |     |     |     |     |
| ctc | tta | gcc | gag | cca | ctc | gac | att | gcg | aat | ttc | tac | aaa | aac | aga | gat | 1205 |
| Leu | Leu | Ala | Glu | Pro | Leu | Asp | Ile | Ala | Asn | Phe | Tyr | Lys | Asn | Arg | Asp |
| 375 |     |     |     |     | 380 |     |     |     |     | 385 |     |     |     |     | 390 |
| ata | aag | act | ggc | ggg | cat | tac | ttg | gag | ggg | aat | aga | cct | aaa | agg | tat | 1253 |
| Ile | Lys | Thr | Gly | Gly | His | Tyr | Leu | Glu | Gly | Asn | Arg | Pro | Lys | Arg | Tyr |
|     |     |     |     | 395 |     |     |     |     | 400 |     |     |     |     | 405 |     |
| gag | gtg | att | gat | aaa | tgg | cag | aaa | gga | gtt | aaa | gtg | cct | gag | gag | tgt | 1301 |
| Glu | Val | Ile | Asp | Lys | Trp | Gln | Lys | Gly | Val | Lys | Val | Pro | Glu | Glu | Cys |
|     |     |     | 410 |     |     |     |     | 415 |     |     |     |     | 420 |     |     |
| gtg | aga | agc | aga | tac | gcg | agc | aca | acg | caa | gat | act | tgc | ttt | tgg | gct | 1349 |
| Val | Arg | Ser | Arg | Tyr | Ala | Ser | Thr | Thr | Gln | Asp | Thr | Cys | Phe | Trp | Ala |
|     |     | 425 |     |     |     |     | 430 |     |     |     |     | 435 |     |     |     |
| aag | ctt | gag | caa | gca | aaa | gag | tgg | ttg | gat | gag | gcg | aga | aaa | gag | agt | 1397 |
| Lys | Leu | Glu | Gln | Ala | Lys | Glu | Trp | Leu | Asp | Glu | Ala | Arg | Lys | Glu | Ser |
|     | 440 |     |     |     |     | 445 |     |     |     |     | 450 |     |     |     |     |
| agt | gat | ccc | cag | agg | aga | tct | ttg | tta | cgg | gaa | aag | att | gtt | cca | ttc | 1445 |
| Ser | Asp | Pro | Gln | Arg | Arg | Ser | Leu | Leu | Arg | Glu | Lys | Ile | Val | Pro | Phe |
| 455 |     |     |     |     | 460 |     |     |     |     | 465 |     |     |     |     | 470 |
| gag | agt | tat | gcg | aat | aca | ttg | gtg | acg | aag | aag | gag | gtt | tct | ttg | gat | 1493 |
| Glu | Ser | Tyr | Ala | Asn | Thr | Leu | Val | Thr | Lys | Lys | Glu | Val | Ser | Leu | Asp |
|     |     |     |     | 475 |     |     |     |     | 480 |     |     |     |     | 485 |     |
| gtt | aaa | gcg | aag | aac | tcg | agt | tat | agt | gtg | tgg | gag | gcg | aat | ctg | aaa | 1541 |
| Val | Lys | Ala | Lys | Asn | Ser | Ser | Tyr | Ser | Val | Trp | Glu | Ala | Asn | Leu | Lys |
|     |     |     | 490 |     |     |     |     | 495 |     |     |     |     | 500 |     |     |
| gag | ttc | aag | tgc | aaa | atg | ggt | tat | gaa | aat | gaa | att | gag | atg | gtt | gtt | 1589 |
| Glu | Phe | Lys | Cys | Lys | Met | Gly | Tyr | Glu | Asn | Glu | Ile | Glu | Met | Val | Val |
|     |     | 505 |     |     |     |     | 510 |     |     |     |     | 515 |     |     |     |
| gat | gag | agt | gac | gca | atg | gag | act | tag | taggactaat | agcaaatcga |     |     |     |     |     | 1636 |

```
Asp Glu Ser Asp Ala Met Glu Thr
    520                 525 atgtttgata tgctatataa caatctgtat cattgttgtt catcatgttt atgcaagact    1696
ttctgatgaa tgttactata tattct                                         1722

<210> SEQ ID NO 2
<211> LENGTH: 526
<212> TYPE: PRT
<213> ORGANISM: Arabidopsis thaliana

<400> SEQUENCE: 2

Met Ile Ser Thr Pro Leu Phe Thr Asp Ser Trp Ser Cys Asn Thr
  1               5                  10                  15

Ala Asn Cys Asn Gly Ser Ile Lys Ile His Asp Ile Ala Gly Ile Thr
             20                  25                  30

Tyr Val Ala Ile Pro Ala Val Ser Met Ile Gln Leu Gly Asn Leu Val
         35                  40                  45

Gly Leu Pro Val Thr Gly Asp Val Leu Phe Pro Gly Leu Ser Ser Asp
     50                  55                  60

Glu Pro Leu Pro Met Val Asp Ala Ala Ile Leu Lys Leu Phe Leu Gln
 65                  70                  75                  80

Leu Lys Ile Lys Glu Gly Leu Glu Leu Glu Leu Leu Gly Lys Lys Leu
                 85                  90                  95

Val Val Ile Thr Gly His Ser Thr Gly Gly Ala Leu Ala Ala Phe Thr
            100                 105                 110

Ala Leu Trp Leu Leu Ser Gln Ser Ser Pro Pro Ser Phe Arg Val Phe
        115                 120                 125

Cys Ile Thr Phe Gly Ser Pro Leu Leu Gly Asn Gln Ser Leu Ser Thr
    130                 135                 140

Ser Ile Ser Arg Ser Arg Leu Ala His Asn Phe Cys His Val Val Ser
145                 150                 155                 160

Ile His Asp Leu Val Pro Arg Ser Ser Asn Glu Gln Phe Trp Pro Phe
                165                 170                 175

Gly Thr Tyr Leu Phe Cys Ser Asp Lys Gly Gly Val Cys Leu Asp Asn
            180                 185                 190

Ala Gly Ser Val Arg Leu Met Phe Asn Ile Leu Asn Thr Thr Ala Thr
        195                 200                 205

Gln Asn Thr Glu Glu His Gln Arg Tyr Gly His Tyr Val Phe Thr Leu
    210                 215                 220

Ser His Met Phe Leu Lys Ser Arg Ser Phe Leu Gly Gly Ser Ile Pro
225                 230                 235                 240

Asp Asn Ser Tyr Gln Ala Gly Val Ala Leu Ala Val Glu Ala Leu Gly
                245                 250                 255

Phe Ser Asn Asp Asp Thr Ser Gly Val Leu Val Lys Glu Cys Ile Glu
            260                 265                 270

Thr Ala Thr Arg Ile Val Arg Ala Pro Ile Leu Arg Ser Ala Glu Leu
        275                 280                 285

Ala Asn Glu Leu Ala Ser Val Leu Pro Ala Arg Leu Glu Ile Gln Trp
    290                 295                 300

Tyr Lys Asp Arg Cys Asp Ala Ser Glu Glu Gln Leu Gly Tyr Tyr Asp
305                 310                 315                 320

Phe Phe Lys Arg Tyr Ser Leu Lys Arg Asp Phe Lys Val Asn Met Ser
                325                 330                 335

Arg Ile Arg Leu Ala Lys Phe Trp Asp Thr Val Ile Lys Met Val Glu
```

```
                       340                 345                 350
Thr Asn Glu Leu Pro Phe Asp Phe His Leu Gly Lys Lys Trp Ile Tyr
            355                 360                 365

Ala Ser Gln Phe Tyr Gln Leu Leu Ala Glu Pro Leu Asp Ile Ala Asn
        370                 375                 380

Phe Tyr Lys Asn Arg Asp Ile Lys Thr Gly Gly His Tyr Leu Glu Gly
385                 390                 395                 400

Asn Arg Pro Lys Arg Tyr Glu Val Ile Asp Lys Trp Gln Lys Gly Val
                405                 410                 415

Lys Val Pro Glu Glu Cys Val Arg Ser Arg Tyr Ala Ser Thr Thr Gln
            420                 425                 430

Asp Thr Cys Phe Trp Ala Lys Leu Glu Gln Ala Lys Glu Trp Leu Asp
        435                 440                 445

Glu Ala Arg Lys Glu Ser Ser Asp Pro Gln Arg Arg Ser Leu Leu Arg
    450                 455                 460

Glu Lys Ile Val Pro Phe Glu Ser Tyr Ala Asn Thr Leu Val Thr Lys
465                 470                 475                 480

Lys Glu Val Ser Leu Asp Val Lys Ala Lys Asn Ser Ser Tyr Ser Val
                485                 490                 495

Trp Glu Ala Asn Leu Lys Glu Phe Lys Cys Lys Met Gly Tyr Glu Asn
            500                 505                 510

Glu Ile Glu Met Val Val Asp Glu Ser Asp Ala Met Glu Thr
        515                 520                 525

<210> SEQ ID NO 3
<211> LENGTH: 1722
<212> TYPE: DNA
<213> ORGANISM: Arabidopsis thaliana
<220> FEATURE:
<221> NAME/KEY: CDS
<222> LOCATION: (36)..(1064)

<400> SEQUENCE: 3
gtcgattcga gacgagtgag ttgcaagctt cggta atg ata tcg act cct tta           53
                                      Met Ile Ser Thr Pro Leu
                                        1               5 ttt acc gat tct tgg agt tca tgc aac acc gca aat tgc aac ggg agt         101
Phe Thr Asp Ser Trp Ser Ser Cys Asn Thr Ala Asn Cys Asn Gly Ser
            10                  15                  20 ata aag atc cat gac atc gcc ggg att aca tac gtt gct ata ccg gcg         149
Ile Lys Ile His Asp Ile Ala Gly Ile Thr Tyr Val Ala Ile Pro Ala
        25                  30                  35 gta tcg atg att cag ttg ggg aat ctt gtg ggc ttg cca gtc acc gga         197
Val Ser Met Ile Gln Leu Gly Asn Leu Val Gly Leu Pro Val Thr Gly
    40                  45                  50 gat gtt ctt ttc ccc ggc tta tcc tcc gat gaa cct cta cct atg gtc         245
Asp Val Leu Phe Pro Gly Leu Ser Ser Asp Glu Pro Leu Pro Met Val
55                  60                  65                  70 gac gct gcc ata ctc aaa ctc ttt ctt cag tta aag atc aag gaa gga         293
Asp Ala Ala Ile Leu Lys Leu Phe Leu Gln Leu Lys Ile Lys Glu Gly
                75                  80                  85 ttg gaa ttg gaa ttg tta ggt aaa aag ctg gtg gtg ata acc ggc cat         341
Leu Glu Leu Glu Leu Leu Gly Lys Lys Leu Val Val Ile Thr Gly His
            90                  95                 100 tca acc ggc ggc gca ttg gcc gct ttc acc gca ctt tgg ctt cta tct         389
Ser Thr Gly Gly Ala Leu Ala Ala Phe Thr Ala Leu Trp Leu Leu Ser
       105                 110                 115 caa tct tct ccg ccg tca ttc cgc gtc ttt tgt atc acc ttt ggc tct         437
```

```
                                                                           -continued
Gln Ser Ser Pro Pro Ser Phe Arg Val Phe Cys Ile Thr Phe Gly Ser
    120                 125                 130 cct ctg ctc gga aac caa tct ctc tcc acc tca att tca cga tca cgt          485
Pro Leu Leu Gly Asn Gln Ser Leu Ser Thr Ser Ile Ser Arg Ser Arg
135                 140                 145                 150 tta gca cac aac ttc tgc cac gtg gtc tcc atc cac gac ctc gtt cct          533
Leu Ala His Asn Phe Cys His Val Val Ser Ile His Asp Leu Val Pro
                155                 160                 165 aga agc agc aat gaa caa ttc tgg ccc ttt gga act tac ttg ttc tgt          581
Arg Ser Ser Asn Glu Gln Phe Trp Pro Phe Gly Thr Tyr Leu Phe Cys
            170                 175                 180 tcc gac aaa gga ggt gtc tgt cta gac aac gct ggt tct gtt cgt ctg          629
Ser Asp Lys Gly Gly Val Cys Leu Asp Asn Ala Gly Ser Val Arg Leu
        185                 190                 195 atg ttt aat atc ctc aac acc aca gca act caa aac acc gag gaa cat          677
Met Phe Asn Ile Leu Asn Thr Thr Ala Thr Gln Asn Thr Glu Glu His
    200                 205                 210 cag agg tac gga cac tat gtg ttc aca ctt tca cac atg ttt ctt aaa          725
Gln Arg Tyr Gly His Tyr Val Phe Thr Leu Ser His Met Phe Leu Lys
215                 220                 225                 230 tct aga agc ttt ctt ggt ggg agt atc ccc gac aat agc tac caa gct          773
Ser Arg Ser Phe Leu Gly Gly Ser Ile Pro Asp Asn Ser Tyr Gln Ala
                235                 240                 245 ggt gtt gcg tta gcc gtt gaa gct cta ggt ttc tct aac gat gac aca          821
Gly Val Ala Leu Ala Val Glu Ala Leu Gly Phe Ser Asn Asp Asp Thr
            250                 255                 260 agt ggc gtt tta gtc aaa gaa tgt ata gaa aca gct aca aga att gtt          869
Ser Gly Val Leu Val Lys Glu Cys Ile Glu Thr Ala Thr Arg Ile Val
        265                 270                 275 cgg gct cct att ctg agg tca gct gag tta gcc aat gag ctt gct agt          917
Arg Ala Pro Ile Leu Arg Ser Ala Glu Leu Ala Asn Glu Leu Ala Ser
    280                 285                 290 gtc ttg cca gca aga ctc gag att caa tgg tac aaa gat cgt tgc gat          965
Val Leu Pro Ala Arg Leu Glu Ile Gln Trp Tyr Lys Asp Arg Cys Asp
295                 300                 305                 310 gca tca gaa gag cag cta ggt tac tac gat ttc ttc aaa cga tat tcg         1013
Ala Ser Glu Glu Gln Leu Gly Tyr Tyr Asp Phe Phe Lys Arg Tyr Ser
                315                 320                 325 ttg aag aga gac ttt aaa gtg aac atg agt cgc ata aga cta gct aag         1061
Leu Lys Arg Asp Phe Lys Val Asn Met Ser Arg Ile Arg Leu Ala Lys
            330                 335                 340 ttt tag gacacagtga ttaaaatggt ggagacgaat gagttacctt ttgattttca          1117
Phe tttaggaaag aaatggattt acgcatctca attttatcaa ctcttagccg agccactcga       1177
cattgcgaat ttctacaaaa acagagatat aaagactggc gggcattact tggaggggaa       1237
tagacctaaa aggtatgagg tgattgataa atggcagaaa ggagttaaag tgcctgagga       1297
gtgtgtgaga agcagatacg cgagcacaac gcaagatact tgcttttggg ctaagcttga       1357
gcaagcaaaa gagtggttgg atgaggcgag aaaagagagt agtgatcccc agaggagatc       1417
tttgttacgg gaaaagattg ttccattcga gagttatgcg aatacattgg tgacgaagaa       1477
ggaggtttct ttggatgtta aagcgaagaa ctcgagttat agtgtgtggg aggcgaatct       1537
gaaagagttc aagtgcaaaa tgggttatga aaatgaaatt gagatggttg ttgatgagag       1597
tgacgcaatg gagacttagt aggactaata gcaaatcgaa tgtttgatat gctatataac       1657
aatctgtatc attgttgttc atcatgttta tgcaagactt tctgatgaat gttactatat       1717
attct                                                                    1722
```

```
<210> SEQ ID NO 4
<211> LENGTH: 343
<212> TYPE: PRT
<213> ORGANISM: Arabidopsis thaliana

<400> SEQUENCE: 4

Met Ile Ser Thr Pro Leu Phe Thr Asp Ser Trp Ser Ser Cys Asn Thr
  1               5                  10                  15

Ala Asn Cys Asn Gly Ser Ile Lys Ile His Asp Ile Ala Gly Ile Thr
                 20                  25                  30

Tyr Val Ala Ile Pro Ala Val Ser Met Ile Gln Leu Gly Asn Leu Val
             35                  40                  45

Gly Leu Pro Val Thr Gly Asp Val Leu Phe Pro Gly Leu Ser Ser Asp
         50                  55                  60

Glu Pro Leu Pro Met Val Asp Ala Ala Ile Leu Lys Leu Phe Leu Gln
 65                  70                  75                  80

Leu Lys Ile Lys Glu Gly Leu Glu Leu Glu Leu Leu Gly Lys Lys Leu
                 85                  90                  95

Val Val Ile Thr Gly His Ser Thr Gly Gly Ala Leu Ala Ala Phe Thr
            100                 105                 110

Ala Leu Trp Leu Leu Ser Gln Ser Pro Pro Ser Phe Arg Val Phe
            115                 120                 125

Cys Ile Thr Phe Gly Ser Pro Leu Leu Gly Asn Gln Ser Leu Ser Thr
        130                 135                 140

Ser Ile Ser Arg Ser Arg Leu Ala His Asn Phe Cys His Val Val Ser
145                 150                 155                 160

Ile His Asp Leu Val Pro Arg Ser Ser Asn Glu Gln Phe Trp Pro Phe
                165                 170                 175

Gly Thr Tyr Leu Phe Cys Ser Asp Lys Gly Gly Val Cys Leu Asp Asn
            180                 185                 190

Ala Gly Ser Val Arg Leu Met Phe Asn Ile Leu Asn Thr Thr Ala Thr
        195                 200                 205

Gln Asn Thr Glu Glu His Gln Arg Tyr Gly His Tyr Val Phe Thr Leu
    210                 215                 220

Ser His Met Phe Leu Lys Ser Arg Ser Phe Leu Gly Gly Ser Ile Pro
225                 230                 235                 240

Asp Asn Ser Tyr Gln Ala Gly Val Ala Leu Ala Val Glu Ala Leu Gly
                245                 250                 255

Phe Ser Asn Asp Asp Thr Ser Gly Val Leu Val Lys Glu Cys Ile Glu
            260                 265                 270

Thr Ala Thr Arg Ile Val Arg Ala Pro Ile Leu Arg Ser Ala Glu Leu
        275                 280                 285

Ala Asn Glu Leu Ala Ser Val Leu Pro Ala Arg Leu Glu Ile Gln Trp
    290                 295                 300

Tyr Lys Asp Arg Cys Asp Ala Ser Glu Glu Gln Leu Gly Tyr Tyr Asp
305                 310                 315                 320

Phe Phe Lys Arg Tyr Ser Leu Lys Arg Asp Phe Lys Val Asn Met Ser
                325                 330                 335

Arg Ile Arg Leu Ala Lys Phe
            340

<210> SEQ ID NO 5
<211> LENGTH: 11168
<212> TYPE: DNA
```

-continued

```
<213> ORGANISM: Arabidopsis thaliana
<220> FEATURE:
<221> NAME/KEY: unsure
<222> LOCATION: (7327)
<223> OTHER INFORMATION: n = g or a or c or t
<220> FEATURE:
<221> NAME/KEY: unsure
<222> LOCATION: (7423)
<223> OTHER INFORMATION: n = g or a or c or t
<220> FEATURE:
<221> NAME/KEY: unsure
<222> LOCATION: (8753)
<223> OTHER INFORMATION: n = g or a or c or t
<220> FEATURE:
<221> NAME/KEY: unsure
<222> LOCATION: (8755)
<223> OTHER INFORMATION: n = g or a or c or t
<220> FEATURE:
<221> NAME/KEY: unsure
<222> LOCATION: (8768)
<223> OTHER INFORMATION: n = g or a or c or t
<220> FEATURE:
<221> NAME/KEY: unsure
<222> LOCATION: (8774)
<223> OTHER INFORMATION: n = g or a or c or t
<220> FEATURE:
<221> NAME/KEY: unsure
<222> LOCATION: (8776)
<223> OTHER INFORMATION: n = g or a or c or t
<220> FEATURE:
<221> NAME/KEY: unsure
<222> LOCATION: (8784)
<223> OTHER INFORMATION: n = g or a or c or t
<220> FEATURE:
<221> NAME/KEY: unsure
<222> LOCATION: (8796)
<223> OTHER INFORMATION: n = g or a or c or t
<220> FEATURE:
<221> NAME/KEY: unsure
<222> LOCATION: (8799)
<223> OTHER INFORMATION: n = g or a or c or t
<220> FEATURE:
<221> NAME/KEY: unsure
<222> LOCATION: (9030)
<223> OTHER INFORMATION: n = g or a or c or t
<220> FEATURE:
<221> NAME/KEY: unsure
<222> LOCATION: (9325)
<223> OTHER INFORMATION: n = g or a or c or t
<220> FEATURE:
<221> NAME/KEY: unsure
<222> LOCATION: (9466)
<223> OTHER INFORMATION: n = g or a or c or t
<220> FEATURE:
<221> NAME/KEY: unsure
<222> LOCATION: (9480)
<223> OTHER INFORMATION: n = g or a or c or t
<220> FEATURE:
<221> NAME/KEY: unsure
<222> LOCATION: (10178)
<223> OTHER INFORMATION: n = g or a or c or t
<220> FEATURE:
<221> NAME/KEY: unsure
<222> LOCATION: (10289)
<223> OTHER INFORMATION: n = g or a or c or t
<220> FEATURE:
<221> NAME/KEY: unsure
<222> LOCATION: (10322)
<223> OTHER INFORMATION: n = g or a or c or t
<220> FEATURE:
<221> NAME/KEY: unsure
<222> LOCATION: (10360)
<223> OTHER INFORMATION: n = g or a or c or t
<220> FEATURE:
<221> NAME/KEY: unsure
<222> LOCATION: (10372)
<223> OTHER INFORMATION: n = g or a or c or t
<220> FEATURE:
<221> NAME/KEY: unsure
```

```
<222> LOCATION: (10382)
<223> OTHER INFORMATION: n = g or a or c or t
<220> FEATURE:
<221> NAME/KEY: unsure
<222> LOCATION: (10384)
<223> OTHER INFORMATION: n = g or a or c or t
<220> FEATURE:
<221> NAME/KEY: CDS
<222> LOCATION: (1722)..(1967)
<223> OTHER INFORMATION: First Exon of PAD4
<220> FEATURE:
<221> NAME/KEY: CDS
<222> LOCATION: (3070)..(4407)
<223> OTHER INFORMATION: Second Exon of PAD4
<220> FEATURE:
<221> NAME/KEY: CDS
<222> LOCATION: (5637)..(5816)
<223> OTHER INFORMATION: Sequence of Zinc Finger Homology Region

<400> SEQUENCE: 5
```

| | | | | | |
|---|---|---|---|---|---|
| tcgacaaatc | tgacccaacc | aaagaccccg | atgacttcga | caccgccgct | actgcaacca | 60 |
| catccaaaga | gggtttgtaa | aattagggtt | ttatcagatt | aaagagattt | actgatttca | 120 |
| atccatttca | tgtaactgat | gaatccatgt | gttcttaatc | ataacagttt | gagcaatttc | 180 |
| ttttgagtca | tgatcgttta | tttgtcatca | atttttggaa | aagtctgcta | tattgaatct | 240 |
| gttattgtag | ttcaatcgca | taacagaatc | attaatctaa | tcaatattca | tacatgattt | 300 |
| gttacaccgt | ttttcgtatt | ttgtataaag | tttcgagctg | tattattaag | gtggaagaag | 360 |
| agattaggaa | tccgataagt | acttaaattg | ttttaagtta | tgattcgatt | atacgtatct | 420 |
| cttgaaaaga | agcatgttag | agcaaaatat | caaacttgac | aattacaaga | ttgctttata | 480 |
| gataaagcag | attagctaaa | taagtatagg | gagacgataa | catgtggtga | tacaaagatg | 540 |
| tgtcagattg | attgtttaac | atcatttagt | tgagaaaact | ttggacgacg | actgacttca | 600 |
| tcatatgaga | aaacaccaag | aaaatgtact | actagtctct | aatggagaga | cttggttata | 660 |
| gaagttcatt | gtttaatttg | aatatttact | ccaattcagg | aaaatatcaa | accagaaaa | 720 |
| ttacatgaaa | attactatag | atggtagctt | tgcaatgatt | attgtccggt | tggatagttt | 780 |
| cattgacatt | taggattcag | attatctctt | ttatcattat | cagtttgtta | aggcaagagt | 840 |
| tttctaatac | atgcttaagt | cctaatcatc | agatatttct | tcttcaaacc | ttttttgttt | 900 |
| tgttttgata | atttgcccca | ttttgtactc | taggtttttc | cacaaagatc | ccaaacagag | 960 |
| attaaaagat | gacaatggca | tggaccttc | aatgctttgt | ttttttgtta | aattagatat | 1020 |
| aaacctttcc | aaacagtaaa | ttatcaaatt | cattaacaag | tatctatatc | tctctagtag | 1080 |
| aggtagacca | caacttaaaa | atctcctcaa | gtcatggtgg | gtctaacttg | taggacttat | 1140 |
| atgggccaaa | ttgtataact | atatcatgtt | aagctgaaac | tgaaagtaat | tggttccttt | 1200 |
| taaaagctta | gccaaaaaaa | cttcaaaatg | tctgagtcaa | atgtaggttg | atttctctgc | 1260 |
| aatttccatg | aaagatagat | agataaactc | ttaccaaagt | ttctgcatat | caaaagttgt | 1320 |
| caatttatgc | tcaagtctaa | accattccga | ttacatagga | tcacatgctt | tgattcgcat | 1380 |
| tttcttctac | tatatattta | catatttttt | tgtcctctac | acacaatgat | taaaaatga | 1440 |
| gaatggacct | acctttcaca | gcatttcttt | attattattt | tataaaacca | gtacaatttt | 1500 |
| actaaattat | gatgttaaag | taagagactt | tgaagaagac | gacttagcaa | agaccaaaac | 1560 |
| caagaaatta | cataggaaca | agccaagaag | atacatagat | aatttctttt | tgcttgtaat | 1620 |
| atatttacaa | cttcataaac | atcatcgttc | tgcaactctc | tactcgatat | ccaatcatgg | 1680 |
| acgattgtcg | attcgagacg | agtgagttgc | aagcttcggt | a atg ata tcg act cct | | 1736 |
| | | | | Met Ile Ser Thr Pro | | |

-continued

|  |  |  |  |  | 1 |  |  | 5 |  |  |  |  |  |  |  |
|---|---|---|---|---|---|---|---|---|---|---|---|---|---|---|---|
| tta | ttt | acc | gat | tct | tgg | agt | tca | tgc | aac | acc | gca | aat | tgc | aac | ggg |
| Leu | Phe | Thr | Asp | Ser | Trp | Ser | Ser | Cys | Asn | Thr | Ala | Asn | Cys | Asn | Gly |
|  |  |  |  | 10 |  |  |  | 15 |  |  |  |  | 20 |  |  | 1784 agt ata aag atc cat gac atc gcc ggg att aca tac gtt gct ata ccg    1832
Ser Ile Lys Ile His Asp Ile Ala Gly Ile Thr Tyr Val Ala Ile Pro
        25                  30                  35 gcg gta tcg atg att cag ttg ggg aat ctt gtg ggc ttg cca gtc acc    1880
Ala Val Ser Met Ile Gln Leu Gly Asn Leu Val Gly Leu Pro Val Thr
            40                  45                  50 gga gat gtt ctt ttc ccc ggc tta tcc tcc gat gaa cct cta cct atg    1928
Gly Asp Val Leu Phe Pro Gly Leu Ser Ser Asp Glu Pro Leu Pro Met
 55                  60                  65 gtc gac gct gcc ata ctc aaa ctc ttt ctt cag tta aag ggtttgtttt    1977
Val Asp Ala Ala Ile Leu Lys Leu Phe Leu Gln Leu Lys
 70                  75                  80 ctcttcctct gkkkttttttt ctttctattg gatgcaattt aacctattta ttatcttcaa    2037
ggcatgtgga tatttgaatt tcaattaata atacctcgag agaaaaatac aaaaatcatt    2097
aaatgctaat atgggaaatt atttcacaaa ggattttaaa aaaaaacaaa attctatcat    2157 aagtttatt cgtttggatt tgcgaaaacg aattttacct attaaagtta ctattttttt    2217
tacgtatttt agtactttt agtagaactg atgatcatta ctattttta tttaaatatc    2277 tctgtcctct gaattttgat gaattataat ccaaatggag gtttttttg tccttttaaa    2337 agattattat aaactatcac caccacctac cccaataggc aatagacaat agataataaa    2397
taaaaattat tttcttgtaa gaaattctaa aaagattcgt ggacacaatt attccaaatc    2457
caccatttgg aatatgtcat tgtcgcgacc tttggatatc ataagcaagt caattgaaag    2517
tttggtttgt atgccatcac gtccgtccgc ccaagtgatt taaaaaattt actaattagt    2577
gagtgaaacg tcattggtat ttttgacacc aaaaaaaaca aaaaatgtta atggaattgg    2637
tagctttacg ctttatgctt taacacacct cggcgaagtt tataaatgtg cgctcaaaaa    2697 gttttttaacc catgattatt gtgtcaccat catgtatttt attcccttt tcgtcgaata    2757 cttttagttt ttgttttgtc tctaaggata tgaaaatctt gaacaaaaac aagttcctat    2817
tggttttgat gagtagaaaa aacaagaagt gaccattaat gtagatataa gttgtaaaaa    2877
tggtaagtct agagaggtgt cttaactgat ttttattcaa atttggttaa accaagtaat    2937
tggcaaattt agtctctaaa tcagtttaca ttattagagg aaattgtaca ctcagaagga    2997
aggtaatcta taatcagttt tgttcttgtt agtcaaccaa tttacagtaa cgtcgactgc    3057

| attaacgtgc | ag | atc | aag | gaa | gga | ttg | gaa | ttg | gaa | ttg | tta | ggt | aaa | aag | 3108 |
|---|---|---|---|---|---|---|---|---|---|---|---|---|---|---|---|
|  |  | Ile | Lys | Glu | Gly | Leu | Glu | Leu | Glu | Leu | Leu | Gly | Lys | Lys |  |
|  |  |  | 85 |  |  |  |  | 90 |  |  |  |  |  | 95 |  | ctg gtg gtg ata acc ggc cat tca acc ggc ggc gca ttg gcc gct ttc    3156
Leu Val Val Ile Thr Gly His Ser Thr Gly Gly Ala Leu Ala Ala Phe
            100                 105                 110 acc gca ctt tgg ctt cta tct caa tct tct ccg ccg tca ttc cgc gtc    3204
Thr Ala Leu Trp Leu Leu Ser Gln Ser Ser Pro Pro Ser Phe Arg Val
        115                 120                 125 ttt tgt atc acc ttt ggc tct cct ctg ctc gga aac caa tct ctc tcc    3252
Phe Cys Ile Thr Phe Gly Ser Pro Leu Leu Gly Asn Gln Ser Leu Ser
    130                 135                 140 acc tca att tca cga tca cgt tta gca cac aac ttc tgc cac gtg gtc    3300
Thr Ser Ile Ser Arg Ser Arg Leu Ala His Asn Phe Cys His Val Val
145                 150                 155 tcc atc cac gac ctc gtt cct aga agc agc aat gaa caa ttc tgg ccc    3348

```
                                                              -continued

Ser Ile His Asp Leu Val Pro Arg Ser Ser Asn Glu Gln Phe Trp Pro
160                 165                 170                 175 ttt gga act tac ttg ttc tgt tcc gac aaa gga ggt gtc tgt cta gac        3396
Phe Gly Thr Tyr Leu Phe Cys Ser Asp Lys Gly Gly Val Cys Leu Asp
                    180                 185                 190 aac gct ggt tct gtt cgt ctg atg ttt aat atc ctc aac acc aca gca        3444
Asn Ala Gly Ser Val Arg Leu Met Phe Asn Ile Leu Asn Thr Thr Ala
                195                 200                 205 act caa aac acc gag gaa cat cag agg tac gga cac tat gtg ttc aca        3492
Thr Gln Asn Thr Glu Glu His Gln Arg Tyr Gly His Tyr Val Phe Thr
            210                 215                 220 ctt tca cac atg ttt ctt aaa tct aga agc ttt ctt ggt ggg agt atc        3540
Leu Ser His Met Phe Leu Lys Ser Arg Ser Phe Leu Gly Gly Ser Ile
        225                 230                 235 ccc gac aat agc tac caa gct ggt gtt gcg tta gcc gtt gaa gct cta        3588
Pro Asp Asn Ser Tyr Gln Ala Gly Val Ala Leu Ala Val Glu Ala Leu
240                 245                 250                 255 ggt ttc tct aac gat gac aca agt ggc gtt tta gtc aaa gaa tgt ata        3636
Gly Phe Ser Asn Asp Asp Thr Ser Gly Val Leu Val Lys Glu Cys Ile
                    260                 265                 270 gaa aca gct aca aga att gtt cgg gct cct att ctg agg tca gct gag        3684
Glu Thr Ala Thr Arg Ile Val Arg Ala Pro Ile Leu Arg Ser Ala Glu
                275                 280                 285 tta gcc aat gag ctt gct agt gtc ttg cca gca aga ctc gag att caa        3732
Leu Ala Asn Glu Leu Ala Ser Val Leu Pro Ala Arg Leu Glu Ile Gln
            290                 295                 300 tgg tac aaa gat cgt tgc gat gca tca gaa gag cag cta ggt tac tac        3780
Trp Tyr Lys Asp Arg Cys Asp Ala Ser Glu Glu Gln Leu Gly Tyr Tyr
        305                 310                 315 gat ttc ttc aaa cga tat tcg ttg aag aga gac ttt aaa gtg aac atg        3828
Asp Phe Phe Lys Arg Tyr Ser Leu Lys Arg Asp Phe Lys Val Asn Met
320                 325                 330                 335 agt cgc ata aga cta gct aag ttt tgg gac aca gtg att aaa atg gtg        3876
Ser Arg Ile Arg Leu Ala Lys Phe Trp Asp Thr Val Ile Lys Met Val
                    340                 345                 350 gag acg aat gag tta cct ttt gat ttt cat tta gga aag aaa tgg att        3924
Glu Thr Asn Glu Leu Pro Phe Asp Phe His Leu Gly Lys Lys Trp Ile
                355                 360                 365 tac gca tct caa ttt tat caa ctc tta gcc gag cca ctc gac att gcg        3972
Tyr Ala Ser Gln Phe Tyr Gln Leu Leu Ala Glu Pro Leu Asp Ile Ala
            370                 375                 380 aat ttc tac aaa aac aga gat ata aag act ggc ggg cat tac ttg gag        4020
Asn Phe Tyr Lys Asn Arg Asp Ile Lys Thr Gly Gly His Tyr Leu Glu
        385                 390                 395 ggg aat aga cct aaa agg tat gag gtg att gat aaa tgg cag aaa gga        4068
Gly Asn Arg Pro Lys Arg Tyr Glu Val Ile Asp Lys Trp Gln Lys Gly
400                 405                 410                 415 gtt aaa gtg cct gag gag tgt gtg aga agc aga tac gcg agc aca acg        4116
Val Lys Val Pro Glu Glu Cys Val Arg Ser Arg Tyr Ala Ser Thr Thr
                    420                 425                 430 caa gat act tgc ttt tgg gct aag ctt gag caa gca aaa gag tgg ttg        4164
Gln Asp Thr Cys Phe Trp Ala Lys Leu Glu Gln Ala Lys Glu Trp Leu
                435                 440                 445 gat gag gcg aga aaa gag agt agt gat ccc cag agg aga tct ttg tta        4212
Asp Glu Ala Arg Lys Glu Ser Ser Asp Pro Gln Arg Arg Ser Leu Leu
            450                 455                 460 cgg gaa aag att gtt cca ttc gag agt tat gcg aat aca ttg gtg acg        4260
Arg Glu Lys Ile Val Pro Phe Glu Ser Tyr Ala Asn Thr Leu Val Thr
        465                 470                 475
```

-continued

| | |
|---|---|
| aag aag gag gtt tct ttg gat gtt aaa gcg aag aac tcg agt tat agt<br>Lys Lys Glu Val Ser Leu Asp Val Lys Ala Lys Asn Ser Ser Tyr Ser<br>480                        485                    490                        495 | 4308 |
| gtg tgg gag gcg aat ctg aaa gag ttc aag tgc aaa atg ggt tat gaa<br>Val Trp Glu Ala Asn Leu Lys Glu Phe Lys Cys Lys Met Gly Tyr Glu<br>                    500                    505                    510 | 4356 |
| aat gaa att gag atg gtt gtt gat gag agt gac gca atg gag act tag<br>Asn Glu Ile Glu Met Val Val Asp Glu Ser Asp Ala Met Glu Thr<br>515                      520                    525 | 4404 |
| tag gactaatagc aaatcgaatg tttgatatgc tatataacaa tctgtatcat | 4457 |
| tgttgttcat catgtttatg caagactttc tgatgaatgt tactatatat tctaaaacaa | 4517 |
| aatttatcgt caatgttcaa caagttttgc aagagtttct ttttttgtgc aatgtgcaaa | 4577 |
| gagtttctca tgtagagcta ttgctctctt tttttttttt ttggtgagaa gtaaagctat | 4637 |
| tactctaaaa ccaacatgta gtgtgatggt gatctaattt caggaatttt agaatacaaa | 4697 |
| tatatagaaa aacgtaagac ctactacata gaattcttgg agattgccaa tatttacatg | 4757 |
| atccaagaag ctctttatcc cattcagatt ttcctttcca atccccattt ttctgtgggt | 4817 |
| taataaatca aataaattca agtcaaataa gtagacaaat agagacagtc cttgttcttc | 4877 |
| aaaacttgtg tcttcttgtt tcaccttctc gttctatagt ttctattcac agatcgttac | 4937 |
| gcatacctta cataccattt tcatactata tactattata taattatgac tatctatgat | 4997 |
| tcgttatcta caagttctga ttcttaacga ctctggccaa atattcatcg tcctctcgcg | 5057 |
| aatataatgt gaatagaaaa tgttgcaata tagataactc atggtttagt acttattgat | 5117 |
| atgaatattt tacttaatat gattgtaagt acattctatt aattttaaaa gacatatatt | 5177 |
| aatcgtgcag catccataaa ctaagccgta caaatagctc aatgtacacc caataaccca | 5237 |
| tctctccaaa gaggccatag gcttcttagt tcccttcgaa acaatctcca agacgatcta | 5297 |
| ttttcttatt catatcttat gataaaaaaa acaaatacta gtatttaaat atctatcaaa | 5357 |
| gattcaaaac ccttaaccct gtctccccca agaagcaaca gtgagtgcac ccttacgagg | 5417 |
| catttgctcc ccccaaactt catccactct ctagcctcca cgcgtctcaa actctccaca | 5477 |
| tgcacaaact ctcacccaca cattcatgca tgcgtatata atacattcgg tattccgata | 5537 |
| gactaaagaa gagccgagag agatatggag agagcagagg ccttgacatc atcgtttata | 5597 |
| tggcggccaa acgcaaacgc aaacgcggag atcacgccg agt tgt cca aga tgt<br>                                                          Ser Cys Pro Arg Cys<br>                                                                         530 | 5651 |
| gga tcc tct aac aca aag ttc tgt tac tac aac aac tat agc ctc act<br>Gly Ser Ser Asn Thr Lys Phe Cys Tyr Tyr Asn Asn Tyr Ser Leu Thr<br>535                        540                    545 | 5699 |
| cag cct cgc tac ttc tgc aaa ggc tgc cgc aga tat tgg acc aaa ggt<br>Gln Pro Arg Tyr Phe Cys Lys Gly Cys Arg Arg Tyr Trp Thr Lys Gly<br>550                      555                    560                    565 | 5747 |
| ggt tcc ctc cgc aat gtt cct gta ggc ggt ggc tgt cga aaa tcc cgc<br>Gly Ser Leu Arg Asn Val Pro Val Gly Gly Gly Cys Arg Lys Ser Arg<br>                    570                    575                    580 | 5795 |
| cgc ccc aaa tca tct tct ggt aacaatacta aaactagcct aaccgctaat<br>Arg Pro Lys Ser Ser Ser Gly<br>585 | 5846 |
| tctggcaacc ccggtggtgg ttcaccaagc atcgatcttg ctcttgttta cgccaatttc | 5906 |
| ttgaatccaa agcctgacga atctatacta caagaaaatt gcgacttagc cactacggat | 5966 |
| tttttggtag ataatcctac cggcacttcc atggacccctt catggagtat ggacatcaat | 6026 |
| gatggtcatc atgatcatta tattaatccg gtggaacaca ttgtgaggga atgtggttat | 6086 |

```
aatggcttgc ctccatttcc tggtgaagag cttctctctt tagacactaa tggtgtttgg    6146
tctgatgctt tgttgattgg tcataaccat gtagacgttg gcgtgactcc ggttcaggct    6206
gtacacgaac cggtggttca tttcgctgac gaatccaatg attccaccaa tctcttgttt    6266
ggaagttgga gccctttga tttcactgcc gatggatgat ccttatattt gcatataaat     6326
ttatgaattt gtgttattgt acctattata caaagaatga tatacacgat tatatgaaat    6386
tctatagatc atttcatgta attaagaaag tcgataaatt ttaagtacaa atttaagggg    6446
taataatatg tgtactctac agatcattat ttattttggt tattcagtcg ttttgaagat    6506
ttcctcaaga atcccacgtg gaggtccttg tctttggatt cgattgagat ttgcttcgtt    6566
acttgaactt gtacaattca gagaaagtga gacgcacgtg tatcacggtt gcacgtgtga    6626
gagcctgtta gtatctctgg cctgtgtaga tccttctcca aaagggagt gtcagagaaa     6686 gagcatattt gttcctactt ttctttcaac tcctttctac atgaaaagaa aagaaaaat     6746 gtgatatatc acaagagttg ttttttattt attagagatt tataaataca atttaggccg    6806
tttacatgcg aaatccaatt ctctatgaat tgaacacttt cttagcttaa gcctcgtatt    6866
cctattcata ttgccaactg ttagaggcaa acaaaaaact catctctcaa gaacgaagat    6926
agaccctcgc taccataaca ccgccacttc aacagcattt taatgtttat acacaactaa    6986
tgtacatata cattttaca gccatttgt gaaataaatc ctgtaattga gacttattta      7046
caatggctgt cactggattt taatgtttga ttttgataat taaaaaaaaa atattcgaat    7106
taaatatttg gcatttaaca atgttcccta aatctctcca cattaactac acgattagtt    7166
cctaaaataa aactttcaaa atatttaata tcatttaatt actacaaaat tatcattttt    7226
gatattgctt ttctccatga ctataacaat tcgattataa tcatcaaatc gcagagatat    7286
atgatagcat ttacttacta taaaattaca aaatatttag ncaataattc ataaacatat    7346
cataaataag atcaatatta ataaaataaa tggttttttt acgggacgga ttggcgggag    7406
gggtttggca ggacgtnact taataacaat tgtaaactat raaataraaa tattttatag    7466
atagatmcaa tttacaaamt tttatgtata ctaactttta aaaatatatt gttcttgcgg    7526
tacaccgcgg gttaaaatct agttacttca ttaattgtgt aaacattacg gaagccttct    7586
ttttggtcag agtattatga aacctaaacg ataataaatt gtcaaaaacg aaaaaaacga    7646
aaatactata gatttggtga gctagaatgg aaaaaattac gcaacttgag ttcagaggta    7706
ggcggcaaag aagttaactt ggaaagttgt tcatcatcga gcttcgtgtc acacacgttc    7766
cccatacatc tccgcttgat ccaagaatta tattactaaa gaaacagtt gtgcatttaa     7826 aatttgttaa ataaaatttt gaattgttta gattgaaatg ggtggaggag aatatgaact    7886
attctataga caacatgata cttaaacact gatcttagac tctgataaag taattcaagc    7946
agaaatagtt tctggtgttc ctatagtcta catggttaca tgaatgtaaa actgatcaga    8006
catgcatgaa gaggattgca tggcatatca aagttttctt tggcttgaga agtttatatc    8066
aaatgtatgg agatagcgtg gaggtgagta tcggaagaat atgaaattat gaagaagcag    8126
agaagattac caaaackgga agatttwatg gtatcawtcg tatcaggaag gaaggttgaa    8186
tactgagaga tatactcggg cttaatttgt aatatgcttt tgagggtagc tgaaaaacaa    8246
tctcagaaaa acaatacgta tagtaggtga tcatttggct atgggccatt tcattgttgt    8306
tgaaacagag ttctaaaagg ctttttggt agaactaggg tttggagatt aacaaaccaa     8366
agtcttgtct tggtgtatat atctgtttct aaggttttgt cacttgaaga tatcaaattg    8426
```

-continued

```
agataattat ctgcttttt cagaatgtta gcctacatta tagagtgaaa ttagctagcc      8486
ttaacggatc ggtaatttta tgtataacct tcagcttttg ggaaagcttg tgtatggaaa      8546
aacttggatt aggaagggag aagtataaat tttgaaactt ttgtttagtt gtattttcta      8606
tttttcttgt acgtaatggc tcaaagatca tagaatatag aaaactttgt atctacacaa      8666
ctctttataa ctatctttct ttttctgtt tacaaaaaaa aaaaaaacta tctttctttt       8726
ttctgtctaa ttctacgcaa tgaggtntnt ttcggttgtg tntaattntn cccaatgngg      8786
tttttcggtn ggnaaattat cattgtatga aattattaac catatcaagt aaattcttaa     8846
cgcatcatag atattttctc ggttccaaac cacaagagca atacatttat taatgtatga     8906
ttctcatatt aattttaaat tattaaatta atatcagcaa acaaaacaaa taattttcta     8966
aaaaattctc aaaattacag ttttgacata aataagctt tcaaaaaaaa caaaaaaggg       9026
gatncgagtc aaacgtagcc accgccatgt aatccaagtc ttcgtgtcga cttaacgtcc     9086
ttgaacattt taacattaca tgaaatggaa ttataaatta caagttctta taaccataca     9146
ttatacacta gctagtcctt cacgttcaca tttatatgtg aacctactac atacacgcgc     9206 atgtatttt gtggatgtag tatatatgtc acgcgcatgt atttcaaaaa gttttgtcaa      9266
ctgtggatat tctctccata acgttgtaac tacaactgca agttgtggtc gaggctggnc     9326
caatttcgta gtttttaact cttatttaga ttgcgacatg gttgctcgta agatctgact    9386
ttggattcat gacatttatt atatacaact aaaaattaag tatttttaga aaaaattata     9446
caagtcccta tatataatgn gatatagcca aatnaagtga gaatgatggk caatactcag    9506
ctgctggtgk cttaawtttt gctaatagga tttcatgktt ttggtgcata aattattctc    9566
aataactaaa aggagattac aatttgattt ttaactagaa aacacactgt aactggacca     9626
cccatgttac tgctcatgtg ggtdacactt ttattcaatc ttaacatatg ctgttgttct    9686
tacacttata ttgaatgctt ttttgttaag aatataaata ttttgttaaa aataaaatg      9746 ttaggagtta caatgaagta aattctatga tctagtcttg tgataaaaaa aataattaaa     9806
aaaaaaacat agaagaaaaa aacaatcaat tcatcaacgt cgrccaaaat attttttgtcg    9866 attctgataa aacgatttta ttttatttta tatttttga attgcatgtt ctgaaattga      9926
tctgtatcaa ctatcaagta tgtatagata tacctgatta tattaataaa agaatataaa    9986
gacaaattca taagtcagtg ttggaagagt aaattcgagt gtaatccaaa ttaactttga    10046
catgagcgat tatttatgta aaaccttagg aatttatatt ggacttatag cccgaaagta    10106
ataattaatt ttctcaggta aaacgacact gtactcatgt tctcccccaa gaccatgttc   10166
cctgattgct angaaccgag gtgtataaat acagagattc ttgctatata atattgctat   10226
aacgtgcttt agattcctat attcatctat cttttgcctt cgatctaccg ataatgaaat   10286
gtntattgat cgttaaaacg catgcaaaga gttttngtaa acagttttta ccacgtttag   10346
tttaaatcat tttnaactga gtgatntaaa aaatcncnat aagtgaatac aaaatcrcat   10406
atatatgaag acttttggg tatgtttaca taataattaa gaaacaaat cttaattaag      10466 aatttcttaa aacagaaact catcctcgaa tgaaagaatg cccgtcgtgg atatcgtcga    10526
tgtatactgg aatatataaa tcaatagtgg gattagagtt gtagaacgta ccgacataat     10586
atatatatat atacataatt acattcgcaa tgttacaatt ctggcatcaa ttaaatggtc   10646
agaaacgtta cacatgacgc atacaaatct ctaaaagtat ttgtaaaaag taatggtttt   10706
agcaraacta tgatgtaacc tttaggttat ccactcaata aaaacgagaa gttgaaagag   10766
atgttctcca ttattattgt gagtaatgga caaaagaat ataaataagg agcctctaac    10826
```

```
aattacgaac aargcaagtg ggataaaata gccatgtaac ctgtgaatcc atttatttct   10886
ttgcagtttt ttcataatyt catgaaaata tgtccactat tatctacaca taatgataaa   10946
cattgaaaga taataaaaca aaaacaaatg gaaagaaaat caggagtttg agcaaaattt   11006
ammccactct tttttgtttt aaaatgaact tatacgaaga ataattctca aagaattgtt   11066
tgtatctgat gagaattatt caaacatgta cgttgttcaa gcaggatacg aatcatrcaa   11126
atttcttggg acacaaggtg attccctcca aaccctagcg tg                      11168
```

```
<210> SEQ ID NO 6
<211> LENGTH: 60
<212> TYPE: PRT
<213> ORGANISM: Arabidopsis thaliana

<400> SEQUENCE: 6

Ser Cys Pro Arg Cys Gly Ser Ser Asn Thr Lys Phe Cys Tyr Tyr Asn
  1               5                  10                  15

Asn Tyr Ser Leu Thr Gln Pro Arg Tyr Phe Cys Lys Gly Cys Arg Arg
             20                  25                  30

Tyr Trp Thr Lys Gly Gly Ser Leu Arg Asn Val Pro Val Gly Gly Gly
         35                  40                  45

Cys Arg Lys Ser Arg Arg Pro Lys Ser Ser Ser Gly
     50                  55                  60

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer
      PAD4.18

<400> SEQUENCE: 7
tcgacaaatc tgacccaacc                                                20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer
      PAD4.19

<400> SEQUENCE: 8
gatcctatgt aatcggaatg g                                              21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer
      PAD4.4

<400> SEQUENCE: 9
gtcaaatgta ggttgatttc                                                20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: primer
```

```
          PAD4.20

<400> SEQUENCE: 10
cttcgccgag gtgtgttaaa gc                                        22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer
      PAD4.21

<400> SEQUENCE: 11
cgtggacaca attattccaa atc                                       23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer
      PAD4.22

<400> SEQUENCE: 12
gcgactcatg ttcactttaa ag                                        22

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: primer
      PAD4.23

<400> SEQUENCE: 13
caagaattgt tcgggctcc                                            19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer
      PAD4.24

<400> SEQUENCE: 14
ccaacatgta gtgtgatggt g                                         21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer
      PAD4.25

<400> SEQUENCE: 15
ggactgtctc tatttgtcta c                                         21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer
      PAD4.26
```

```
<400> SEQUENCE: 16
gggctctctc catatctctc                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer
      PAD4.16

<400> SEQUENCE: 17
gcacaaactc tcacccacac                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer
      PAD4.29

<400> SEQUENCE: 18
gcgagggtct atcttcgttc                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer
      PAD4.30

<400> SEQUENCE: 19
gcctccattt cctggtgaag                                               20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer
      PAD4.5

<400> SEQUENCE: 20
ggcccatagc caaatgatca c                                             21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer
      PAD4.31

<400> SEQUENCE: 21
ggagatagcg tggaggtgag                                               20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: primer
      PAD4.13
```

```
<400> SEQUENCE: 22
ccagcctcga ccacaacttg c                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: primer
      PAD4.33

<400> SEQUENCE: 23
ggggatcgag tcaaacgtag c                                              21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: primer
      PAD4.34

<400> SEQUENCE: 24
gtgtacccca catgagcagt aac                                            23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: primer
      PAD4.7

<400> SEQUENCE: 25
gagaatgatg ggcaatactc ac                                             22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: primer
      PAD4.11

<400> SEQUENCE: 26
ccacgacggg cattctttca ttc                                            23

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: primer
      PAD4.35

<400> SEQUENCE: 27
catatatatg aaggactttt ggtatg                                         26

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: primer
      PAD4.36

<400> SEQUENCE: 28
```
gggaatcacc ttgtgtccc                                                                    19

<210> SEQ ID NO 29
<211> LENGTH: 130
<212> TYPE: PRT
<213> ORGANISM: Fusarium heterosporum

<400> SEQUENCE: 29

```
Trp Glu Glu Val Ala Ala Asn Val Lys Ala Val Ser Ala Ala Lys
 1               5                  10                  15

Thr Ala Asn Pro Thr Phe Lys Phe Val Thr Gly His Ser Leu Gly
            20                  25                  30

Gly Ala Val Ala Thr Ile Ala Ala Tyr Leu Arg Lys Asp Gly Phe
        35                  40                  45

Pro Phe Asp Leu Tyr Thr Tyr Gly Ser Pro Arg Val Gly Asn Asp Phe
    50                  55                  60

Phe Ala Asn Phe Val Thr Gln Gln Thr Gly Ala Glu Tyr Arg Val Thr
 65                 70                  75                  80

His Gly Asp Asp Pro Val Pro Arg Leu Pro Pro Ile Val Phe Gly Tyr
                85                  90                  95

Arg His Thr Ser Pro Glu Tyr Trp Leu Asn Gly Gly Pro Leu Asp Lys
            100                 105                 110

Asp Tyr Thr Val Thr Glu Ile Lys Val Cys Glu Gly Ile Ala Asn Val
        115                 120                 125

Met Cys
    130
```

<210> SEQ ID NO 30
<211> LENGTH: 148
<212> TYPE: PRT
<213> ORGANISM: Rhizomucor miehei

<400> SEQUENCE: 30

```
Tyr Gly Glu Val Gln Asn Glu Leu Val Ala Thr Val Leu Asp Gln Phe
 1               5                  10                  15

Lys Gln Tyr Pro Ser Tyr Lys Val Ala Val Thr Gly His Ser Leu Gly
            20                  25                  30

Gly Ala Thr Ala Leu Leu Cys Ala Leu Gly Leu Tyr Gln Arg Glu Glu
        35                  40                  45

Gly Leu Ser Ser Ser Asn Leu Phe Leu Tyr Thr Gln Gly Gln Pro Arg
    50                  55                  60

Val Gly Asp Pro Ala Phe Ala Asn Tyr Val Val Ser Thr Gly Ile Pro
 65                 70                  75                  80

Tyr Arg Arg Thr Val Asn Glu Arg Asp Ile Val Pro His Leu Pro Pro
                85                  90                  95

Ala Ala Phe Gly Phe Leu His Ala Gly Glu Glu Tyr Trp Ile Thr Asp
            100                 105                 110

Asn Ser Pro Glu Thr Val Gln Val Cys Thr Ser Asp Leu Glu Thr Ser
        115                 120                 125

Asp Cys Ser Asn Ser Ile Val Pro Phe Thr Ser Val Leu Asp His Leu
    130                 135                 140

Ser Tyr Phe Gly
145
```

<210> SEQ ID NO 31
<211> LENGTH: 147

```
<212> TYPE: PRT
<213> ORGANISM: Rhizopus niveus

<400> SEQUENCE: 31

Tyr Glu Gln Val Val Asn Asp Tyr Phe Pro Val Val Gln Glu Gln Leu
 1               5                  10                  15

Thr Ala His Pro Thr Tyr Lys Val Ile Val Thr Gly His Ser Leu Gly
                20                  25                  30

Gly Ala Gln Ala Leu Leu Ala Gly Met Asp Leu Tyr Gln Arg Glu Pro
            35                  40                  45

Arg Leu Ser Pro Lys Asn Leu Ser Ile Phe Thr Val Gly Gly Pro Arg
        50                  55                  60

Val Gly Asn Pro Thr Phe Ala Tyr Tyr Val Glu Ser Thr Gly Ile Pro
65                  70                  75                  80

Phe Gln Arg Thr Val His Lys Arg Asp Ile Val Pro His Val Pro Pro
                85                  90                  95

Gln Ser Phe Gly Phe Leu His Pro Gly Val Glu Ser Trp Ile Lys Ser
            100                 105                 110

Gly Thr Ser Asn Val Gln Ile Cys Thr Ser Glu Ile Glu Thr Lys Asp
        115                 120                 125

Cys Ser Asn Ser Ile Val Pro Phe Thr Ser Ile Leu Asp His Leu Ser
130                 135                 140

Tyr Phe Asp
145

<210> SEQ ID NO 32
<211> LENGTH: 130
<212> TYPE: PRT
<213> ORGANISM: Thermomyces lanuginosus

<400> SEQUENCE: 32

Trp Arg Ser Val Ala Asp Thr Leu Arg Gln Lys Val Glu Asp Ala Val
 1               5                  10                  15

Arg Glu His Pro Asp Tyr Arg Val Val Phe Thr Gly His Ser Leu Gly
                20                  25                  30

Gly Ala Leu Ala Thr Val Ala Gly Ala Asp Leu Arg Gly Asn Gly Tyr
            35                  40                  45

Asp Ile Asp Val Phe Ser Tyr Gly Ala Pro Arg Val Gly Asn Arg Ala
        50                  55                  60

Phe Ala Glu Phe Leu Thr Val Gln Thr Gly Gly Thr Leu Tyr Arg Ile
65                  70                  75                  80

Thr His Thr Asn Asp Ile Val Pro Arg Leu Pro Pro Arg Glu Phe Gly
                85                  90                  95

Tyr Ser His Ser Ser Pro Glu Tyr Trp Ile Lys Ser Gly Thr Leu Val
            100                 105                 110

Pro Val Thr Arg Asn Asp Ile Val Lys Ile Glu Gly Ile Asp Ala Thr
        115                 120                 125

Gly Gly
    130

<210> SEQ ID NO 33
<211> LENGTH: 130
<212> TYPE: PRT
<213> ORGANISM: Aspergillus niger

<400> SEQUENCE: 33

Trp Ile Ser Val Gln Asp Gln Val Glu Ser Leu Val Lys Gln Gln Ala
```

```
              1               5              10              15
Ser Gln Tyr Pro Asp Tyr Ala Leu Thr Val Thr Gly His Ser Leu Gly
                    20                  25                  30

Ala Ser Met Ala Ala Leu Thr Ala Ala Gln Leu Ser Ala Thr Tyr Asp
            35                  40                  45

Asn Val Arg Leu Tyr Thr Phe Gly Glu Pro Arg Ser Gly Asn Gln Ala
        50                  55                  60

Phe Ala Ser Tyr Met Asn Asp Ala Phe Gln Val Ser Ser Pro Glu Thr
65                  70                  75                  80

Thr Gln Tyr Phe Arg Val Thr His Ser Asn Asp Gly Ile Pro Asn Leu
                    85                  90                  95

Pro Pro Ala Asp Glu Gly Tyr Ala His Gly Gly Val Glu Tyr Trp Ser
            100                 105                 110

Val Asp Pro Tyr Ser Ala Gln Asn Thr Phe Val Cys Thr Gly Asp Glu
        115                 120                 125

Val Gln
    130
```

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: primer for
      gl1 marker sequence

<400> SEQUENCE: 34
atattgagta ctgcctttag                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: primer for
      gl1 marker sequence

<400> SEQUENCE: 35
ccatgatccg aagagactat                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: primer for
      TOPP5 marker sequence

<400> SEQUENCE: 36
tcgacgacat cattcgtcgt                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer for
      TOPP5 marker sequence

<400> SEQUENCE: 37
gaactgaagc atcctgcagt                                              20

```
<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: primer for
      m409 marker sequence

<400> SEQUENCE: 38
cataactcgt tattgaaaaa gggc                                           24

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: primer for
      m409 marker sequence

<400> SEQUENCE: 39
cccactagat cgtcacact                                                 19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: primer for
      m457 marker sequence

<400> SEQUENCE: 40
cttcgcatca ggaaggaatt                                                20

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: primer for
      m457 marker sequence

<400> SEQUENCE: 41
gatcaactgc tatgatagct acg                                            23

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: primer for
      7A4R marker sequence

<400> SEQUENCE: 42
ccacaccggg aaagtgatgg agttcgc                                        27

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: primer for
      7A4R marker sequence

<400> SEQUENCE: 43
tgttgctgat caccggtcgg tcaggg                                         26

<210> SEQ ID NO 44
```

```
<211> LENGTH: 29
<212> TYPE: DNA
<213> ORGANISM: Artificial Sequence
<220> FEATURE:
<223> OTHER INFORMATION: Description of Artificial Sequence: primer for
      AtEM1 marker sequence

<400> SEQUENCE: 44
caggagaggt aagactcagc tccttctcg                                          29

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: primer for
      AtEM1 marker sequence

<400> SEQUENCE: 45
catctgggaa accttattat gcgttggcg                                          29

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: primer for
      1E3L marker sequence

<400> SEQUENCE: 46
tcgcctttga cccaacacag agatgtc                                            27

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: primer for
      1E3L marker sequence

<400> SEQUENCE: 47
ctgaagggaa gcgaatatcc tcattctc                                           28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: primer for
      9D9L marker sequence

<400> SEQUENCE: 48
ctcaatgtct ggcagctttc tgggatgc                                           28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: primer for
      9D9L marker sequence

<400> SEQUENCE: 49
caattccgat gtagtgacca atcggagc                                           28

<210> SEQ ID NO 50
<211> LENGTH: 21
```

```
<212> TYPE: DNA
<213> ORGANISM: Artificial Sequence
<220> FEATURE:
<223> OTHER INFORMATION: Description of Artificial Sequence: primer for
      AFC1 marker sequence

<400> SEQUENCE: 50
ggaactctca agtctaaaca g                                                     21

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: primer for
      AFC1 marker sequence

<400> SEQUENCE: 51
agctttatca cgatacacac tgc                                                   23

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: primer for
      BGL1 marker sequence

<400> SEQUENCE: 52
tcttctcggt ctattcttcg                                                       20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: primer
      for BGL1 marker sequence

<400> SEQUENCE: 53
ttatcaccat aacgtctccc                                                       20

<210> SEQ ID NO 54
<211> LENGTH: 1732
<212> TYPE: DNA
<213> ORGANISM: Arabidopsis thaliana
<220> FEATURE:
<221> NAME/KEY: CDS
<222> LOCATION: (1)..(1626)
<223> OTHER INFORMATION: nucleotide sequence of wild type PAD4 cDNA
      cloned in pCR2.1

<400> SEQUENCE: 54 atg gac gat tgt cga ttc gag acg agt gag ttg caa gct tcg gta atg         48
Met Asp Asp Cys Arg Phe Glu Thr Ser Glu Leu Gln Ala Ser Val Met
 1               5                  10                  15 ata tcg act cct tta ttt acc gat tct tgg agt tca tgc aac acc gca         96
Ile Ser Thr Pro Leu Phe Thr Asp Ser Trp Ser Ser Cys Asn Thr Ala
             20                  25                  30 aat tgc aac ggg agt ata aag atc cat gac atc gcc ggg att aca tac        144
Asn Cys Asn Gly Ser Ile Lys Ile His Asp Ile Ala Gly Ile Thr Tyr
         35                  40                  45 gtt gct ata ccg gcg gta tcg atg att cag ttg ggg aat ctt gtg ggc        192
Val Ala Ile Pro Ala Val Ser Met Ile Gln Leu Gly Asn Leu Val Gly
     50                  55                  60 ttg cca gtc acc gga gat gtt ctt ttc ccc ggc tta tcc tcc gat gaa        240
```

```
Leu Pro Val Thr Gly Asp Val Leu Phe Pro Gly Leu Ser Ser Asp Glu
 65                  70                  75                  80 cct cta cct atg gtc gac gct gcc ata ctc aaa ctc ttt ctt cag tta         288
Pro Leu Pro Met Val Asp Ala Ala Ile Leu Lys Leu Phe Leu Gln Leu
                 85                  90                  95 aag atc aag gaa gga ttg gaa ttg gaa ttg tta ggt aaa aag ctg gtg         336
Lys Ile Lys Glu Gly Leu Glu Leu Glu Leu Leu Gly Lys Lys Leu Val
            100                 105                 110 gtg ata acc ggc cat tca acc ggc ggc gca ttg gcc gct ttc acc gca         384
Val Ile Thr Gly His Ser Thr Gly Gly Ala Leu Ala Ala Phe Thr Ala
            115                 120                 125 ctt tgg ctt cta tct caa tct tct ccg ccg tca ttc cgc gtc ttt tgt         432
Leu Trp Leu Leu Ser Gln Ser Ser Pro Pro Ser Phe Arg Val Phe Cys
        130                 135                 140 atc acc ttt ggc tct cct ctg ctc gga aac caa tct ctc tcc acc tca         480
Ile Thr Phe Gly Ser Pro Leu Leu Gly Asn Gln Ser Leu Ser Thr Ser
145                 150                 155                 160 att tca cga tca cgt tta gca cac aac ttc tgc cac gtg gtc tcc atc         528
Ile Ser Arg Ser Arg Leu Ala His Asn Phe Cys His Val Val Ser Ile
                165                 170                 175 cac gac ctc gtt cct aga agc agc aat gaa caa ttc tgg ccc ttt gga         576
His Asp Leu Val Pro Arg Ser Ser Asn Glu Gln Phe Trp Pro Phe Gly
            180                 185                 190 act tac ttg ttc tgt tcc gac aaa gga ggt gtc tgt cta gac aac gct         624
Thr Tyr Leu Phe Cys Ser Asp Lys Gly Gly Val Cys Leu Asp Asn Ala
            195                 200                 205 ggt tct gtt cgt ctg atg ttt aat atc ctc aac acc aca gca act caa         672
Gly Ser Val Arg Leu Met Phe Asn Ile Leu Asn Thr Thr Ala Thr Gln
        210                 215                 220 aac acc gag gaa cat cag agg tac gga cac tat gtg ttc aca ctt tca         720
Asn Thr Glu Glu His Gln Arg Tyr Gly His Tyr Val Phe Thr Leu Ser
225                 230                 235                 240 cac atg ttt ctt aaa tct aga agc ttt ctt ggt ggg agt atc ccc gac         768
His Met Phe Leu Lys Ser Arg Ser Phe Leu Gly Gly Ser Ile Pro Asp
                245                 250                 255 aat agc tac caa gct ggt gtt gcg tta gcc gtt gaa gct cta ggt ttc         816
Asn Ser Tyr Gln Ala Gly Val Ala Leu Ala Val Glu Ala Leu Gly Phe
            260                 265                 270 tct aac gat gac aca agt ggc gtt tta gtc aaa gaa tgt ata gaa aca         864
Ser Asn Asp Asp Thr Ser Gly Val Leu Val Lys Glu Cys Ile Glu Thr
            275                 280                 285 gct aca aga att gtt cgg gct cct att ctg agg tca gct gag tta gcc         912
Ala Thr Arg Ile Val Arg Ala Pro Ile Leu Arg Ser Ala Glu Leu Ala
        290                 295                 300 aat gag ctt gct agt gtc ttg cca gca aga ctc gag att caa tgg tac         960
Asn Glu Leu Ala Ser Val Leu Pro Ala Arg Leu Glu Ile Gln Trp Tyr
305                 310                 315                 320 aaa gat cgt tgc gat gca tca gaa gag cag cta ggt tac tac gat ttc        1008
Lys Asp Arg Cys Asp Ala Ser Glu Glu Gln Leu Gly Tyr Tyr Asp Phe
                325                 330                 335 ttc aaa cga tat tcg ttg aag aga gac ttt aaa gtg aac atg agt cgc        1056
Phe Lys Arg Tyr Ser Leu Lys Arg Asp Phe Lys Val Asn Met Ser Arg
            340                 345                 350 ata aga cta gct aag ttt tgg gac aca gtg att aaa atg gtg gag acg        1104
Ile Arg Leu Ala Lys Phe Trp Asp Thr Val Ile Lys Met Val Glu Thr
            355                 360                 365 aat gag tta cct ttt gat ttt cat tta gga aag aaa tgg att tac gca        1152
Asn Glu Leu Pro Phe Asp Phe His Leu Gly Lys Lys Trp Ile Tyr Ala
        370                 375                 380
```

```
tct caa ttt tat caa ctc tta gcc gag cca ctc gac att gcg aat ttc      1200
Ser Gln Phe Tyr Gln Leu Leu Ala Glu Pro Leu Asp Ile Ala Asn Phe
385                 390                 395                 400 tac aaa aac aga gat ata aag act ggc ggg cat tac ttg gag ggg aat      1248
Tyr Lys Asn Arg Asp Ile Lys Thr Gly Gly His Tyr Leu Glu Gly Asn
                405                 410                 415 aga cct aaa agg tat gag gtg att gat aaa tgg cag aaa gga gtt aaa      1296
Arg Pro Lys Arg Tyr Glu Val Ile Asp Lys Trp Gln Lys Gly Val Lys
            420                 425                 430 gtg cct gag gag tgt gtg aga agc aga tac gcg agc aca acg caa gat      1344
Val Pro Glu Glu Cys Val Arg Ser Arg Tyr Ala Ser Thr Thr Gln Asp
        435                 440                 445 act tgc ttt tgg gct aag ctt gag caa gca aaa gag tgg ttg gat gag      1392
Thr Cys Phe Trp Ala Lys Leu Glu Gln Ala Lys Glu Trp Leu Asp Glu
    450                 455                 460 gcg aga aaa gag agt agt gat ccc cag agg aga tct ttg tta cgg gaa      1440
Ala Arg Lys Glu Ser Ser Asp Pro Gln Arg Arg Ser Leu Leu Arg Glu
465                 470                 475                 480 aag att gtt cca ttc gag agt tat gcg aat aca ttg gtg acg aag aag      1488
Lys Ile Val Pro Phe Glu Ser Tyr Ala Asn Thr Leu Val Thr Lys Lys
                485                 490                 495 gag gtt tct ttg gat gtt aaa gcg aag aac tcg agt tat agt gtg tgg      1536
Glu Val Ser Leu Asp Val Lys Ala Lys Asn Ser Ser Tyr Ser Val Trp
            500                 505                 510 gag gcg aat ctg aaa gag ttc aag tgc aaa atg ggt tat gaa aat gaa      1584
Glu Ala Asn Leu Lys Glu Phe Lys Cys Lys Met Gly Tyr Glu Asn Glu
        515                 520                 525 att gag atg gtt gtt gat gag agt gac gca atg gag act tag              1626
Ile Glu Met Val Val Asp Glu Ser Asp Ala Met Glu Thr
    530                 535                 540 taggactaat agcaaatcga atgtttgata tgctatataa caatctgtat cattgttgtt    1686
catcatgttt atgcaagact ttctgatgaa tgttactata tattct                   1732

<210> SEQ ID NO 55
<211> LENGTH: 541
<212> TYPE: PRT
<213> ORGANISM: Arabidopsis thaliana

<400> SEQUENCE: 55

Met Asp Asp Cys Arg Phe Glu Thr Ser Glu Leu Gln Ala Ser Val Met
 1               5                  10                  15

Ile Ser Thr Pro Leu Phe Thr Asp Ser Trp Ser Ser Cys Asn Thr Ala
            20                  25                  30

Asn Cys Asn Gly Ser Ile Lys Ile His Asp Ile Ala Gly Ile Thr Tyr
        35                  40                  45

Val Ala Ile Pro Ala Val Ser Met Ile Gln Leu Gly Asn Leu Val Gly
    50                  55                  60

Leu Pro Val Thr Gly Asp Val Leu Phe Pro Gly Leu Ser Ser Asp Glu
65                  70                  75                  80

Pro Leu Pro Met Val Asp Ala Ala Ile Leu Lys Leu Phe Leu Gln Leu
                85                  90                  95

Lys Ile Lys Glu Gly Leu Glu Leu Glu Leu Leu Gly Lys Lys Leu Val
            100                 105                 110

Val Ile Thr Gly His Ser Thr Gly Gly Ala Leu Ala Ala Phe Thr Ala
        115                 120                 125

Leu Trp Leu Leu Ser Gln Ser Ser Pro Pro Ser Phe Arg Val Phe Cys
    130                 135                 140
```

```
-continued

Ile Thr Phe Gly Ser Pro Leu Gly Asn Gln Ser Leu Ser Thr Ser
145                 150                 155                 160

Ile Ser Arg Ser Arg Leu Ala His Asn Phe Cys His Val Val Ser Ile
                165                 170                 175

His Asp Leu Val Pro Arg Ser Ser Asn Glu Gln Phe Trp Pro Phe Gly
            180                 185                 190

Thr Tyr Leu Phe Cys Ser Asp Lys Gly Val Cys Leu Asp Asn Ala
        195                 200                 205

Gly Ser Val Arg Leu Met Phe Asn Ile Leu Asn Thr Thr Ala Thr Gln
    210                 215                 220

Asn Thr Glu Glu His Gln Arg Tyr Gly His Tyr Val Phe Thr Leu Ser
225                 230                 235                 240

His Met Phe Leu Lys Ser Arg Ser Phe Leu Gly Gly Ser Ile Pro Asp
                245                 250                 255

Asn Ser Tyr Gln Ala Gly Val Ala Leu Ala Val Glu Ala Leu Gly Phe
            260                 265                 270

Ser Asn Asp Asp Thr Ser Gly Val Leu Val Lys Glu Cys Ile Glu Thr
        275                 280                 285

Ala Thr Arg Ile Val Arg Ala Pro Ile Leu Arg Ser Ala Glu Leu Ala
    290                 295                 300

Asn Glu Leu Ala Ser Val Leu Pro Ala Arg Leu Glu Ile Gln Trp Tyr
305                 310                 315                 320

Lys Asp Arg Cys Asp Ala Ser Glu Glu Gln Leu Gly Tyr Tyr Asp Phe
                325                 330                 335

Phe Lys Arg Tyr Ser Leu Lys Arg Asp Phe Lys Val Asn Met Ser Arg
            340                 345                 350

Ile Arg Leu Ala Lys Phe Trp Asp Thr Val Ile Lys Met Val Glu Thr
        355                 360                 365

Asn Glu Leu Pro Phe Asp Phe His Leu Gly Lys Lys Trp Ile Tyr Ala
    370                 375                 380

Ser Gln Phe Tyr Gln Leu Leu Ala Glu Pro Leu Asp Ile Ala Asn Phe
385                 390                 395                 400

Tyr Lys Asn Arg Asp Ile Lys Thr Gly Gly His Tyr Leu Glu Gly Asn
                405                 410                 415

Arg Pro Lys Arg Tyr Glu Val Ile Asp Lys Trp Gln Lys Gly Val Lys
            420                 425                 430

Val Pro Glu Glu Cys Val Arg Ser Arg Tyr Ala Ser Thr Thr Gln Asp
        435                 440                 445

Thr Cys Phe Trp Ala Lys Leu Glu Gln Ala Lys Glu Trp Leu Asp Glu
    450                 455                 460

Ala Arg Lys Glu Ser Ser Asp Pro Gln Arg Arg Ser Leu Leu Arg Glu
465                 470                 475                 480

Lys Ile Val Pro Phe Glu Ser Tyr Ala Asn Thr Leu Val Thr Lys Lys
                485                 490                 495

Glu Val Ser Leu Asp Val Lys Ala Lys Asn Ser Ser Tyr Ser Val Trp
            500                 505                 510

Glu Ala Asn Leu Lys Glu Phe Lys Cys Lys Met Gly Tyr Glu Asn Glu
        515                 520                 525

Ile Glu Met Val Val Asp Glu Ser Asp Ala Met Glu Thr
    530                 535                 540

<210> SEQ ID NO 56
<211> LENGTH: 1732
<212> TYPE: DNA
```

<213> ORGANISM: Arabidopsis thaliana
<220> FEATURE:
<221> NAME/KEY: CDS
<222> LOCATION: (1)..(1074)

<400> SEQUENCE: 56

| | | | | | | | | | | | | | | | | |
|---|---|---|---|---|---|---|---|---|---|---|---|---|---|---|---|---|
| atg | gac | gat | tgt | cga | ttc | gag | acg | agt | gag | ttg | caa | gct | tcg | gta | atg | 48 |
| Met | Asp | Asp | Cys | Arg | Phe | Glu | Thr | Ser | Glu | Leu | Gln | Ala | Ser | Val | Met | |
| 1 | | | | 5 | | | | | 10 | | | | | 15 | | |
| ata | tcg | act | cct | tta | ttt | acc | gat | tct | tgg | agt | tca | tgc | aac | acc | gca | 96 |
| Ile | Ser | Thr | Pro | Leu | Phe | Thr | Asp | Ser | Trp | Ser | Ser | Cys | Asn | Thr | Ala | |
| | | | 20 | | | | | 25 | | | | | 30 | | | |
| aat | tgc | aac | ggg | agt | ata | aag | atc | cat | gac | atc | gcc | ggg | att | aca | tac | 144 |
| Asn | Cys | Asn | Gly | Ser | Ile | Lys | Ile | His | Asp | Ile | Ala | Gly | Ile | Thr | Tyr | |
| | | 35 | | | | | 40 | | | | | 45 | | | | |
| gtt | gct | ata | ccg | gcg | gta | tcg | atg | att | cag | ttg | ggg | aat | ctt | gtg | ggc | 192 |
| Val | Ala | Ile | Pro | Ala | Val | Ser | Met | Ile | Gln | Leu | Gly | Asn | Leu | Val | Gly | |
| 50 | | | | | 55 | | | | | 60 | | | | | | |
| ttg | cca | gtc | acc | gga | gat | gtt | ctt | ttc | ccc | ggc | tta | tcc | tcc | gat | gaa | 240 |
| Leu | Pro | Val | Thr | Gly | Asp | Val | Leu | Phe | Pro | Gly | Leu | Ser | Ser | Asp | Glu | |
| 65 | | | | | 70 | | | | | 75 | | | | | 80 | |
| cct | cta | cct | atg | gtc | gac | gct | gcc | ata | ctc | aaa | ctc | ttt | ctt | cag | tta | 288 |
| Pro | Leu | Pro | Met | Val | Asp | Ala | Ala | Ile | Leu | Lys | Leu | Phe | Leu | Gln | Leu | |
| | | | | 85 | | | | | 90 | | | | | 95 | | |
| aag | atc | aag | gaa | gga | ttg | gaa | ttg | gaa | ttg | tta | ggt | aaa | aag | ctg | gtg | 336 |
| Lys | Ile | Lys | Glu | Gly | Leu | Glu | Leu | Glu | Leu | Leu | Gly | Lys | Lys | Leu | Val | |
| | | | | 100 | | | | | 105 | | | | | 110 | | |
| gtg | ata | acc | ggc | cat | tca | acc | ggc | ggc | gca | ttg | gcc | gct | ttc | acc | gca | 384 |
| Val | Ile | Thr | Gly | His | Ser | Thr | Gly | Gly | Ala | Leu | Ala | Ala | Phe | Thr | Ala | |
| | | | | 115 | | | | | 120 | | | | | 125 | | |
| ctt | tgg | ctt | cta | tct | caa | tct | tct | ccg | ccg | tca | ttc | cgc | gtc | ttt | tgt | 432 |
| Leu | Trp | Leu | Leu | Ser | Gln | Ser | Ser | Pro | Pro | Ser | Phe | Arg | Val | Phe | Cys | |
| | 130 | | | | | 135 | | | | | 140 | | | | | |
| atc | acc | ttt | ggc | tct | cct | ctg | ctc | gga | aac | caa | tct | ctc | tcc | acc | tca | 480 |
| Ile | Thr | Phe | Gly | Ser | Pro | Leu | Leu | Gly | Asn | Gln | Ser | Leu | Ser | Thr | Ser | |
| 145 | | | | | 150 | | | | | 155 | | | | | 160 | |
| att | tca | cga | tca | cgt | tta | gca | cac | aac | ttc | tgc | cac | gtg | gtc | tcc | atc | 528 |
| Ile | Ser | Arg | Ser | Arg | Leu | Ala | His | Asn | Phe | Cys | His | Val | Val | Ser | Ile | |
| | | | | 165 | | | | | 170 | | | | | 175 | | |
| cac | gac | ctc | gtt | cct | aga | agc | agc | aat | gaa | caa | ttc | tgg | ccc | ttt | gga | 576 |
| His | Asp | Leu | Val | Pro | Arg | Ser | Ser | Asn | Glu | Gln | Phe | Trp | Pro | Phe | Gly | |
| | | | | 180 | | | | | 185 | | | | | 190 | | |
| act | tac | ttg | ttc | tgt | tcc | gac | aaa | gga | ggt | gtc | tgt | cta | gac | aac | gct | 624 |
| Thr | Tyr | Leu | Phe | Cys | Ser | Asp | Lys | Gly | Gly | Val | Cys | Leu | Asp | Asn | Ala | |
| | | | 195 | | | | | 200 | | | | | 205 | | | |
| ggt | tct | gtt | cgt | ctg | atg | ttt | aat | atc | ctc | aac | acc | aca | gca | act | caa | 672 |
| Gly | Ser | Val | Arg | Leu | Met | Phe | Asn | Ile | Leu | Asn | Thr | Thr | Ala | Thr | Gln | |
| | 210 | | | | | 215 | | | | | 220 | | | | | |
| aac | acc | gag | gaa | cat | cag | agg | tac | gga | cac | tat | gtg | ttc | aca | ctt | tca | 720 |
| Asn | Thr | Glu | Glu | His | Gln | Arg | Tyr | Gly | His | Tyr | Val | Phe | Thr | Leu | Ser | |
| 225 | | | | | 230 | | | | | 235 | | | | | 240 | |
| cac | atg | ttt | ctt | aaa | tct | aga | agc | ttt | ctt | ggt | ggg | agt | atc | ccc | gac | 768 |
| His | Met | Phe | Leu | Lys | Ser | Arg | Ser | Phe | Leu | Gly | Gly | Ser | Ile | Pro | Asp | |
| | | | | 245 | | | | | 250 | | | | | 255 | | |
| aat | agc | tac | caa | gct | ggt | gtt | gcg | tta | gcc | gtt | gaa | gct | cta | ggt | ttc | 816 |
| Asn | Ser | Tyr | Gln | Ala | Gly | Val | Ala | Leu | Ala | Val | Glu | Ala | Leu | Gly | Phe | |
| | | | 260 | | | | | 265 | | | | | 270 | | | |
| tct | aac | gat | gac | aca | agt | ggc | gtt | tta | gtc | aaa | gaa | tgt | ata | gaa | aca | 864 |
| Ser | Asn | Asp | Asp | Thr | Ser | Gly | Val | Leu | Val | Lys | Glu | Cys | Ile | Glu | Thr | |
| | | | 275 | | | | | 280 | | | | | 285 | | | |

-continued

```
gct aca aga att gtt cgg gct cct att ctg agg tca gct gag tta gcc    912
Ala Thr Arg Ile Val Arg Ala Pro Ile Leu Arg Ser Ala Glu Leu Ala
    290                 295                 300 aat gag ctt gct agt gtc ttg cca gca aga ctc gag att caa tgg tac    960
Asn Glu Leu Ala Ser Val Leu Pro Ala Arg Leu Glu Ile Gln Trp Tyr
305                 310                 315                 320 aaa gat cgt tgc gat gca tca gaa gag cag cta ggt tac tac gat ttc   1008
Lys Asp Arg Cys Asp Ala Ser Glu Glu Gln Leu Gly Tyr Tyr Asp Phe
                325                 330                 335 ttc aaa cga tat tcg ttg aag aga gac ttt aaa gtg aac atg agt cgc   1056
Phe Lys Arg Tyr Ser Leu Lys Arg Asp Phe Lys Val Asn Met Ser Arg
            340                 345                 350 ata aga cta gct aag ttt tag gacacagtga ttaaaatggt ggagacgaat      1107
Ile Arg Leu Ala Lys Phe
                355 gagttacctt tgattttca tttaggaaag aaatggattt acgcatctca attttatcaa  1167 ctcttagccg agccactcga cattgcgaat ttctacaaaa acagagatat aaagactggc  1227 gggcattact tggagggaa tagacctaaa aggtatgagg tgattgataa atggcagaaa   1287 ggagttaaag tgcctgagga gtgtgtgaga agcagatacg cgagcacaac gcaagatact  1347 tgcttttggg ctaagcttga gcaagcaaaa gagtggttgg atgaggcgag aaaagagagt  1407 agtgatcccc agaggagatc tttgttacgg gaaaagattg ttccattcga gagttatgcg  1467 aatacattgg tgacgaagaa ggaggtttct ttggatgtta aagcgaagaa ctcgagttat  1527 agtgtgtggg aggcgaatct gaaagagttc aagtgcaaaa tgggttatga aaatgaaatt  1587 gagatggttg ttgatgagag tgacgcaatg gagacttagt aggactaata gcaaatcgaa  1647 tgtttgatat gctatataac aatctgtatc attgttgttc atcatgttta tgcaagactt  1707 tctgatg aatgttacta tatattct                                       1732
```

<210> SEQ ID NO 57
<211> LENGTH: 358
<212> TYPE: PRT
<213> ORGANISM: Arabidopsis thaliana

<400> SEQUENCE: 57

```
Met Asp Asp Cys Arg Phe Glu Thr Ser Glu Leu Gln Ala Ser Val Met
1               5                   10                  15

Ile Ser Thr Pro Leu Phe Thr Asp Ser Trp Ser Ser Cys Asn Thr Ala
            20                  25                  30

Asn Cys Asn Gly Ser Ile Lys Ile His Asp Ile Ala Gly Ile Thr Tyr
        35                  40                  45

Val Ala Ile Pro Ala Val Ser Met Ile Gln Leu Gly Asn Leu Val Gly
    50                  55                  60

Leu Pro Val Thr Gly Asp Val Leu Phe Pro Gly Leu Ser Ser Asp Glu
65                  70                  75                  80

Pro Leu Pro Met Val Asp Ala Ala Ile Leu Lys Leu Phe Leu Gln Leu
                85                  90                  95

Lys Ile Lys Glu Gly Leu Glu Leu Leu Leu Gly Lys Lys Leu Val
            100                 105                 110

Val Ile Thr Gly His Ser Thr Gly Gly Ala Leu Ala Ala Phe Thr Ala
        115                 120                 125

Leu Trp Leu Leu Ser Gln Ser Pro Pro Ser Phe Arg Val Phe Cys
    130                 135                 140

Ile Thr Phe Gly Ser Pro Leu Leu Gly Asn Gln Ser Leu Ser Thr Ser
145                 150                 155                 160
```

-continued

```
Ile Ser Arg Ser Arg Leu Ala His Asn Phe Cys His Val Val Ser Ile
            165                 170                 175
His Asp Leu Val Pro Arg Ser Ser Asn Glu Gln Phe Trp Pro Phe Gly
            180                 185                 190
Thr Tyr Leu Phe Cys Ser Asp Lys Gly Val Cys Leu Asp Asn Ala
            195                 200                 205
Gly Ser Val Arg Leu Met Phe Asn Ile Leu Asn Thr Thr Ala Thr Gln
            210                 215                 220
Asn Thr Glu Glu His Gln Arg Tyr Gly His Tyr Val Phe Thr Leu Ser
225                 230                 235                 240
His Met Phe Leu Lys Ser Arg Ser Phe Leu Gly Gly Ser Ile Pro Asp
            245                 250                 255
Asn Ser Tyr Gln Ala Gly Val Ala Leu Ala Val Glu Ala Leu Gly Phe
            260                 265                 270
Ser Asn Asp Asp Thr Ser Gly Val Leu Val Lys Glu Cys Ile Glu Thr
            275                 280                 285
Ala Thr Arg Ile Val Arg Ala Pro Ile Leu Arg Ser Ala Glu Leu Ala
            290                 295                 300
Asn Glu Leu Ala Ser Val Leu Pro Ala Arg Leu Glu Ile Gln Trp Tyr
305                 310                 315                 320
Lys Asp Arg Cys Asp Ala Ser Glu Glu Gln Leu Gly Tyr Tyr Asp Phe
            325                 330                 335
Phe Lys Arg Tyr Ser Leu Lys Arg Asp Phe Lys Val Asn Met Ser Arg
            340                 345                 350
Ile Arg Leu Ala Lys Phe
            355
```

<210> SEQ ID NO 58
<211> LENGTH: 1733
<212> TYPE: DNA
<213> ORGANISM: Arabidopsis thaliana
<220> FEATURE:
<221> NAME/KEY: CDS
<222> LOCATION: (1)..(546)

<400> SEQUENCE: 58

```
atg gac gat tgt cga ttc gag acg agt gag ttg caa gct tcg gta atg      48
Met Asp Asp Cys Arg Phe Glu Thr Ser Glu Leu Gln Ala Ser Val Met
 1               5                  10                  15 ata tcg act cct tta ttt acc gat tct tgg agt tca tgc aac acc gca      96
Ile Ser Thr Pro Leu Phe Thr Asp Ser Trp Ser Ser Cys Asn Thr Ala
                20                  25                  30 aat tgc aac ggg agt ata aag atc cat gac atc gcc ggg att aca tac     144
Asn Cys Asn Gly Ser Ile Lys Ile His Asp Ile Ala Gly Ile Thr Tyr
            35                  40                  45 gtt gct ata ccg gcg gta tcg atg att cag ttg ggg aat ctt gtg ggc     192
Val Ala Ile Pro Ala Val Ser Met Ile Gln Leu Gly Asn Leu Val Gly
     50                  55                  60 ttg cca gtc acc gga gat gtt ctt ttc ccc ggc tta tcc tcc gat gaa     240
Leu Pro Val Thr Gly Asp Val Leu Phe Pro Gly Leu Ser Ser Asp Glu
65                  70                  75                  80 cct cta cct atg gtc gac gct gcc ata ctc aaa ctc ttt ctt cag tta     288
Pro Leu Pro Met Val Asp Ala Ala Ile Leu Lys Leu Phe Leu Gln Leu
                85                  90                  95 aag atc aag gaa gga ttg gaa ttg gaa ttg tta ggt aaa aag ctg gtg     336
Lys Ile Lys Glu Gly Leu Glu Leu Glu Leu Leu Gly Lys Lys Leu Val
                100                 105                 110
```

```
gtg ata acc ggc cat tca acc ggc ggc gca ttg gcc gct ttc acc gca      384
Val Ile Thr Gly His Ser Thr Gly Gly Ala Leu Ala Ala Phe Thr Ala
        115                 120                 125 ctt tgg ctt cta tct caa tct tct ccg ccg tca ttc cgc gtc ttt ttg      432
Leu Trp Leu Leu Ser Gln Ser Ser Pro Pro Ser Phe Arg Val Phe Leu
130                 135                 140 tat cac ctt tgg ctc tcc tct gct cgg aaa cca atc tct ctc cac ctc      480
Tyr His Leu Trp Leu Ser Ser Ala Arg Lys Pro Ile Ser Leu His Leu
145                 150                 155                 160 aat ttc acg atc acg ttt agc aca caa ctt ctg cca cgt ggt ctc cat      528
Asn Phe Thr Ile Thr Phe Ser Thr Gln Leu Leu Pro Arg Gly Leu His
                165                 170                 175 cca cga cct cgt tcc tag aagcagcaat gaacaattct ggccctttgg             576
Pro Arg Pro Arg Ser
            180 aacttacttg ttctgttccg acaaaggagg tgtctgtcta gacaacgctg gttctgttcg    636 tctgatgttt aatatcctca acaccacagc aactcaaaac accgaggaac atcagaggta    696 cggacactat gtgttcacac tttcacacat gtttcttaaa tctagaagct ttcttggtgg    756 gagtatcccc gacaatagct accaagctgg tgttgcgtta gccgttgaag ctctaggttt    816 ctctaacgat gacacaagtg gcgtttagt caaagaatgt atagaaacag ctacaagaat     876 tgttcgggct cctattctga ggtcagctga gttagccaat gagcttgcta gtgtcttgcc    936 agcaagactc gagattcaat ggtacaaaga tcgttgcgat gcatcagaag agcagctagg    996 ttactacgat ttcttcaaac gatattcgtt gaagagagac tttaaagtga acatgagtcg   1056 cataagacta gctaagtttt gggacacagt gattaaaatg gtggagacga atgagttacc   1116 ttttgatttt catttaggaa agaaatggat ttacgcatct caattttatc aactcttagc   1176 cgagccactc gacattgcga atttctacaa aaacagagat ataaagactg gcgggcatta   1236 cttggagggg aatagaccta aaggtatga ggtgattgat aaatggcaga aaggagttaa    1296 agtgcctgag gagtgtgtga gaagcagata cgcgagcaca acgcaagata cttgcttttg   1356 ggctaagctt gagcaagcaa aagagtggtt ggatgaggcg agaaaagaga gtagtgatcc   1416 ccagaggaga tctttgttac gggaaaagat tgttccattc gagagttatg cgaatacatt   1476 ggtgacgaag aaggaggttt ctttggatgt taaagcgaag aactcgagtt atagtgtgtg   1536 ggaggcgaat ctgaaagagt tcaagtgcaa atgggttat gaaaatgaaa ttgagatggt    1596 tgttgatgag agtgacgcaa tggagactta gtaggactaa tagcaaatcg aatgtttgat   1656 atgctatata acaatctgta tcattgttgt tcatcatgtt tatgcaagac tttctgatga   1716 atgttactat atattct                                                  1733
```

<210> SEQ ID NO 59
<211> LENGTH: 181
<212> TYPE: PRT
<213> ORGANISM: Arabidopsis thaliana

<400> SEQUENCE: 59

Met Asp Asp Cys Arg Phe Glu Thr Ser Glu Leu Gln Ala Ser Val Met
1               5                   10                  15

Ile Ser Thr Pro Leu Phe Thr Asp Ser Trp Ser Ser Cys Asn Thr Ala
            20                  25                  30

Asn Cys Asn Gly Ser Ile Lys Ile His Asp Ile Ala Gly Ile Thr Tyr
        35                  40                  45

Val Ala Ile Pro Ala Val Ser Met Ile Gln Leu Gly Asn Leu Val Gly
    50                  55                  60

```
Leu Pro Val Thr Gly Asp Val Leu Phe Pro Gly Leu Ser Ser Asp Glu
 65                  70                  75                  80

Pro Leu Pro Met Val Asp Ala Ala Ile Leu Lys Leu Phe Leu Gln Leu
             85                  90                  95

Lys Ile Lys Glu Gly Leu Glu Leu Glu Leu Leu Gly Lys Lys Leu Val
            100                 105                 110

Val Ile Thr Gly His Ser Thr Gly Gly Ala Leu Ala Ala Phe Thr Ala
            115                 120                 125

Leu Trp Leu Leu Ser Gln Ser Ser Pro Pro Ser Phe Arg Val Phe Leu
        130                 135                 140

Tyr His Leu Trp Leu Ser Ser Ala Arg Lys Pro Ile Ser Leu His Leu
145                 150                 155                 160

Asn Phe Thr Ile Thr Phe Ser Thr Gln Leu Leu Pro Arg Gly Leu His
                165                 170                 175

Pro Arg Pro Arg Ser
            180

<210> SEQ ID NO 60
<211> LENGTH: 1732
<212> TYPE: DNA
<213> ORGANISM: Arabidopsis thaliana
<220> FEATURE:
<221> NAME/KEY: CDS
<222> LOCATION: (1)..(1158)

<400> SEQUENCE: 60 atg gac gat tgt cga ttc gag acg agt gag ttg caa gct tcg gta atg      48
Met Asp Asp Cys Arg Phe Glu Thr Ser Glu Leu Gln Ala Ser Val Met
  1               5                  10                  15 ata tcg act cct tta ttt acc gat tct tgg agt tca tgc aac acc gca      96
Ile Ser Thr Pro Leu Phe Thr Asp Ser Trp Ser Ser Cys Asn Thr Ala
             20                  25                  30 aat tgc aac ggg agt ata aag atc cat gac atc gcc ggg att aca tac     144
Asn Cys Asn Gly Ser Ile Lys Ile His Asp Ile Ala Gly Ile Thr Tyr
         35                  40                  45 gtt gct ata ccg gcg gta tcg atg att cag ttg ggg aat ctt gtg ggc     192
Val Ala Ile Pro Ala Val Ser Met Ile Gln Leu Gly Asn Leu Val Gly
     50                  55                  60 ttg cca gtc acc gga gat gtt ctt ttc ccc ggc tta tcc tcc gat gaa     240
Leu Pro Val Thr Gly Asp Val Leu Phe Pro Gly Leu Ser Ser Asp Glu
 65                  70                  75                  80 cct cta cct atg gtc gac gct gcc ata ctc aaa ctc ttt ctt cag tta     288
Pro Leu Pro Met Val Asp Ala Ala Ile Leu Lys Leu Phe Leu Gln Leu
             85                  90                  95 aag atc aag gaa gga ttg gaa ttg gaa ttg tta ggt aaa aag ctg gtg     336
Lys Ile Lys Glu Gly Leu Glu Leu Glu Leu Leu Gly Lys Lys Leu Val
            100                 105                 110 gtg ata acc ggc cat tca acc ggc ggc gca ttg gcc gct ttc acc gca     384
Val Ile Thr Gly His Ser Thr Gly Gly Ala Leu Ala Ala Phe Thr Ala
            115                 120                 125 ctt tgg ctt cta tct caa tct tct ccg ccg tca ttc cgc gtc ttt tgt     432
Leu Trp Leu Leu Ser Gln Ser Ser Pro Pro Ser Phe Arg Val Phe Cys
        130                 135                 140 atc acc ttt ggc tct cct ctg ctc gga aac caa tct ctc tcc acc tca     480
Ile Thr Phe Gly Ser Pro Leu Leu Gly Asn Gln Ser Leu Ser Thr Ser
145                 150                 155                 160 att tca cga tca cgt tta gca cac aac ttc tgc cac gtg gtc tcc atc     528
Ile Ser Arg Ser Arg Leu Ala His Asn Phe Cys His Val Val Ser Ile
                165                 170                 175
```

```
cac gac ctc gtt cct aga agc agc aat gaa caa ttc tgg ccc ttt gga     576
His Asp Leu Val Pro Arg Ser Ser Asn Glu Gln Phe Trp Pro Phe Gly
            180                 185                 190 act tac ttg ttc tgt tcc gac aaa gga ggt gtc tgt cta gac aac gct     624
Thr Tyr Leu Phe Cys Ser Asp Lys Gly Gly Val Cys Leu Asp Asn Ala
            195                 200                 205 ggt tct gtt cgt ctg atg ttt aat atc ctc aac acc aca gca act caa     672
Gly Ser Val Arg Leu Met Phe Asn Ile Leu Asn Thr Thr Ala Thr Gln
    210                 215                 220 aac acc gag gaa cat cag agg tac gga cac tat gtg ttc aca ctt tca     720
Asn Thr Glu Glu His Gln Arg Tyr Gly His Tyr Val Phe Thr Leu Ser
225                 230                 235                 240 cac atg ttt ctt aaa tct aga agc ttt ctt ggt ggg agt atc ccc gac     768
His Met Phe Leu Lys Ser Arg Ser Phe Leu Gly Gly Ser Ile Pro Asp
                245                 250                 255 aat agc tac caa gct ggt gtt gcg tta gcc gtt gaa gct cta ggt ttc     816
Asn Ser Tyr Gln Ala Gly Val Ala Leu Ala Val Glu Ala Leu Gly Phe
            260                 265                 270 tct aac gat gac aca agt ggc gtt tta gtc aaa gaa tgt ata gaa aca     864
Ser Asn Asp Asp Thr Ser Gly Val Leu Val Lys Glu Cys Ile Glu Thr
            275                 280                 285 gct aca aga att gtt cgg gct cct att ctg agg tca gct gag tta gcc     912
Ala Thr Arg Ile Val Arg Ala Pro Ile Leu Arg Ser Ala Glu Leu Ala
    290                 295                 300 aat gag ctt gct agt gtc ttg cca gca aga ctc gag att caa tgg tac     960
Asn Glu Leu Ala Ser Val Leu Pro Ala Arg Leu Glu Ile Gln Trp Tyr
305                 310                 315                 320 aaa gat cgt tgc gat gca tca gaa gag cag cta ggt tac tac gat ttc    1008
Lys Asp Arg Cys Asp Ala Ser Glu Glu Gln Leu Gly Tyr Tyr Asp Phe
                325                 330                 335 ttc aaa cga tat tcg ttg aag aga gac ttt aaa gtg aac atg agt cgc    1056
Phe Lys Arg Tyr Ser Leu Lys Arg Asp Phe Lys Val Asn Met Ser Arg
            340                 345                 350 ata aga cta gct aag ttt tgg gac aca gtg att aaa atg gtg gag acg    1104
Ile Arg Leu Ala Lys Phe Trp Asp Thr Val Ile Lys Met Val Glu Thr
            355                 360                 365 aat gag tta cct ttt gat ttt cat tta gga aag aaa tgg att tac gca    1152
Asn Glu Leu Pro Phe Asp Phe His Leu Gly Lys Lys Trp Ile Tyr Ala
    370                 375                 380 tct taa ttttatcaac tcttagccga gccactcgac attgcgaatt tctacaaaaa     1208
Ser
385 cagagatata aagactggcg ggcattactt ggaggggaat agacctaaaa ggtatgaggt     1268 gattgataaa tggcagaaag gagttaaagt gcctgaggag tgtgtgagaa gcagatacgc     1328 gagcacaacg caagatactt gcttttgggc taagcttgag caagcaaaag agtggttgga     1388 tgaggcgaga aaagagagta gtgatccccca gaggagatct tgttacggg aaaagattgt     1448 tccattcgag agttatgcga atacattggt gacgaagaag gaggtttctt ggatgttaa     1508 agcgaagaac tcgagttata gtgtgtggga ggcgaatctg aaagagttca gtgcaaaat     1568 gggttatgaa aatgaaattg agatggttgt tgatgagagt gacgcaatgg agacttagta     1628 ggactaatag caaatcgaat gtttgatatg ctatataaca atctgtatca ttgttgttca     1688 tcatgtttat gcaagacttt ctgatgaatg ttactatata ttct                     1732

<210> SEQ ID NO 61
<211> LENGTH: 385
<212> TYPE: PRT
```

-continued

<213> ORGANISM: Arabidopsis thaliana

<400> SEQUENCE: 61

Met Asp Asp Cys Arg Phe Glu Thr Ser Glu Leu Gln Ala Ser Val Met
1               5                   10                  15

Ile Ser Thr Pro Leu Phe Thr Asp Ser Trp Ser Ser Cys Asn Thr Ala
            20                  25                  30

Asn Cys Asn Gly Ser Ile Lys Ile His Asp Ile Ala Gly Ile Thr Tyr
        35                  40                  45

Val Ala Ile Pro Ala Val Ser Met Ile Gln Leu Gly Asn Leu Val Gly
    50                  55                  60

Leu Pro Val Thr Gly Asp Val Leu Phe Pro Gly Leu Ser Ser Asp Glu
65                  70                  75                  80

Pro Leu Pro Met Val Asp Ala Ala Ile Leu Lys Leu Phe Leu Gln Leu
                85                  90                  95

Lys Ile Lys Glu Gly Leu Glu Leu Glu Leu Leu Gly Lys Lys Leu Val
            100                 105                 110

Val Ile Thr Gly His Ser Thr Gly Gly Ala Leu Ala Ala Phe Thr Ala
        115                 120                 125

Leu Trp Leu Leu Ser Gln Ser Ser Pro Pro Ser Phe Arg Val Phe Cys
130                 135                 140

Ile Thr Phe Gly Ser Pro Leu Leu Gly Asn Gln Ser Leu Ser Thr Ser
145                 150                 155                 160

Ile Ser Arg Ser Arg Leu Ala His Asn Phe Cys His Val Val Ser Ile
                165                 170                 175

His Asp Leu Val Pro Arg Ser Ser Asn Glu Gln Phe Trp Pro Phe Gly
            180                 185                 190

Thr Tyr Leu Phe Cys Ser Asp Lys Gly Gly Val Cys Leu Asp Asn Ala
        195                 200                 205

Gly Ser Val Arg Leu Met Phe Asn Ile Leu Asn Thr Thr Ala Thr Gln
    210                 215                 220

Asn Thr Glu Glu His Gln Arg Tyr Gly His Tyr Val Phe Thr Leu Ser
225                 230                 235                 240

His Met Phe Leu Lys Ser Arg Ser Phe Leu Gly Gly Ser Ile Pro Asp
                245                 250                 255

Asn Ser Tyr Gln Ala Gly Val Ala Leu Ala Val Glu Ala Leu Gly Phe
            260                 265                 270

Ser Asn Asp Asp Thr Ser Gly Val Leu Val Lys Glu Cys Ile Glu Thr
        275                 280                 285

Ala Thr Arg Ile Val Arg Ala Pro Ile Leu Arg Ser Ala Glu Leu Ala
    290                 295                 300

Asn Glu Leu Ala Ser Val Leu Pro Ala Arg Leu Glu Ile Gln Trp Tyr
305                 310                 315                 320

Lys Asp Arg Cys Asp Ala Ser Glu Glu Gln Leu Gly Tyr Tyr Asp Phe
                325                 330                 335

Phe Lys Arg Tyr Ser Leu Lys Arg Asp Phe Lys Val Asn Met Ser Arg
            340                 345                 350

Ile Arg Leu Ala Lys Phe Trp Asp Thr Val Ile Lys Met Val Glu Thr
        355                 360                 365

Asn Glu Leu Pro Phe Asp Phe His Leu Gly Lys Lys Trp Ile Tyr Ala
    370                 375                 380

Ser
385

<210> SEQ ID NO 62
<211> LENGTH: 1731
<212> TYPE: DNA
<213> ORGANISM: Arabidopsis thaliana
<220> FEATURE:
<221> NAME/KEY: CDS
<222> LOCATION: (1)..(1548)

<400> SEQUENCE: 62

| | | | | | | | | | | | | | | | | |
|---|---|---|---|---|---|---|---|---|---|---|---|---|---|---|---|---|
| atg | gac | gat | tgt | cga | ttc | gag | acg | agt | gag | ttg | caa | gct | tcg | gta | atg | 48 |
| Met | Asp | Asp | Cys | Arg | Phe | Glu | Thr | Ser | Glu | Leu | Gln | Ala | Ser | Val | Met | |
| 1 | | | | 5 | | | | | 10 | | | | | 15 | | |
| ata | tcg | act | cct | tta | ttt | acc | gat | tct | tgg | agt | tca | tgc | aac | acc | gca | 96 |
| Ile | Ser | Thr | Pro | Leu | Phe | Thr | Asp | Ser | Trp | Ser | Ser | Cys | Asn | Thr | Ala | |
| | | | 20 | | | | | 25 | | | | | 30 | | | |
| aat | tgc | aac | ggg | agt | ata | aag | atc | cat | gac | atc | gcc | ggg | att | aca | tac | 144 |
| Asn | Cys | Asn | Gly | Ser | Ile | Lys | Ile | His | Asp | Ile | Ala | Gly | Ile | Thr | Tyr | |
| | | 35 | | | | | 40 | | | | | 45 | | | | |
| gtt | gct | ata | ccg | gcg | gta | tcg | atg | att | cag | ttg | ggg | aat | ctt | gtg | ggc | 192 |
| Val | Ala | Ile | Pro | Ala | Val | Ser | Met | Ile | Gln | Leu | Gly | Asn | Leu | Val | Gly | |
| | 50 | | | | | 55 | | | | | 60 | | | | | |
| ttg | cca | gtc | acc | gga | gat | gtt | ctt | ttc | ccc | ggc | tta | tcc | tcc | gat | gaa | 240 |
| Leu | Pro | Val | Thr | Gly | Asp | Val | Leu | Phe | Pro | Gly | Leu | Ser | Ser | Asp | Glu | |
| 65 | | | | | 70 | | | | | 75 | | | | | 80 | |
| cct | cta | cct | atg | gtc | gac | gct | gcc | ata | ctc | aaa | ctc | ttt | ctt | cag | tta | 288 |
| Pro | Leu | Pro | Met | Val | Asp | Ala | Ala | Ile | Leu | Lys | Leu | Phe | Leu | Gln | Leu | |
| | | | | 85 | | | | | 90 | | | | | 95 | | |
| aag | atc | aag | gaa | gga | ttg | gaa | ttg | gaa | ttg | tta | ggt | aaa | aag | ctg | gtg | 336 |
| Lys | Ile | Lys | Glu | Gly | Leu | Glu | Leu | Glu | Leu | Leu | Gly | Lys | Lys | Leu | Val | |
| | | | | 100 | | | | | 105 | | | | | 110 | | |
| gtg | ata | acc | ggc | cat | tca | acc | ggc | ggc | gca | ttg | gcc | gct | ttc | acc | gca | 384 |
| Val | Ile | Thr | Gly | His | Ser | Thr | Gly | Gly | Ala | Leu | Ala | Ala | Phe | Thr | Ala | |
| | | | 115 | | | | | 120 | | | | | 125 | | | |
| ctt | tgg | ctt | cta | tct | caa | tct | tct | ccg | ccg | tca | ttc | cgc | gtc | ttt | tgt | 432 |
| Leu | Trp | Leu | Leu | Ser | Gln | Ser | Ser | Pro | Pro | Ser | Phe | Arg | Val | Phe | Cys | |
| | | 130 | | | | | 135 | | | | | 140 | | | | |
| atc | acc | ttt | ggc | tct | cct | ctg | ctc | gga | aac | caa | tct | ctc | tcc | acc | tca | 480 |
| Ile | Thr | Phe | Gly | Ser | Pro | Leu | Leu | Gly | Asn | Gln | Ser | Leu | Ser | Thr | Ser | |
| 145 | | | | | 150 | | | | | 155 | | | | | 160 | |
| att | tca | cga | tca | cgt | tta | gca | cac | aac | ttc | tgc | cac | gtg | gtc | tcc | atc | 528 |
| Ile | Ser | Arg | Ser | Arg | Leu | Ala | His | Asn | Phe | Cys | His | Val | Val | Ser | Ile | |
| | | | | 165 | | | | | 170 | | | | | 175 | | |
| cac | gac | ctc | gtt | cct | aga | agc | agc | aat | gaa | caa | ttc | tgg | ccc | ttt | gga | 576 |
| His | Asp | Leu | Val | Pro | Arg | Ser | Ser | Asn | Glu | Gln | Phe | Trp | Pro | Phe | Gly | |
| | | | 180 | | | | | 185 | | | | | 190 | | | |
| act | tac | ttg | ttc | tgt | tcc | gac | aaa | gga | ggt | gtc | tgt | cta | gac | aac | gct | 624 |
| Thr | Tyr | Leu | Phe | Cys | Ser | Asp | Lys | Gly | Gly | Val | Cys | Leu | Asp | Asn | Ala | |
| | | 195 | | | | | 200 | | | | | 205 | | | | |
| ggt | tct | gtt | cgt | ctg | atg | ttt | aat | atc | ctc | aac | acc | aca | gca | act | caa | 672 |
| Gly | Ser | Val | Arg | Leu | Met | Phe | Asn | Ile | Leu | Asn | Thr | Thr | Ala | Thr | Gln | |
| | 210 | | | | | 215 | | | | | 220 | | | | | |
| aac | acc | gag | gaa | cat | cag | agg | tac | gga | cac | tat | gtg | ttc | aca | ctt | tca | 720 |
| Asn | Thr | Glu | Glu | His | Gln | Arg | Tyr | Gly | His | Tyr | Val | Phe | Thr | Leu | Ser | |
| 225 | | | | | 230 | | | | | 235 | | | | | 240 | |
| cac | atg | ttt | ctt | aaa | tct | aga | agc | ttt | ctt | ggt | ggg | agt | atc | ccc | gac | 768 |
| His | Met | Phe | Leu | Lys | Ser | Arg | Ser | Phe | Leu | Gly | Gly | Ser | Ile | Pro | Asp | |
| | | | | 245 | | | | | 250 | | | | | 255 | | |
| aat | agc | tac | caa | gct | ggt | gtt | gcg | tta | gcc | gtt | gaa | gct | cta | ggt | ttc | 816 |
| Asn | Ser | Tyr | Gln | Ala | Gly | Val | Ala | Leu | Ala | Val | Glu | Ala | Leu | Gly | Phe | |
| | | | | 260 | | | | | 265 | | | | | 270 | | |

| | | |
|---|---|---|
| tct aac gat gac aca agt ggc gtt tta gtc aaa gaa tgt ata gaa aca<br>Ser Asn Asp Asp Thr Ser Gly Val Leu Val Lys Glu Cys Ile Glu Thr<br>275 280 285 | | 864 |
| gct aca aga att gtt cgg gct cct att ctg agg tca gct gag tta gcc<br>Ala Thr Arg Ile Val Arg Ala Pro Ile Leu Arg Ser Ala Glu Leu Ala<br>290 295 300 | | 912 |
| aat gag ctt gct agt gtc ttg cca gca aga ctc gag att caa tgg tac<br>Asn Glu Leu Ala Ser Val Leu Pro Ala Arg Leu Glu Ile Gln Trp Tyr<br>305 310 315 320 | | 960 |
| aaa gat cgt tgc gat gca tca gaa gag cag cta ggt tac tac gat ttc<br>Lys Asp Arg Cys Asp Ala Ser Glu Glu Gln Leu Gly Tyr Tyr Asp Phe<br>325 330 335 | | 1008 |
| ttc aaa cga tat tcg ttg aag aga gac ttt aaa gtg aac atg agt cgc<br>Phe Lys Arg Tyr Ser Leu Lys Arg Asp Phe Lys Val Asn Met Ser Arg<br>340 345 350 | | 1056 |
| ata aga cta gct aag ttt tgg gac aca gtg att aaa atg gtg gag acg<br>Ile Arg Leu Ala Lys Phe Trp Asp Thr Val Ile Lys Met Val Glu Thr<br>355 360 365 | | 1104 |
| aat gag tta cct ttt gat ttt cat tta gga aag aaa tgg att tac gca<br>Asn Glu Leu Pro Phe Asp Phe His Leu Gly Lys Lys Trp Ile Tyr Ala<br>370 375 380 | | 1152 |
| tct caa ttt tat caa ctc tta gcc gag cca ctc gac att gcg aat ttc<br>Ser Gln Phe Tyr Gln Leu Leu Ala Glu Pro Leu Asp Ile Ala Asn Phe<br>385 390 395 400 | | 1200 |
| tac aaa aac aga gat ata aag act ggc ggg cat tac ttg gag ggg aat<br>Tyr Lys Asn Arg Asp Ile Lys Thr Gly Gly His Tyr Leu Glu Gly Asn<br>405 410 415 | | 1248 |
| aga cct aaa agg tat gag gtg att gat aaa tgg cag aaa gga gtt aaa<br>Arg Pro Lys Arg Tyr Glu Val Ile Asp Lys Trp Gln Lys Gly Val Lys<br>420 425 430 | | 1296 |
| gtg cct gag gag tgt gtg aga agc aga tac gcg agc aca acg caa gat<br>Val Pro Glu Glu Cys Val Arg Ser Arg Tyr Ala Ser Thr Thr Gln Asp<br>435 440 445 | | 1344 |
| act tgc ttt tgg gct aag ctt gag caa gca aaa gag tgg ttg gat gag<br>Thr Cys Phe Trp Ala Lys Leu Glu Gln Ala Lys Glu Trp Leu Asp Glu<br>450 455 460 | | 1392 |
| gcg aga aaa gag agt agt gat ccc cag agg aga tct ttg tta cgg gaa<br>Ala Arg Lys Glu Ser Ser Asp Pro Gln Arg Arg Ser Leu Leu Arg Glu<br>465 470 475 480 | | 1440 |
| aag att gtt cca ttc gag agt tat gcg aat aca ttg gtg acg aag aag<br>Lys Ile Val Pro Phe Glu Ser Tyr Ala Asn Thr Leu Val Thr Lys Lys<br>485 490 495 | | 1488 |
| gag gtt tct ttg gat gtt aaa gcg aag aac tcg agt tat agt gtg tgg<br>Glu Val Ser Leu Asp Val Lys Ala Lys Asn Ser Ser Tyr Ser Val Trp<br>500 505 510 | | 1536 |
| agg cga atc tga aagagttcaa gtgcaaaatg ggttatgaaa atgaaattga<br>Arg Arg Ile<br>515 | | 1588 |
| gatggttgtt gatgagagtg acgcaatgga gacttagtag gactaatagc aaatcgaatg | | 1648 |
| tttgatatgc tatataacaa tctgtatcat tgttgttcat catgtttatg caagactttc | | 1708 |
| tgatgaatgt tactatatat tct | | 1731 |

<210> SEQ ID NO 63
<211> LENGTH: 515
<212> TYPE: PRT
<213> ORGANISM: Arabidopsis thaliana

<400> SEQUENCE: 63

Met Asp Asp Cys Arg Phe Glu Thr Ser Glu Leu Gln Ala Ser Val Met

-continued

```
  1               5                  10                 15
Ile Ser Thr Pro Leu Phe Thr Asp Ser Trp Ser Ser Cys Asn Thr Ala
            20                  25                 30

Asn Cys Asn Gly Ser Ile Lys Ile His Asp Ile Ala Gly Ile Thr Tyr
            35                  40                 45

Val Ala Ile Pro Ala Val Ser Met Ile Gln Leu Gly Asn Leu Val Gly
 50                      55                 60

Leu Pro Val Thr Gly Asp Val Leu Phe Pro Gly Leu Ser Ser Asp Glu
 65                  70                  75                 80

Pro Leu Pro Met Val Asp Ala Ala Ile Leu Lys Leu Phe Leu Gln Leu
                85                  90                 95

Lys Ile Lys Glu Gly Leu Glu Leu Glu Leu Leu Gly Lys Lys Leu Val
            100                 105                110

Val Ile Thr Gly His Ser Thr Gly Gly Ala Leu Ala Ala Phe Thr Ala
            115                 120                125

Leu Trp Leu Leu Ser Gln Ser Ser Pro Pro Ser Phe Arg Val Phe Cys
130                 135                 140

Ile Thr Phe Gly Ser Pro Leu Leu Gly Asn Gln Ser Leu Ser Thr Ser
145                 150                 155                160

Ile Ser Arg Ser Arg Leu Ala His Asn Phe Cys His Val Val Ser Ile
            165                 170                175

His Asp Leu Val Pro Arg Ser Ser Asn Glu Gln Phe Trp Pro Phe Gly
            180                 185                 190

Thr Tyr Leu Phe Cys Ser Asp Lys Gly Val Cys Leu Asp Asn Ala
            195                 200                 205

Gly Ser Val Arg Leu Met Phe Asn Ile Leu Asn Thr Thr Ala Thr Gln
210                 215                 220

Asn Thr Glu Glu His Gln Arg Tyr Gly His Tyr Val Phe Thr Leu Ser
225                 230                 235                240

His Met Phe Leu Lys Ser Arg Ser Phe Leu Gly Gly Ser Ile Pro Asp
                245                 250                255

Asn Ser Tyr Gln Ala Gly Val Ala Leu Ala Val Glu Ala Leu Gly Phe
            260                 265                 270

Ser Asn Asp Asp Thr Ser Gly Val Leu Val Lys Glu Cys Ile Glu Thr
            275                 280                 285

Ala Thr Arg Ile Val Arg Ala Pro Ile Leu Arg Ser Ala Glu Leu Ala
            290                 295                 300

Asn Glu Leu Ala Ser Val Leu Pro Ala Arg Leu Glu Ile Gln Trp Tyr
305                 310                 315                320

Lys Asp Arg Cys Asp Ala Ser Glu Glu Gln Leu Gly Tyr Tyr Asp Phe
                325                 330                335

Phe Lys Arg Tyr Ser Leu Lys Arg Asp Phe Lys Val Asn Met Ser Arg
            340                 345                 350

Ile Arg Leu Ala Lys Phe Trp Asp Thr Val Ile Lys Met Val Glu Thr
            355                 360                 365

Asn Glu Leu Pro Phe Asp Phe His Leu Gly Lys Lys Trp Ile Tyr Ala
            370                 375                 380

Ser Gln Phe Tyr Gln Leu Leu Ala Glu Pro Leu Asp Ile Ala Asn Phe
385                 390                 395                400

Tyr Lys Asn Arg Asp Ile Lys Thr Gly Gly His Tyr Leu Glu Gly Asn
                405                 410                 415

Arg Pro Lys Arg Tyr Glu Val Ile Asp Lys Trp Gln Lys Gly Val Lys
            420                 425                 430
```

```
Val Pro Glu Glu Cys Val Arg Ser Arg Tyr Ala Ser Thr Thr Gln Asp
        435                 440                 445

Thr Cys Phe Trp Ala Lys Leu Glu Gln Ala Lys Glu Trp Leu Asp Glu
        450                 455                 460

Ala Arg Lys Glu Ser Ser Asp Pro Gln Arg Arg Ser Leu Leu Arg Glu
465                 470                 475                 480

Lys Ile Val Pro Phe Glu Ser Tyr Ala Asn Thr Leu Val Thr Lys Lys
                485                 490                 495

Glu Val Ser Leu Asp Val Lys Ala Lys Asn Ser Ser Tyr Ser Val Trp
            500                 505                 510

Arg Arg Ile
        515

<210> SEQ ID NO 64
<211> LENGTH: 56
<212> TYPE: PRT
<213> ORGANISM: Rhizomucor miehei

<400> SEQUENCE: 64

Thr Lys Val His Lys Gly Phe Leu Asp Ser Tyr Gly Glu Val Gln Asn
1               5                   10                  15

Glu Leu Val Ala Thr Val Leu Asp Gln Phe Lys Gln Tyr Pro Ser Tyr
            20                  25                  30

Lys Val Ala Val Thr Gly His Ser Leu Gly Gly Ala Thr Ala Leu Leu
        35                  40                  45

Cys Ala Leu Gly Leu Tyr Gln Arg
    50                  55

<210> SEQ ID NO 65
<211> LENGTH: 53
<212> TYPE: PRT
<213> ORGANISM: Rhizomucor miehei

<400> SEQUENCE: 65

Gly Leu Tyr Gln Arg Glu Glu Gly Leu Ser Ser Asn Leu Phe Leu
1               5                   10                  15

Tyr Thr Gln Gly Gln Pro Arg Val Gly Asp Pro Ala Phe Ala Asn Tyr
            20                  25                  30

Val Val Ser Thr Gly Ile Pro Tyr Arg Arg Thr Val Asn Glu Arg Asp
        35                  40                  45

Ile Val Pro His Leu
        50

<210> SEQ ID NO 66
<211> LENGTH: 15
<212> TYPE: PRT
<213> ORGANISM: Rhizomucor miehei

<400> SEQUENCE: 66

Ile Val Pro Phe Thr Ser Val Leu Asp His Leu Ser Tyr Phe Gly
1               5                   10                  15

<210> SEQ ID NO 67
<211> LENGTH: 52
<212> TYPE: PRT
<213> ORGANISM: Fusarium heterosporum

<400> SEQUENCE: 67

Val His Thr Gly Phe Leu Asp Ala Trp Glu Glu Val Ala Ala Asn Val
```

-continued

```
                1               5                  10                 15
Lys Ala Ala Val Ser Ala Ala Lys Thr Ala Asn Pro Thr Phe Lys Phe
                    20                  25                  30

Val Val Thr Gly His Ser Leu Gly Gly Ala Val Ala Thr Ile Ala Ala
            35                  40                  45

Ala Tyr Leu Arg
        50
```

<210> SEQ ID NO 68
<211> LENGTH: 47
<212> TYPE: PRT
<213> ORGANISM: Fusarium heterosporum

<400> SEQUENCE: 68

```
Leu Arg Lys Asp Gly Phe Pro Phe Asp Leu Tyr Thr Tyr Gly Ser Pro
 1               5                  10                  15

Arg Val Gly Asn Asp Phe Ala Asn Phe Val Thr Gln Gln Thr Gly
            20                  25                  30

Ala Glu Tyr Arg Val Thr His Gly Asp Asp Pro Val Pro Arg Leu
        35                  40                  45
```

<210> SEQ ID NO 69
<211> LENGTH: 15
<212> TYPE: PRT
<213> ORGANISM: Fusarium heterosporum

<400> SEQUENCE: 69

```
Gly Thr Ile Gly Leu Asp Ile Leu Ala His Ile Thr Tyr Phe Gln
 1               5                  10                  15
```

<210> SEQ ID NO 70
<211> LENGTH: 56
<212> TYPE: PRT
<213> ORGANISM: Rhizopus niveus

<400> SEQUENCE: 70

```
Ala Lys Val His Ala Gly Phe Leu Ser Ser Tyr Glu Gln Val Val Asn
 1               5                  10                  15

Asp Tyr Phe Pro Val Val Gln Glu Gln Leu Thr Ala His Pro Thr Tyr
            20                  25                  30

Lys Val Ile Val Thr Gly His Ser Leu Gly Gly Ala Gln Ala Leu Leu
        35                  40                  45

Ala Gly Met Asp Leu Tyr Gln Arg
        50                  55
```

<210> SEQ ID NO 71
<211> LENGTH: 51
<212> TYPE: PRT
<213> ORGANISM: Rhizopus niveus

<400> SEQUENCE: 71

```
Tyr Gln Arg Glu Pro Arg Leu Ser Pro Lys Asn Leu Ser Ile Phe Thr
 1               5                  10                  15

Val Gly Gly Pro Arg Val Gly Asn Pro Thr Phe Ala Tyr Tyr Val Glu
            20                  25                  30

Ser Thr Gly Ile Pro Phe Gln Arg Thr Val His Lys Arg Asp Ile Val
        35                  40                  45

Pro His Val
        50
```

```
<210> SEQ ID NO 72
<211> LENGTH: 15
<212> TYPE: PRT
<213> ORGANISM: Rhizopus niveus

<400> SEQUENCE: 72

Ile Val Pro Phe Thr Ser Ile Leu Asp His Leu Ser Tyr Phe Asp
 1               5                  10                  15

<210> SEQ ID NO 73
<211> LENGTH: 54
<212> TYPE: PRT
<213> ORGANISM: Thermomyces lanuginosus

<400> SEQUENCE: 73

Cys Arg Gly His Asp Gly Phe Thr Ser Ser Trp Arg Ser Val Ala Asp
 1               5                  10                  15

Thr Leu Arg Gln Lys Val Glu Asp Ala Val Arg Glu His Pro Asp Tyr
            20                  25                  30

Arg Val Val Phe Thr Gly His Ser Leu Gly Gly Ala Leu Ala Thr Val
        35                  40                  45

Ala Gly Ala Asp Leu Arg
    50

<210> SEQ ID NO 74
<211> LENGTH: 48
<212> TYPE: PRT
<213> ORGANISM: Thermomyces lanuginosus

<400> SEQUENCE: 74

Leu Arg Gly Asn Gly Tyr Asp Ile Asp Val Phe Ser Tyr Gly Ala Pro
 1               5                  10                  15

Arg Val Gly Asn Arg Ala Phe Ala Glu Phe Leu Thr Val Gln Thr Gly
            20                  25                  30

Gly Thr Leu Tyr Arg Ile Thr His Thr Asn Asp Ile Val Pro Arg Leu
        35                  40                  45

<210> SEQ ID NO 75
<211> LENGTH: 15
<212> TYPE: PRT
<213> ORGANISM: Thermomyces lanuginosis

<400> SEQUENCE: 75

Gln Pro Asn Ile Pro Asp Ile Pro Ala His Leu Trp Tyr Phe Gly
 1               5                  10                  15

<210> SEQ ID NO 76
<211> LENGTH: 54
<212> TYPE: PRT
<213> ORGANISM: Aspergillus niger

<400> SEQUENCE: 76

Cys Glu Val His Gly Gly Tyr Tyr Ile Gly Trp Ile Ser Val Gln Asp
 1               5                  10                  15

Gln Val Glu Ser Leu Val Lys Gln Gln Ala Ser Gln Tyr Pro Asp Tyr
            20                  25                  30

Ala Leu Thr Val Thr Gly His Ser Leu Gly Ala Ser Met Ala Ala Leu
        35                  40                  45

Thr Ala Ala Gln Leu Ser
    50
```

```
<210> SEQ ID NO 77
<211> LENGTH: 53
<212> TYPE: PRT
<213> ORGANISM: Aspergillus niger

<400> SEQUENCE: 77

Ser Ala Thr Tyr Asp Asn Val Arg Leu Tyr Thr Phe Gly Glu Pro Arg
  1               5                  10                  15

Ser Gly Asn Gln Ala Phe Ala Ser Tyr Met Asn Asp Ala Phe Gln Val
             20                  25                  30

Ser Ser Pro Glu Thr Thr Gln Tyr Phe Arg Val Thr His Ser Asn Asp
         35                  40                  45

Gly Ile Pro Asn Leu
         50

<210> SEQ ID NO 78
<211> LENGTH: 15
<212> TYPE: PRT
<213> ORGANISM: Aspergillus niger

<400> SEQUENCE: 78

Gln Gly Gly Gln Gly Val Asn Asp Ala His Thr Thr Tyr Phe Gly
  1               5                  10                  15

<210> SEQ ID NO 79
<211> LENGTH: 60
<212> TYPE: PRT
<213> ORGANISM: Arabidopsis thaliana

<400> SEQUENCE: 79

Ala Thr Val Asn Glu Ala Phe Leu Lys Asn Leu Glu Ala Val Ile Asp
  1               5                  10                  15

Pro Arg Thr Ser Phe Gln Ala Ser Val Glu Met Ala Val Arg Ser Arg
             20                  25                  30

Lys Gln Ile Val Phe Thr Gly His Ser Ser Gly Gly Ala Thr Ala Ile
         35                  40                  45

Leu Ala Thr Val Trp Tyr Leu Glu Lys Tyr Phe Ile
         50                  55                  60

<210> SEQ ID NO 80
<211> LENGTH: 48
<212> TYPE: PRT
<213> ORGANISM: Arabidopsis thaliana

<400> SEQUENCE: 80

Pro Asn Val Tyr Leu Glu Pro Arg Cys Val Thr Phe Gly Ala Pro Leu
  1               5                  10                  15

Val Gly Asp Ser Ile Phe Ser His Ala Leu Gly Arg Glu Lys Trp Ser
             20                  25                  30

Arg Phe Phe Val Asn Phe Val Thr Arg Phe Asp Ile Val Pro Arg Ile
         35                  40                  45

<210> SEQ ID NO 81
<211> LENGTH: 15
<212> TYPE: PRT
<213> ORGANISM: Arabidopsis thaliana

<400> SEQUENCE: 81

Leu Ile Pro Phe Arg Ser Ile Arg Asp His His Ser Tyr Glu Glu
  1               5                  10                  15
```

-continued

```
<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence:
      gene-specific primer for 5' RACE product

<400> SEQUENCE: 82
cgtgaaattg aggtggagag agattggttt ccg                              33

<210> SEQ ID NO 83
<211> LENGTH: 35
<212> TYPE: DNA
<213> ORGANISM: Artificial Sequence
<220> FEATURE:
<223> OTHER INFORMATION: Description of Artificial Sequence:
      gene-specific primer for 3' RACE product

<400> SEQUENCE: 83
gaattgttag gtaaaaagct ggtggtgata accgg                            35

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: primer for
      isolation of a complete PAD4 cDNA corresponding to one end of cDNA
      sequence

<400> SEQUENCE: 84
atggacgatt gtcgagacga g                                           21

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: primer for
      isolation of a complete PAD4 cDNA corresponding to the other end
      of the cDNA sequence

<400> SEQUENCE: 85
agaatatata gtaacattca tcagaaagtc                                  30
```